(12) United States Patent
Adam et al.

(10) Patent No.: US 7,232,467 B2
(45) Date of Patent: Jun. 19, 2007

(54) METHOD OF COLORING POROUS MATERIAL

(75) Inventors: Jean-Marie Adam, Rosenau (FR); Taher Yousaf, Basel (CH); Beate Fröhling, Steinen (DE); Victor Paul Eliu, Lörrach (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 122 days.

(21) Appl. No.: 10/525,300

(22) PCT Filed: Aug. 26, 2003

(86) PCT No.: PCT/EP03/09416

§ 371 (c)(1),
(2), (4) Date: Feb. 14, 2005

(87) PCT Pub. No.: WO2004/019896

PCT Pub. Date: Mar. 11, 2004

(65) Prior Publication Data

US 2005/0251932 A1 Nov. 17, 2005

(30) Foreign Application Priority Data

Sep. 2, 2002 (EP) .................................. 02405753

(51) Int. Cl.
*A61K 7/13* (2006.01)
(52) U.S. Cl. ................. 8/405; 8/437; 8/451; 8/466; 8/565; 8/566; 8/567; 8/575; 8/607; 8/666; 8/688; 132/202; 132/208; 544/180; 544/224
(58) Field of Classification Search .................. 8/405, 8/437, 451, 466, 565, 566, 567, 575, 607, 8/666, 688; 544/180, 224; 132/202, 206
See application file for complete search history.

(56) References Cited

U.S. PATENT DOCUMENTS

| | | | | |
|---|---|---|---|---|
| 1,858,623 | A | * | 5/1932 | Hentrich et al. ............. 534/554 |
| 1,871,850 | A | * | 8/1932 | Hentrich et al. ............. 534/554 |
| 1,874,524 | A | * | 8/1932 | Hentrich et al. ............. 534/554 |
| 1,882,556 | A | | 10/1932 | Hentrich et al. |
| 1,882,562 | A | | 10/1932 | Glietenberg et al. |
| 2,643,990 | A | * | 6/1953 | Ham ........................... 534/554 |
| 3,582,253 | A | | 6/1971 | Berth et al. ..................... 8/10.1 |
| 3,976,633 | A | * | 8/1976 | Berkoff et al. ............... 534/554 |
| 4,168,952 | A | | 9/1979 | Bühler et al. .................. 8/10.1 |
| 4,268,600 | A | | 5/1981 | Robillard et al. ............ 430/142 |
| 6,358,286 | B2 | * | 3/2002 | Lang et al. ..................... 8/409 |
| 7,041,143 | B2 | * | 5/2006 | Adam et al. ..................... 8/429 |
| 2001/0012559 | A1 | | 8/2001 | Zambounis et al. ...... 428/304.4 |
| 2004/0083560 | A1 | | 5/2004 | Adam et al. ..................... 8/432 |

FOREIGN PATENT DOCUMENTS

| | | |
|---|---|---|
| DE | 11 31 641 | 6/1962 |
| DE | 12 13 374 | 3/1966 |
| DE | 30 09 833 | 10/1981 |
| DE | 198 42 071 | 3/2000 |
| DE | 199 49 033 | 4/2001 |

OTHER PUBLICATIONS

Kasthurikrishnan et al., J. Am. Soc. Mass Spectrom., 9(3), 234-241, 1998.*
STIC Search REport filed on Sep. 19, 2006.*

* cited by examiner

*Primary Examiner*—Eisa Elhilo
(74) *Attorney, Agent, or Firm*—Mervin G. Wood; Tyler A. Stevenson

(57) ABSTRACT

A method of colouring porous material, especially human hair, is described, which method comprises applying to the material being coloured, in any desired order successively, or simultaneously, a) at least one capped diazonium compound of Formula (1) and/or at least one compound of Formula (2) and/or at least one compound of Formula (3) wherein Q is an unsubstituted or substituted aromatic or heterocyclic residue, R is the radical of an unsubstituted or substituted, water-soluble aliphatic or aromatic amine, and T is an unsubstituted or substituted, water-soluble aliphatic or aromatic residue, wherein at least one of the groups must contain a radical imparting water solubility, and a) at least one water-soluble coupling component under conditions such that, initially, coupling does not take place, and then causing the capped diazonium compound present on the material to react with the coupling component

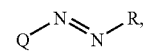
(1)

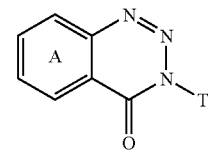

(2)

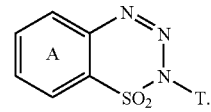

(3)

14 Claims, No Drawings

METHOD OF COLORING POROUS MATERIAL

The present invention relates to a method of colouring porous material, for example metal, wood or keratin-containing fibres, especially human hair, using developing dyes, that is to say dyes which are formed inside the pores of the substrate.

Colouring with the aid of developing dyes has been known for a long time and has also been generally used for dyeing cotton. The dyes and the colouring methods used therefore do not, however, provide satisfactory results for colouring hair.

For colouring hair, therefore, oxidation dyes are used in most cases; however, they too are not capable of satisfying all requirements. The fastness to washing properties are often inadequate and, in addition, the colouring conditions required often cause a greater or lesser amount of damage to the hair. There has therefore been a need for a colouring method which does not have the mentioned disadvantages or which has them to an insignificant degree.

The present invention relates to a method of colouring porous material, which comprises applying to the material being coloured, in any desired order successively, or simultaneously,
a) at least one capped diazonium compound and
b) at least one water-soluble coupling component
under conditions such that, initially, coupling does not take place, and then causing the capped diazonium compound present on the material to react with the coupling component.

The colorations obtained are distinguished by outstanding fastness to washing properties, which are significantly better than in the case of colorations with oxidation dyes, and there is virtually no damage to the hair. Moreover, there is no staining of the scalp, because the dye components do not penetrate into the skin and non-fixed dye can be washed off readily.

Suitable capped diazonium compounds include, for example, compounds of formula (1) compounds of formula (2)

(1)

(2)

and compounds of formula (3)

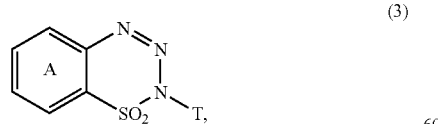
(3)

wherein
Q is an unsubstituted or substituted aromatic or heterocyclic residue,
R is the radical of an unsubstituted or substituted, water-soluble aliphatic or aromatic amine,
and
T is an unsubstituted or substituted, water-soluble aliphatic or aromatic residue,
wherein at least one of the groups must contain a radical imparting water solubility.

Suitable radicals imparting water solubility include, for example, $SO_3H$, $COOH$ or $OH$.

Q is an unsubstituted or substituted aromatic or heterocyclic residue. For example, unsubstituted or substituted phenyl, naphthyl, thiophenyl, 1,3-thiazolyl, 1,2-thiazolyl, 1,3-benzothiazolyl, 2,3-benzothiazolyl, imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl, aminodiphenyl, aminodiphenylether and azobenzenyl are suitable.

Such radicals may be mono- or poly-substituted, for example by $C_1$–$C_4$alkyl, $C_1$–$C_4$alkoxy, $C_1$–$C_4$alkylthio, halogen, e.g. fluorine, bromine or chlorine, nitro, trifluoromethyl, CN, SCN, $C_1$–$C_4$alkylsulfonyl, phenylsulfonyl, benzylsulfonyl, di-$C_1$–$C_4$alkylaminosulfonyl, $C_1$–$C_4$alkylcarbonylamino, $C_1$–$C_4$alkoxysulfonyl or by di-(hydroxy-$C_1$–$C_4$alkyl)-aminosulfonyl.

Examples of suitable radicals Q are as follows:

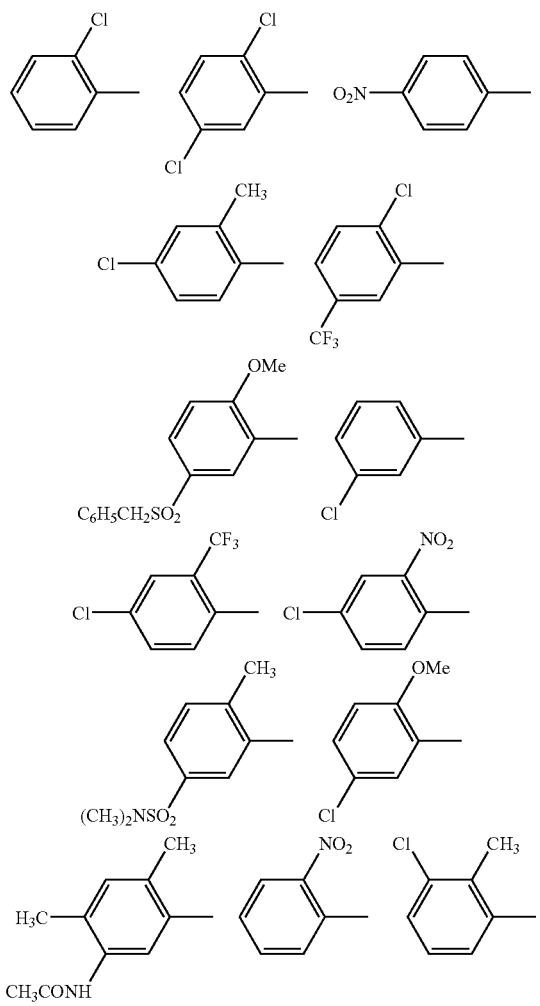

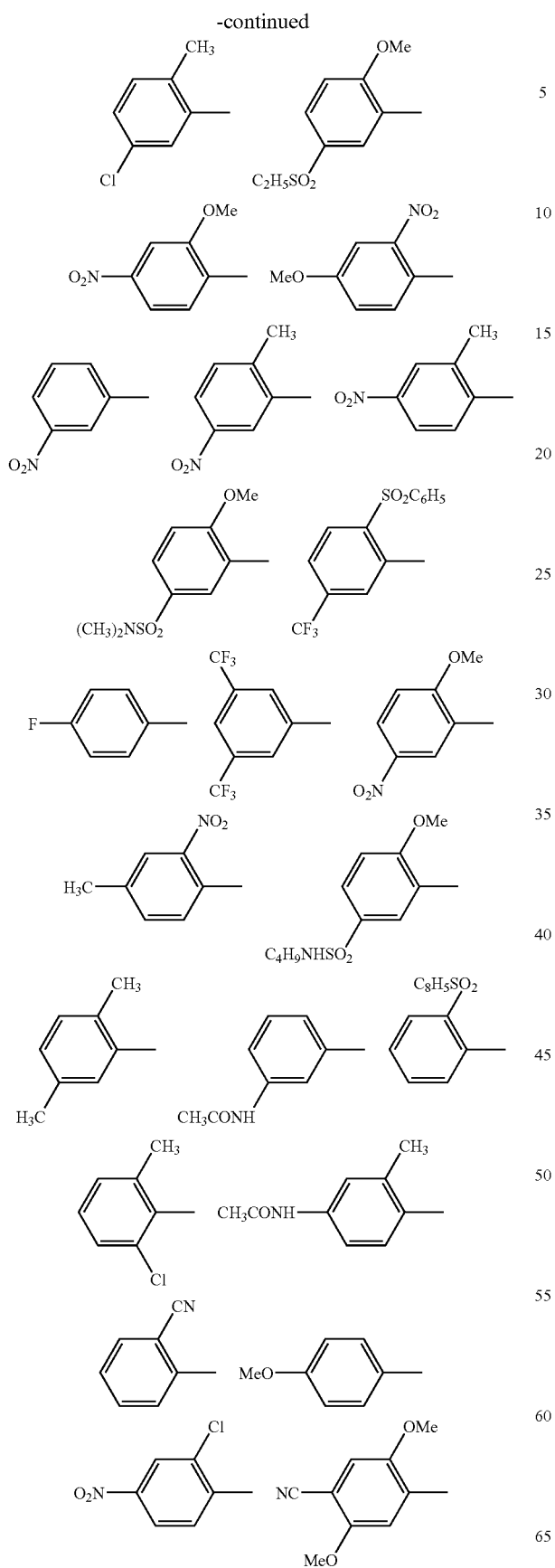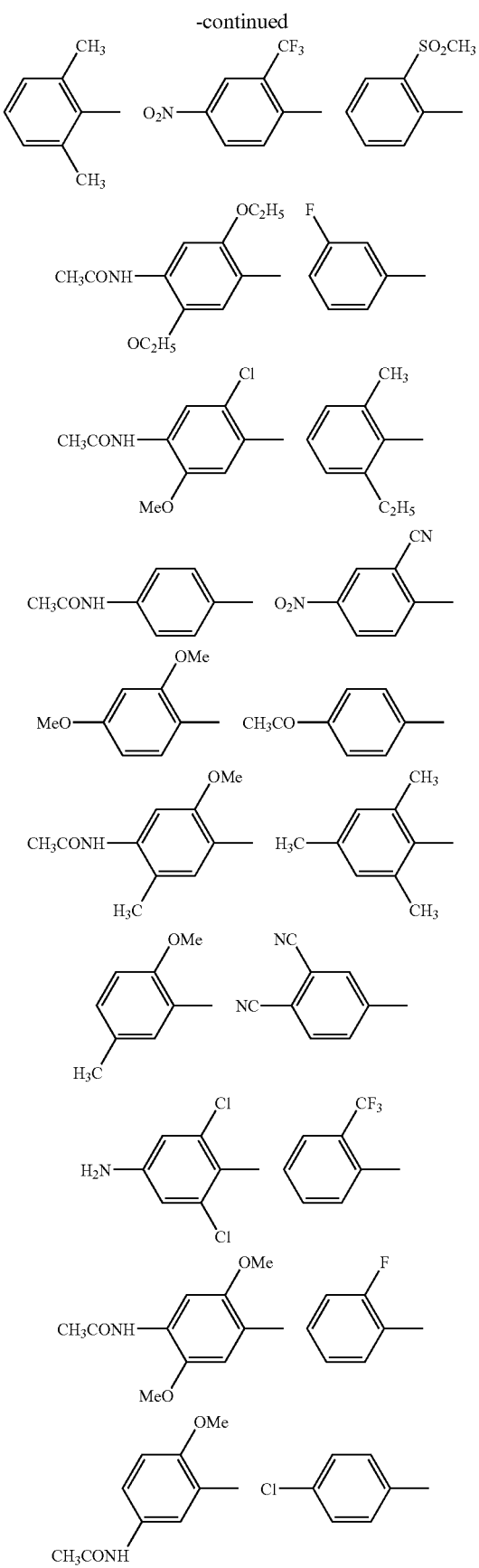

-continued

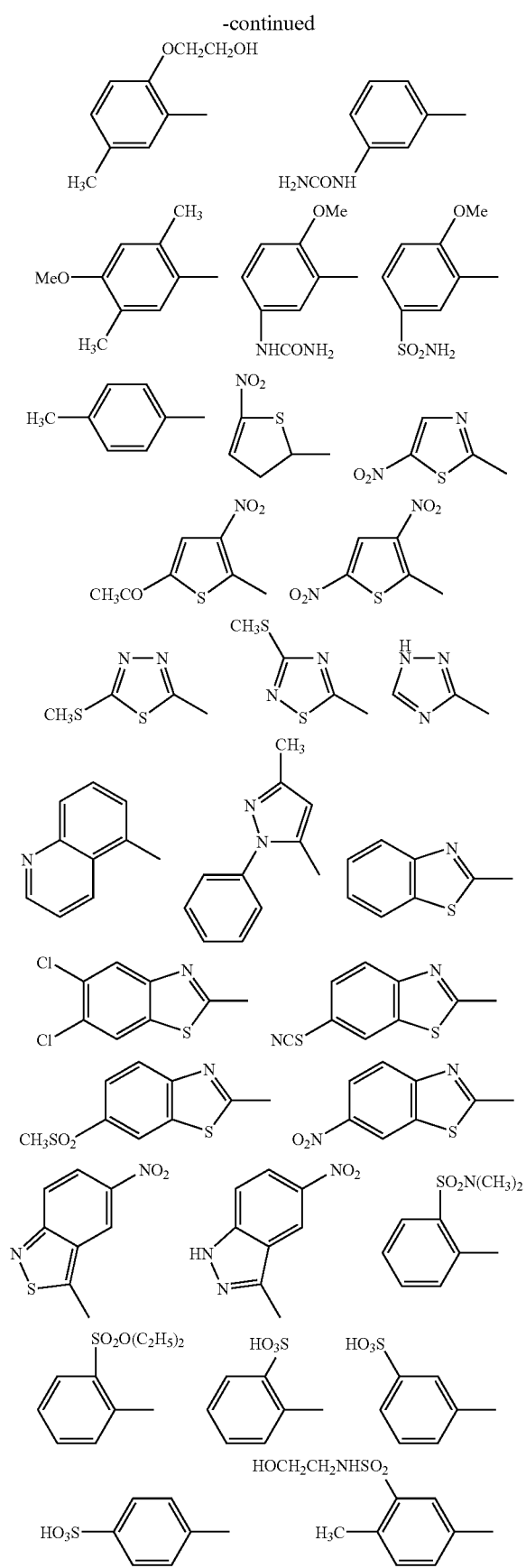
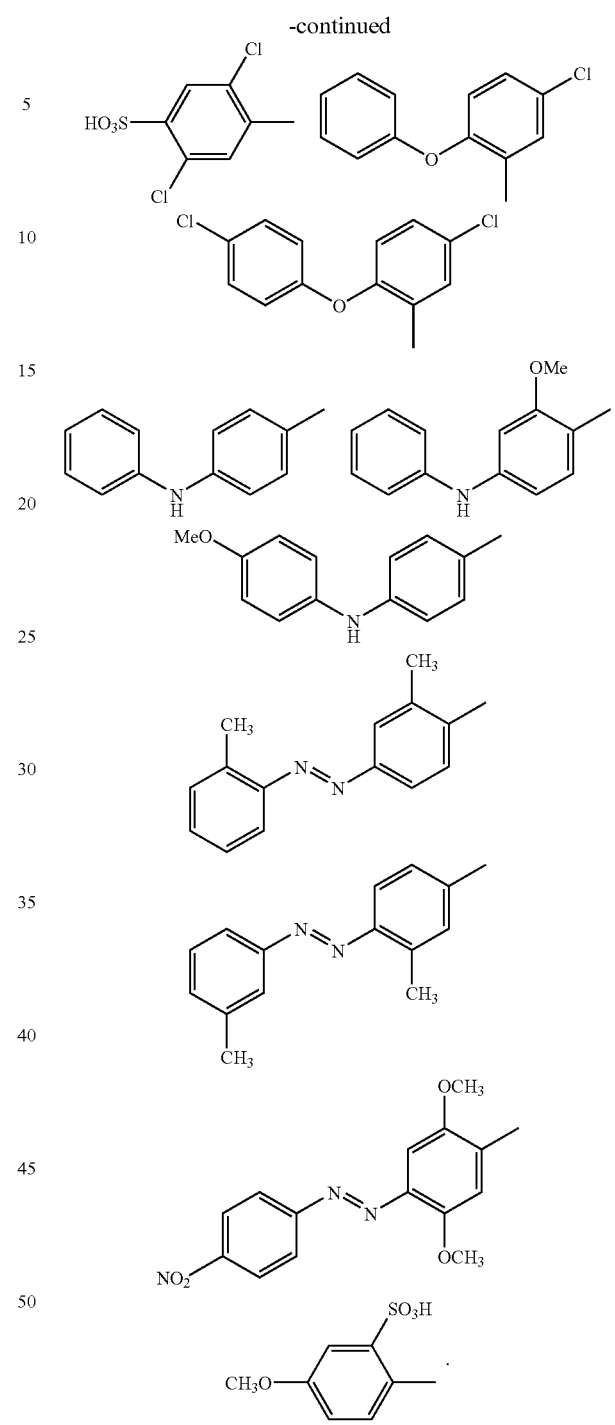

R is the radical of an unsubstituted or substituted, water-soluble aliphatic or aromatic amine.

Preferably, R is a radical of formula $-NR_{16}R_{17}$, wherein $R_{16}$ is H; unsubstituted linear or branched $C_1$–$C_6$alkyl or linear or branched $C_1$–$C_6$alkyl, which is substituted by one or more identical or different substituent selected from the group consisting of $OC_1$–$C_4$alkyl, COOH, $COOC_1$–$C_2$alkyl, $SO_3H$, $NH_2$, CN, halogen and OH, and $R_{17}$ is unsubstituted linear or branched $C_1$–$C_6$alkyl or linear or branched $C_1$–$C_6$alkyl, which is substituted by one or more identical or different substituent selected from the group consisting of $OC_1$–$C_4$alkyl, COOH, $COOC_1$–$C_2$alkyl, $SO_3H$, $NH_2$, CN, halogen and OH.

More preferably, R is a radical of $-NR_{16}R_{17}$, wherein $R_{16}$ and $R_{17}$ are $C_1$–$C_4$alkyl, mono-substituted by $OC_1$–$C_2$alkyl, COOH, $COOC_1$–$C_2$alkyl, $SO_3H$, $NH_2$, CN, halogen or OH. Example for suitable amine compounds (R—H) are methylaminoacetic acid (sarcosine), methylaminobutyric acid, methylaminopropionic acid, ethylaminoacetic acid, ethylaminobutyric acid, 1-methylamino-ethane-2-sulfonic acid, 1-ethylamino-ethane-2-sulfonic acid and 1-methylamino-propane-3-sulfonic acid.

Preferably, R also signifies the radical of unsubstituted aniline; the radical of unsubstituted aminonaphthalene; the radical of aniline or aminonaphthalene, wherein the phenyl or the naphthyl ring is substituted by one or more identical or different substituent selected from the group consisting of COOH, $SO_3H$, CN, halogen, $SO_2C_1$–$C_2$alkyl, unsubstituted linear or branched $C_1$–$C_4$alkyl, linear or branched $C_1$–$C_4$alkyl, substituted by OH, carboxy, $COC_1$–$C_2$alkyl or $SO_2$—$N(C_1$–$C_4$alkyl$)$-$(CH_2)_{1-4}SO_3H$ and wherein the amino radical is substituted by H, unsubstituted linear or branched $C_1$–$C_4$alkyl or linear or branched $C_1$–$C_4$alkyl, substituted by OH or carboxy.

Suitable radicals of such aromatic amines are, for example, as follows:

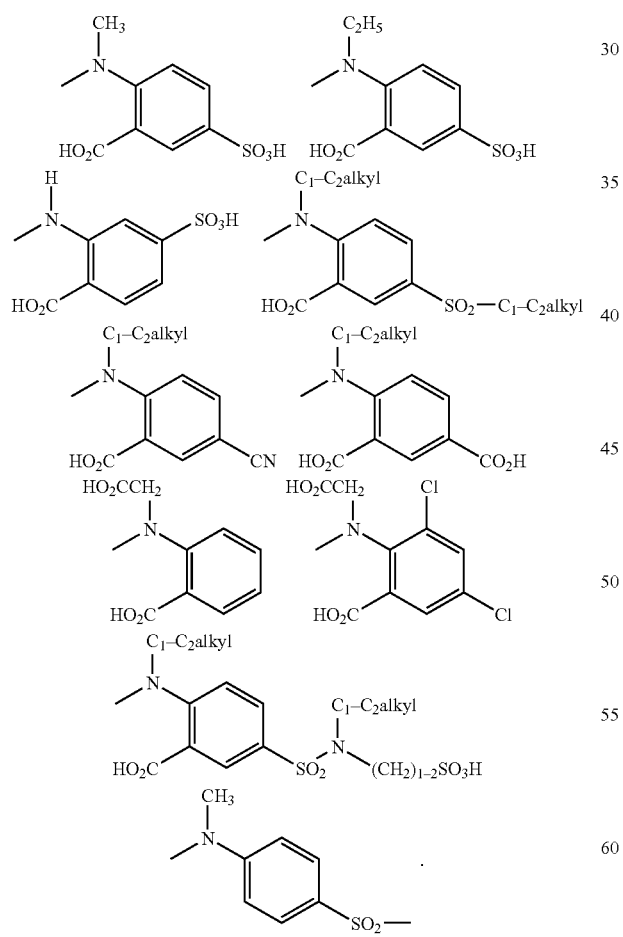

T is an unsubstituted or substituted, water-soluble aliphatic or aromatic residue.

Preferably, T is a linear or branched unsubstituted $C_1$–$C_6$alkyl or linear or branched $C_1$–$C_6$alkyl, which is substituted by one or more identical or different substituent selected from the group consisting of $OC_1$–$C_4$alkyl, COOH, $COOC_1$–$C_2$alkyl, $SO_3H$, $NH_2$, $NH(C_1$–$C_2$alkyl$)$, $N(C_1$–$C_2$alkyl$)_2$, CN, halogen and OH.

More preferably, T is a linear or branched $C_1$–$C_6$alkyl, which is substituted by one or two identical or different substituent selected from the group consisting of COOH, $NH_2$, $NH(C_1$–$C_2$alkyl$)$, $N(C_1$–$C_2$alkyl$)_2$ and $SO_3H$.

Examples for such suitable radicals are $-CH_2COOH$, $-(CH_2)_2COOH$, $-(CH_2)_3COOH$, $-CH(NHCH_2CH_3)COOH$, $-CH_2CH_2SO_3H$ and $-CH_2CH_2CH_2SO_3H$.

Preferably, T is also unsubstituted phenyl; unsubstituted naphthyl; phenyl or naphthyl, which are substituted by one or more identical or different substituents selected from the group consisting of $OC_1$–$C_4$alkyl, COOH, $COOC_1$–$C_2$alkyl, $SO_3H$, $NH_2$, $NH(C_1$–$C_2$alkyl$)$, $N(C_1$–$C_2$alkyl$)_2$, CN, halogen and OH.

Such suitable aromatic residues are, for example, as follows:

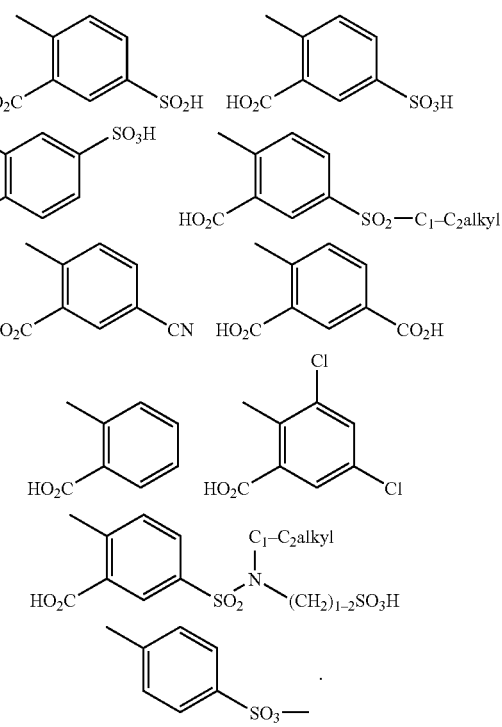

A preferred embodiment of the present invention is a method of colouring porous material, which comprises applying to the material being coloured, in any desired order successively, or simultaneously, a) at least one capped diazonium compound of formula (1)

(1)

and/or at least one compound of formula (2)

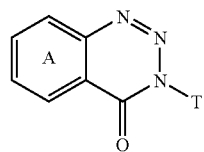

and/or at least one compound of formula (3)

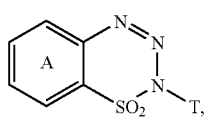

wherein
Q is an unsubstituted phenyl; naphthyl; thiophenyl; 1,3-thiazolyl; 1,2-thiazolyl; 1,3-benzothiazolyl; 2,3-benzothiazolyl; imidazolyl; 1,3,4-thiadiazolyl; 1,3,5-thiadiazolyl; 1,3,4-triazolyl; pyrazolyl; benzimidazolyl; benzopyrazolyl; pyridinyl; quinolinyl; pyrimidinyl; isoxazolyl; aminodiphenyl; aminodiphenylether and azobenzenyl or Q is a phenyl, naphthyl, thiophenyl, 1,3-thiazolyl, 1,2-thiazolyl, 1,3-benzothiazolyl, 2,3-benzothiazolyl, imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl, aminodiphenyl, aminodiphenylether and azobenzenyl which is mono- or poly-substituted by $C_1$–$C_4$alkyl, $C_1$–$C_4$alkoxy, $C_1$–$C_4$alkylthio, halogen, e.g. fluorine, bromine or chlorine, nitro, trifluoromethyl, CN, SCN, $C_1$–$C_4$alkylsulfonyl, phenylsulfonyl, benzylsulfonyl, di-$C_1$–$C_4$alkylaminosulfonyl, $C_1$–$C_4$alkyl-carbonylamino, $C_1$–$C_4$alkoxysulfonyl or by di-(hydroxy-$C_1$–$C_4$alkyl)-aminosulfonyl, R is a radical of formula —$NR_{16}R_{17}$, wherein $R_{16}$ is H; unsubstituted linear or branched $C_1$–$C_6$alkyl or linear or branched $C_1$–$C_6$alkyl, which is substituted by one or more identical or different substituent selected from the group consisting of $OC_1$–$C_4$alkyl, COOH, $COOC_1$–$C_2$alkyl, $SO_3H$, $NH_2$, CN, halogen and OH, and $R_{17}$ is unsubstituted linear or branched $C_1$–$C_6$alkyl or linear or branched $C_1$–$C_6$alkyl, which is substituted by one or more identical or different substituent selected from the group consisting of $OC_1$–$C_4$alkyl, COOH, $COOC_1$–$C_2$alkyl, $SO_3H$, $NH_2$, CN, halogen and OH, or R is the radical of unsubstituted aniline; the radical of unsubstituted aminonaphthalene; the radical of aniline or aminonaphthalene, wherein the phenyl or the naphthyl ring is substituted by one or more identical or different substituent selected from the group consisting of COOH, $SO_3H$, CN, halogen, $SO_2C_1$–$C_2$alkyl, unsubstituted linear or branched $C_1$–$C_4$alkyl, linear or branched $C_1$–$C_4$alkyl, substituted by OH, carboxy, $COC_1$–$C_2$alkyl or $SO_2$—N($C_1$–$C_4$alkyl)-$(CH_2)_{1-4}SO_3H$ and wherein the amino radical is substituted by H, unsubstituted linear or branched $C_1$–$C_4$alkyl or linear or branched $C_1$–$C_4$alkyl, substituted by OH or carboxy, T is a linear or branched unsubstituted $C_1$–$C_6$alkyl or linear or branched $C_1$–$C_6$alkyl, which is substituted by one or more identical or different substituent selected from the group consisting of $OC_1$–$C_4$alkyl, COOH, $COOC_1$–$C_2$alkyl, $SO_3H$, $NH_2$, $NH(C_1$–$C_2$alkyl), $N(C_1$–$C_2$alkyl)$_2$, CN, halogen and OH, or T is unsubstituted phenyl; unsubstituted naphthyl; phenyl or naphthyl, which are substituted by one or more identical or different substituents selected from the group consisting of $OC_1$–$C_4$alkyl, COOH, $COOC_1$–$C_2$alkyl, $SO_3H$, $NH_2$, $NH(C_1$–$C_2$alkyl), $N(C_1$–$C_2$alkyl)$_2$, CN, halogen and OH, and b) at least one water-soluble coupling component under conditions such that, initially, coupling does not take place, and then causing the capped diazonium compound present on the material to react with the coupling component, with the provisos that if the water-soluble coupling component is

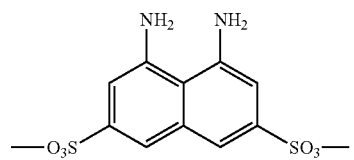

then the capped diazonium compounds is not

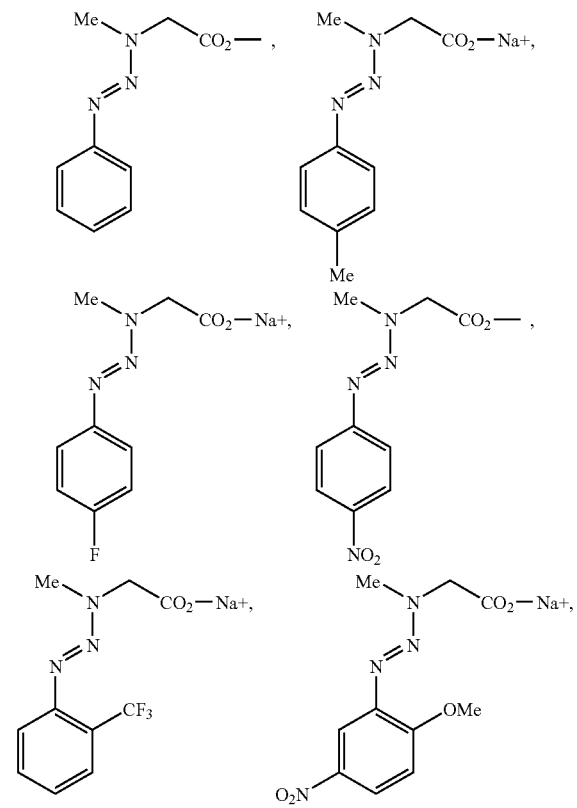

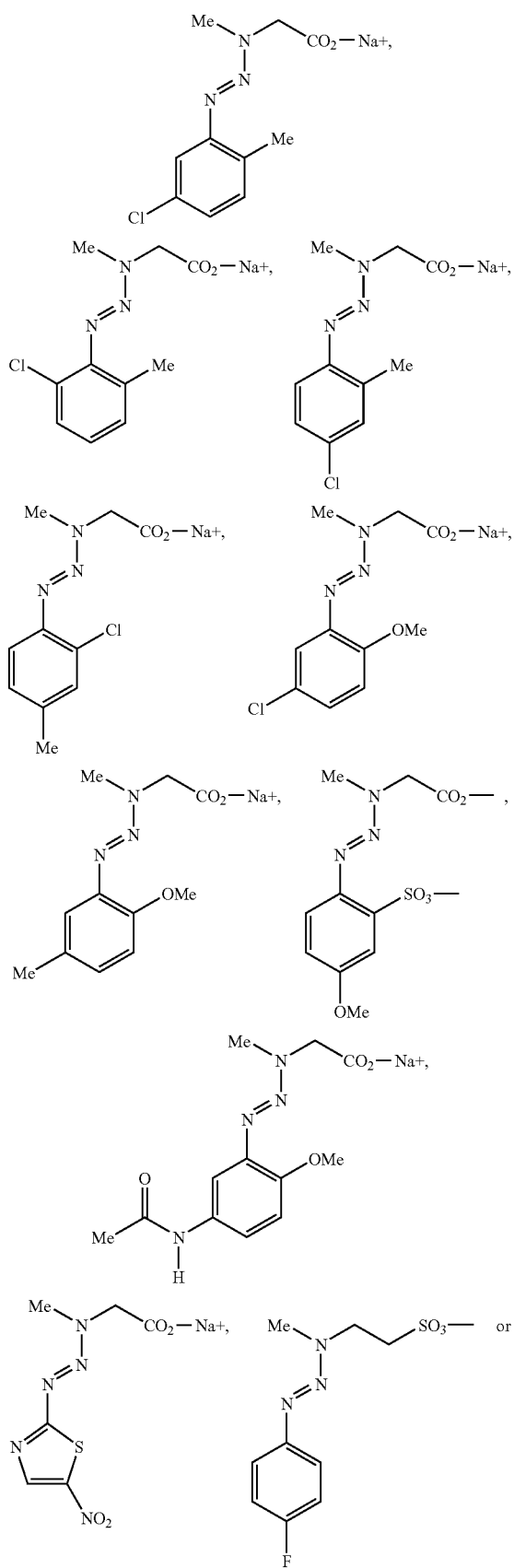
then the capped diazonium compound is not

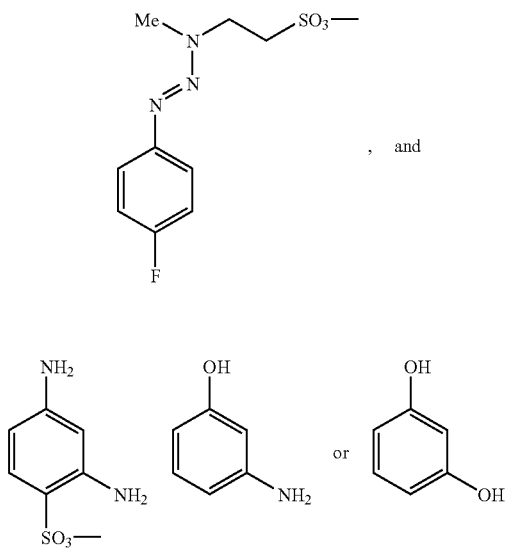
then the capped diazonium compound is not
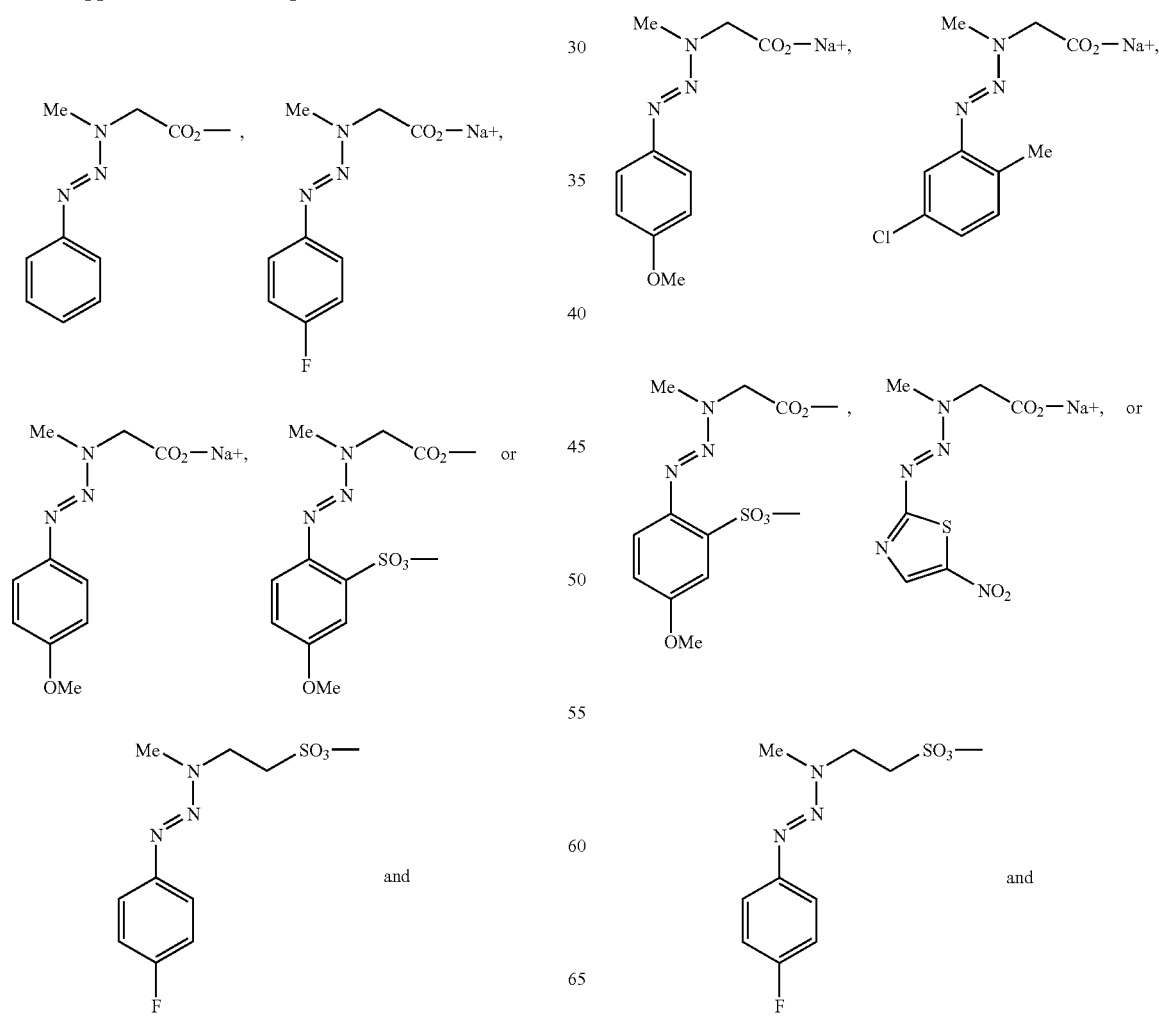
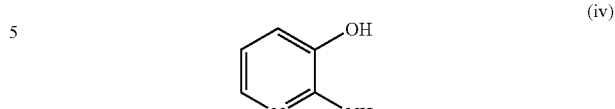
then the capped diazonium compound is not
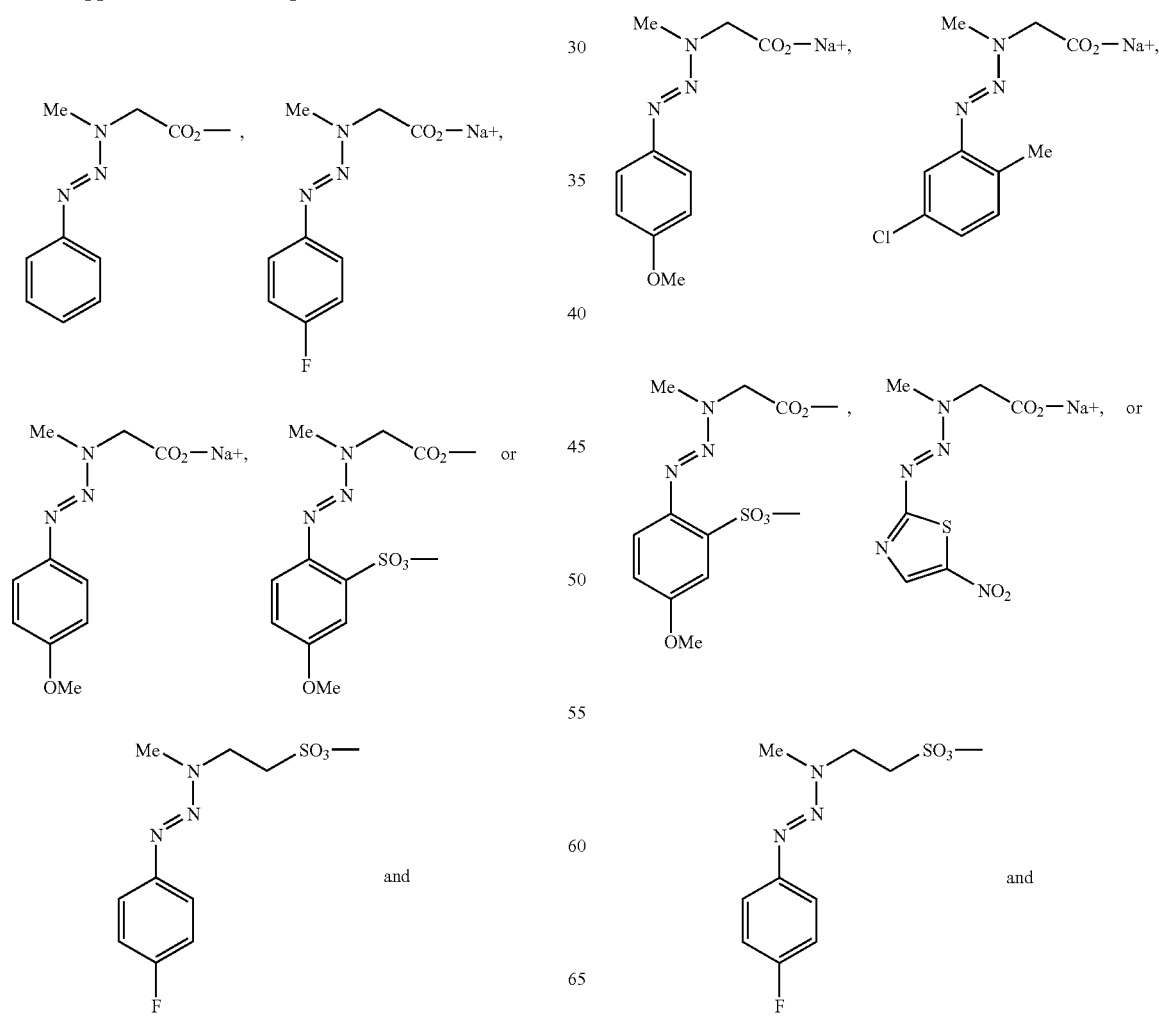

-continued
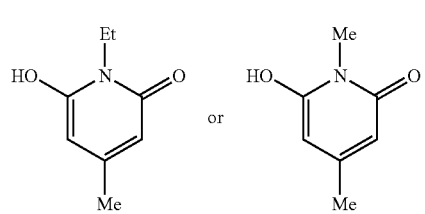
(v)
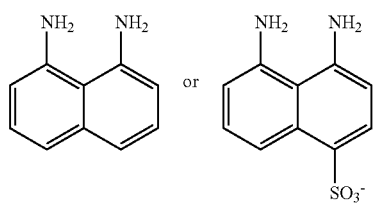
(vii)
then the capped diazonium compound is not
then the capped diazonium compound is not
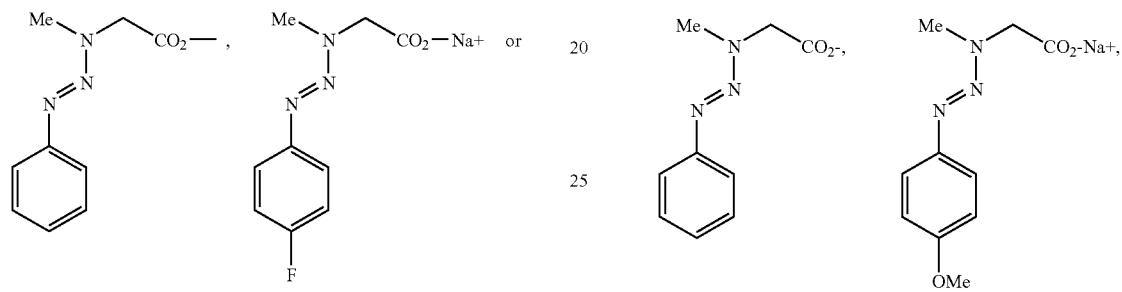
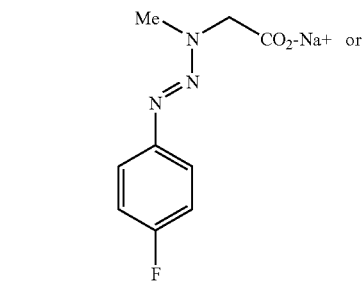
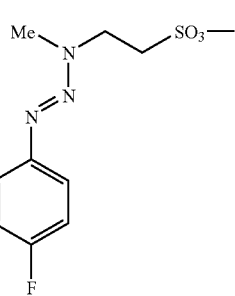
, and
(vi)
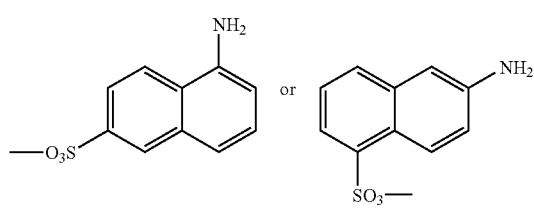
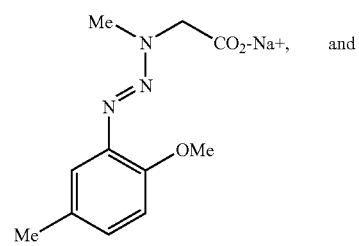
then the capped diazonium compound is not
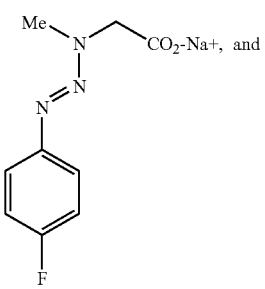
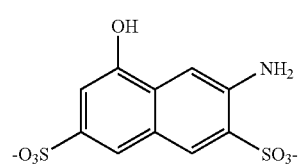
(viii)

then the capped diazonium compound is not

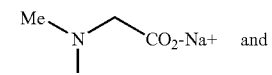

and

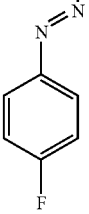                                          (ix)

then the capped diazonium compound is not

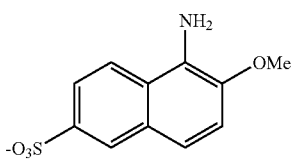                                          (x)

then the diazonium capped compound is not

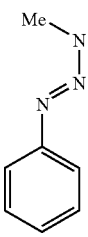

The provisos (i)–(x) exclude the Examples 5–67 of the International Application PCT/EP02/02146.

A more preferred embodiment of the present invention is a method of colouring porous material, which comprises applying to the material being coloured, in any desired order successively, or simultaneously, a) at least one capped diazonium compound of formula (1)

$$Q-N=N-R, \quad (1)$$

and/or at least one compound of formula (2)

(2)

and/or at least one compound of formula (3)

(3)

wherein

Q is an unsubstituted phenyl; naphthyl; thiophenyl; 1,3-thiazolyl; 1,2-thiazolyl; 1,3-benzothiazolyl; 2,3-benzothiazolyl; imidazolyl; 1,3,4-thiadiazolyl; 1,3,5-thiadiazolyl; 1,3,4-triazolyl; pyrazolyl; benzimidazolyl; benzopyrazolyl; pyridinyl; quinolinyl; pyrimidinyl; isoxazolyl; aminodiphenyl; aminodiphenylether and azobenzenyl or Q is a phenyl, naphthyl, thiophenyl, 1,3-thiazolyl, 1,2-thiazolyl, 1,3-benzothiazolyl, 2,3-benzothiazolyl, imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl, aminodiphenyl, aminodiphenylether and azobenzenyl which is mono- or poly-substituted by $C_1$–$C_4$alkyl, $C_1$–$C_4$alkoxy, $C_1$–$C_4$alkylthio, halogen, e.g. fluorine, bromine or chlorine, nitro, trifluoromethyl, CN, SCN, $C_1$–$C_4$alkylsulfonyl, phenylsulfonyl, benzylsulfonyl, di-$C_1$–$C_4$alkylaminosulfonyl, $C_1$–$C_4$alkyl-carbonylamino, $C_1$–$C_4$alkoxysulfonyl or by di-(hydroxy-$C_1$–$C_4$alkyl)-aminosulfonyl, R is a radical of formula $-NR_{16}R_{17}$, wherein $R_{16}$ is H; unsubstituted linear or branched $C_1$–$C_6$alkyl or linear or branched $C_1$–$C_6$alkyl, which is substituted by one or more identical or different substituent selected from the group consisting of $OC_1$–$C_4$alkyl, COOH, $COOC_1$–$C_2$alkyl, $SO_3H$, $NH_2$, CN, halogen and OH, and $R_{17}$ is unsubstituted linear or branched $C_1$–$C_6$alkyl or linear or branched $C_1$–$C_6$alkyl, which is substituted by one or more identical or different substituent selected from the group consisting of $OC_1$–$C_4$alkyl, COOH, $COOC_1$–$C_2$alkyl, $SO_3H$, $NH_2$, CN, halogen and OH, T is a linear or branched $C_1$–$C_6$alkyl, which is substituted by one or two identical or different substituent selected from the group consisting of COOH, $SO_3H$, $NH_2$, $NH(C_1$–$C_2$alkyl) and $N(C_1$–$C_2$alkyl)_2$, or T is unsubstituted phenyl; unsubstituted naphthyl; phenyl or naphthyl, which are substituted by one or more identical or different substituents selected from the group consisting of $OC_1$–$C_4$alkyl, COOH, $COOC_1$–$C_2$alkyl, $SO_3H$, $NH_2$, $NH(C_1$–$C_2$alkyl), $N(C_1$–$C_2$alkyl)$_2$, CN, halogen and OH, and b) at least one water-soluble coupling component under conditions such that, initially, coupling does not take place, and then causing the capped diazonium compound present on the material to react with the coupling component, with the same provisos (i)–(x) as defined above.

An especially preferred embodiment of the present invention is a method of colouring porous material, which comprises applying to the material being coloured, in any desired order successively, or simultaneously, a) at least one capped diazonium compound of formula (1)

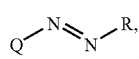
(1)

wherein

Q is an unsubstituted phenyl; naphthyl; thiophenyl; 1,3-thiazolyl; 1,2-thiazolyl; 1,3-benzothiazolyl; 2,3-benzothiazolyl; imidazolyl; 1,3,4-thiadiazolyl; 1,3,5-thiadiazolyl; 1,3,4-triazolyl; pyrazolyl; benzimidazolyl; benzopyrazolyl; pyridinyl; quinolinyl; pyrimidinyl; isoxazolyl; aminodiphenyl; aminodiphenylether and azobenzenyl or Q is a phenyl, naphthyl, thiophenyl, 1,3-thiazolyl, 1,2-thiazolyl, 1,3-benzothiazolyl, 2,3-benzothiazolyl, Imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl, aminodiphenyl, aminodiphenylether and azobenzenyl which is mono- or poly-substituted by $C_1$–$C_4$alkyl, $C_1$–$C_4$alkoxy, $C_1$–$C_4$alkylthio, halogen, e.g. fluorine, bromine or chlorine, nitro, trifluoromethyl, CN, SCN, $C_1$–$C_4$alkylsulfonyl, phenylsulfonyl, benzylsulfonyl, di-$C_1$–$C_4$alkylaminosulfonyl, $C_1$–$C_4$alkyl-carbonylamino, $C_1$–$C_4$alkoxysulfonyl or by di-(hydroxy-$C_1$–$C_4$alkyl)-aminosulfonyl, R is a radical of formula —$NR_{16}R_{17}$, wherein $R_{16}$ is H; unsubstituted linear or branched $C_1$–$C_6$alkyl or linear or branched $C_1$–$C_6$alkyl, which is substituted by one or more identical or different substituent selected from the group consisting of $OC_1$–$C_4$alkyl, COOH, $COOC_1$–$C_2$alkyl, $SO_3H$, $NH_2$, CN, halogen and OH, and $R_{17}$ is unsubstituted linear or branched $C_1$–$C_6$alkyl or linear or branched $C_1$–$C_6$alkyl, which is substituted by one or more identical or different substituent selected from the group consisting of $OC_1$–$C_4$alkyl, COOH, $COOC_1$–$C_2$alkyl, $SO_3H$, $NH_2$, CN, halogen and OH, and b) at least one water-soluble coupling component under conditions such that, initially, coupling does not take place, and then causing the capped diazonium compound present on the material to react with the coupling component, with the same provisos (i)–(x) as defined above.

A further especially preferred embodiment of the present invention is a method of colouring porous material, which comprises applying to the material being coloured, in any desired order successively, or simultaneously, a) at least one capped diazonium compound of formula (1)

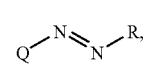
(1)

wherein

Q is an unsubstituted phenyl; naphthyl; thiophenyl; 1,3-thiazolyl; 1,2-thiazolyl; 1,3-benzothiazolyl; 2,3-benzothiazolyl; imidazolyl; 1,3,4-thiadiazolyl; 1,3,5-thiadiazolyl; 1,3,4-triazolyl; pyrazolyl; benzimidazolyl; benzopyrazolyl; pyridinyl; quinolinyl; pyrimidinyl; isoxazolyl; aminodiphenyl; aminodiphenylether and azobenzenyl or Q is a phenyl, naphthyl, thiophenyl, 1,3-thiazolyl, 1,2-thiazolyl, 1,3-benzothiazolyl, 2,3-benzothiazolyl, imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl, aminodiphenyl, aminodiphenylether and azobenzenyl which is mono- or poly-substituted by $C_1$–$C_4$alkyl, $C_1$–$C_4$alkoxy, $C_1$–$C_4$alkylthio, halogen, e.g. fluorine, bromine or chlorine, nitro, trifluoromethyl, CN, SCN, $C_1$–$C_4$alkylsulfonyl, phenylsulfonyl, benzylsulfonyl, di-$C_1$–$C_4$alkylaminosulfonyl, $C_1$–$C_4$alkyl-carbonylamino, $C_1$–$C_4$alkoxysulfonyl or by di-(hydroxy-$C_1$–$C_4$alkyl)-aminosulfonyl, R is a radical of formula —$NR_{16}R_{17}$, wherein $R_{16}$ is H; unsubstituted linear or branched $C_1$–$C_6$alkyl or linear or branched $C_1$–$C_6$alkyl, which is substituted by one or more identical or different substituent selected from the group consisting of $OC_1$–$C_4$alkyl, COOH, $COOC_1$–$C_2$alkyl, $SO_3H$, $NH_2$, CN, halogen and OH, and $R_{17}$ is unsubstituted linear or branched $C_1$–$C_6$alkyl or linear or branched $C_1$–$C_6$alkyl, which is substituted by one or more identical or different substituent selected from the group consisting of $OC_1$–$C_4$alkyl, COOH, $COOC_1$–$C_2$alkyl, $SO_3H$, $NH_2$, CN, halogen and OH, and b) at least one water-soluble coupling component under conditions such that, initially, coupling does not take place, and then causing the capped diazonium compound present on the material to react with the coupling component, with the provisos that if the capped diazonium compound is

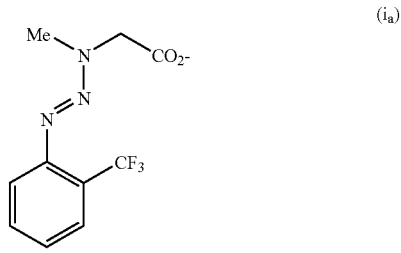
($i_a$)

then the water-soluble coupling component is not
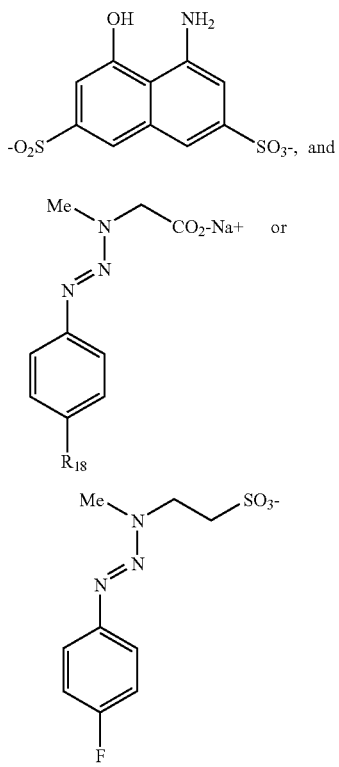
(ii_a)
wherein R_18 signifies H, CH_3, F, NO_2, OCH_3
then water-soluble coupling component is not
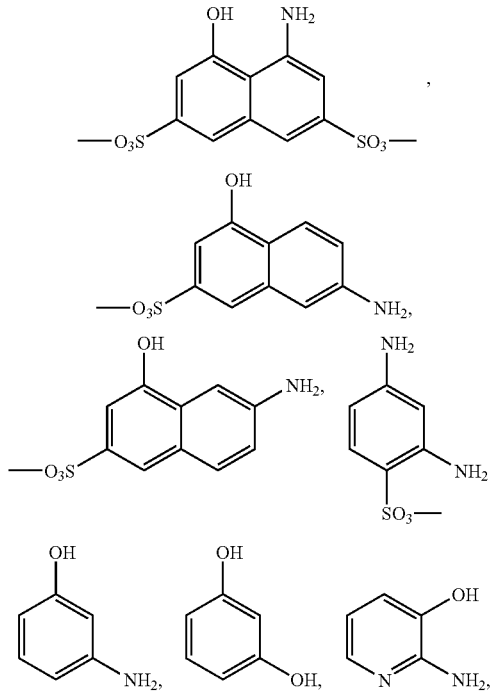
-continued
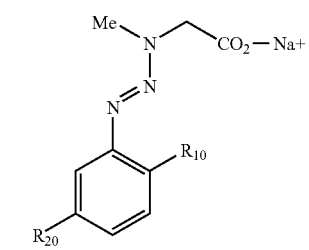
(iii_a)
wherein R_19 signifies OCH_3, CH_3 and
R_20 signifies Cl, CH_3, NO_2, NHCOCH_3
then water-soluble coupling component is not
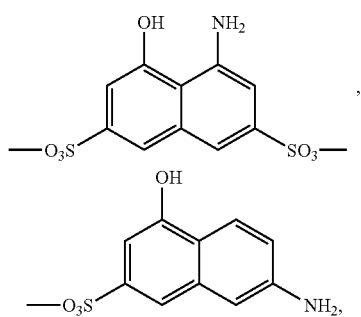

-continued
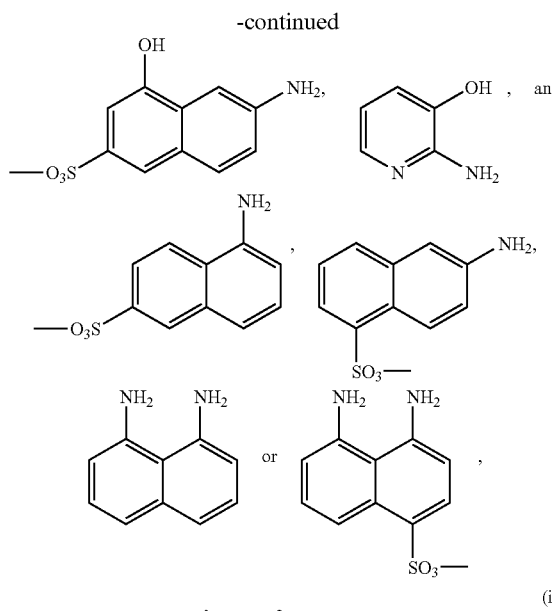
(iv_a)
wherein R_{21} signifies Cl, CH$_3$, SO$_3^-$, OCH$_3$
R_{22} signifies CH$_3$, Cl, OCH$_3$
then the water-soluble coupling component is not
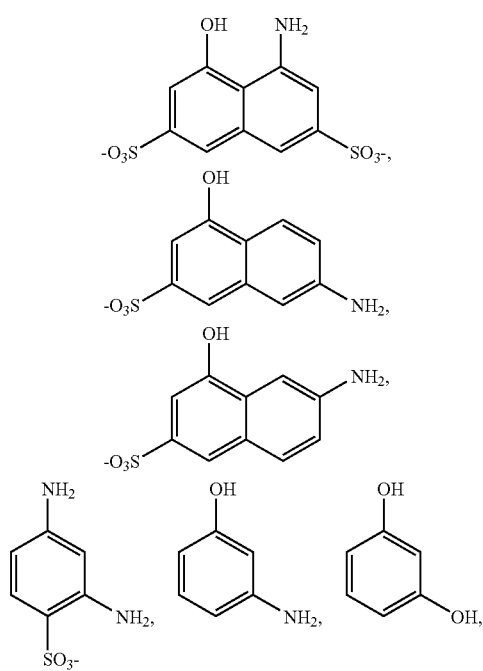
-continued
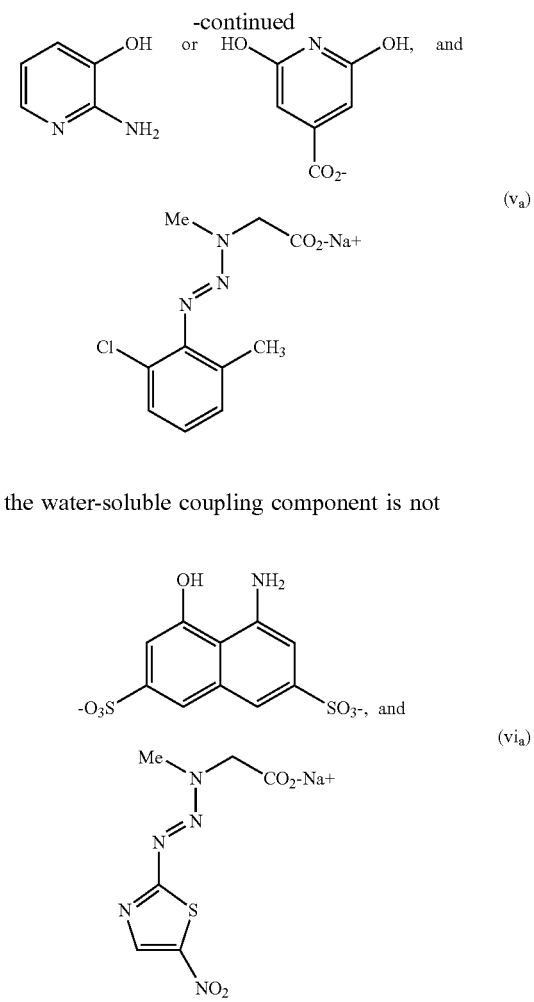
(v_a)
then the water-soluble coupling component is not
(vi_a)
then the water-soluble coupling component is not
(vii_a)
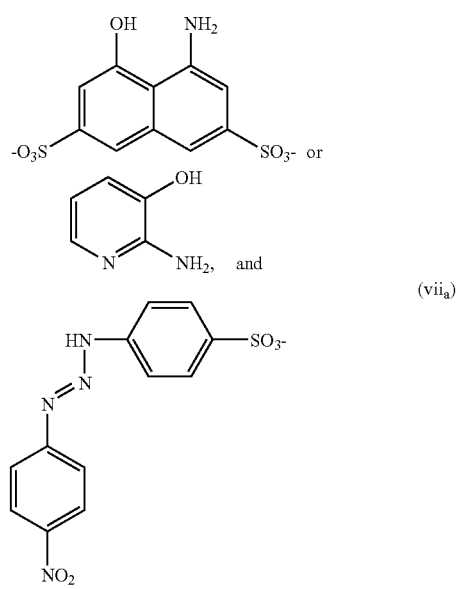

then the water-soluble coupling component is not

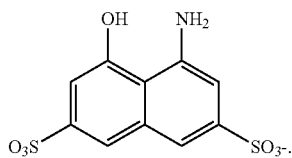

A further embodiment of the present invention is a method of colouring porous material, which comprises applying to the material being coloured, in any desired order successively, or simultaneously,
a) at least two capped diazonium compounds as defined above and
b) at least one water-soluble coupling component under conditions such that, initially, coupling does not take place, and then causing the capped diazonium compound present on the material to react with the coupling component.

A further embodiment of the present invention is a method of colouring porous material, which comprises applying to the material being coloured, in any desired order successively, or simultaneously,
a) at least one capped diazonium compound as defined above and
b) at least two water-soluble coupling components under conditions such that, initially, coupling does not take place, and then causing the capped diazonium compound present on the material to react with the coupling component.

A further embodiment of the present invention is a method of colouring porous material, which comprises applying to the material being coloured, in any desired order successively, or simultaneously,
a) at least two capped diazonium compounds as defined above and
b) at least two water-soluble coupling components under conditions such that, initially, coupling does not take place, and then causing the capped diazonium compound present on the material to react with the coupling component.

Suitable coupling components are, for example, the usual coupling components customarily used for azo dyes and known from the pertinent literature, e.g. coupling components from the benzene series, naphthalene series, open-chain methylene-active compounds (e.g. acylacetarylamides) and the heterocyclic series.

They are, for example, acylacetarylamides, phenols, naphthols, pyridones, quinolones, pyrazoles, indoles, diphenylamines, anilines, aminopyridines, pyrimidones, naphthylamines, aminothiazoles, thiophenes or hydroxypyridines.

Acetoacetanilides, phenols, anilines, diphenylamines, naphthylamines, indoles, quinolines, pyridones, pyrazoles and aminopyridines are especially suitable.

Such coupling components may carry further substituents, for example amino, alkylamino, dialkylamino, halogen, alkyl, alkoxy, aryl, especially phenyl or naphthyl, or aryloxy, but especially a group imparting water solubility, e.g. hydroxy, carboxy or sulfo.

The coupling components preferably carry one or two such groups imparting water solubility. Examples of suitable coupling components are as follows:

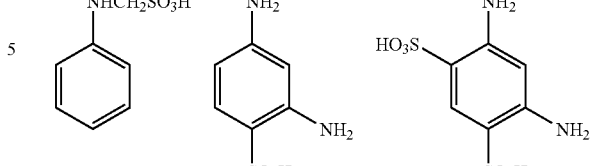

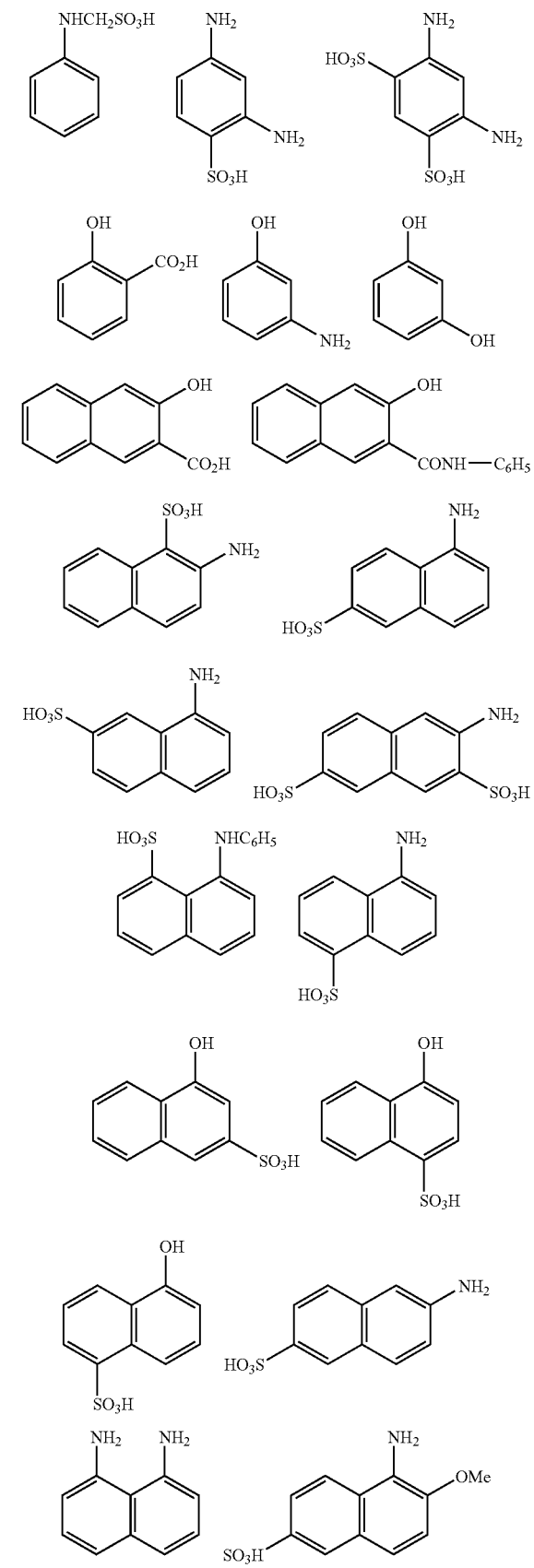

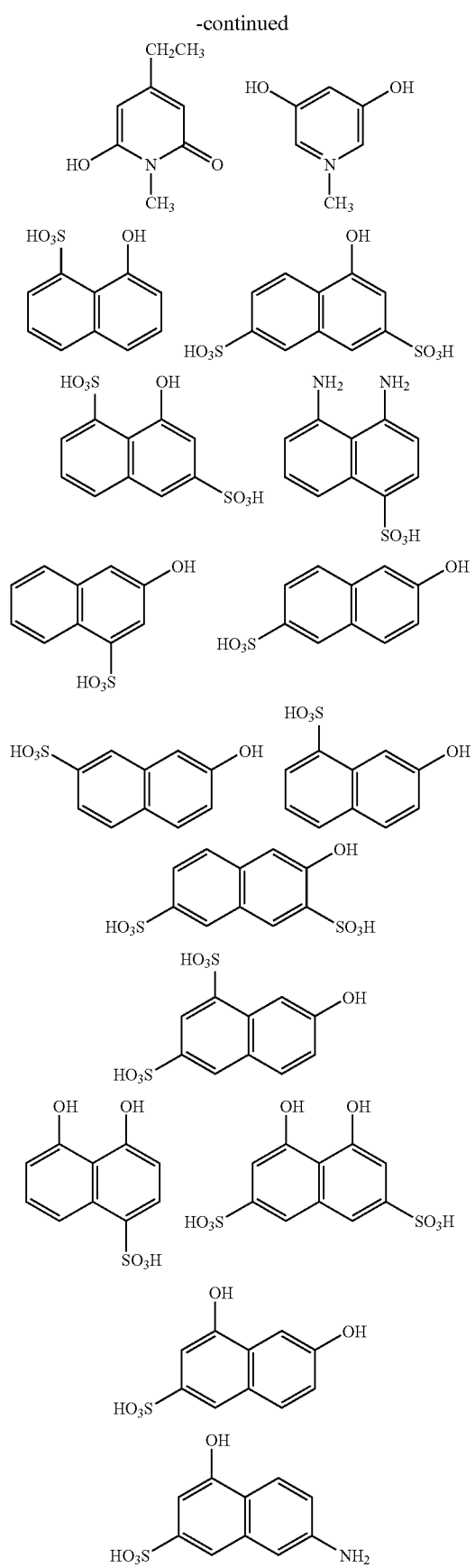
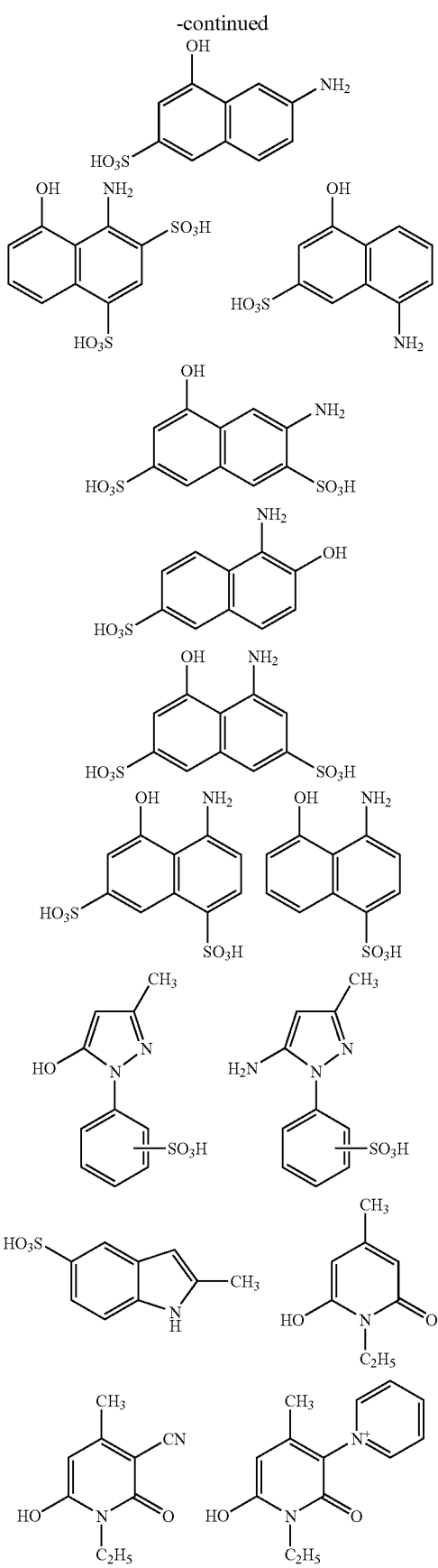

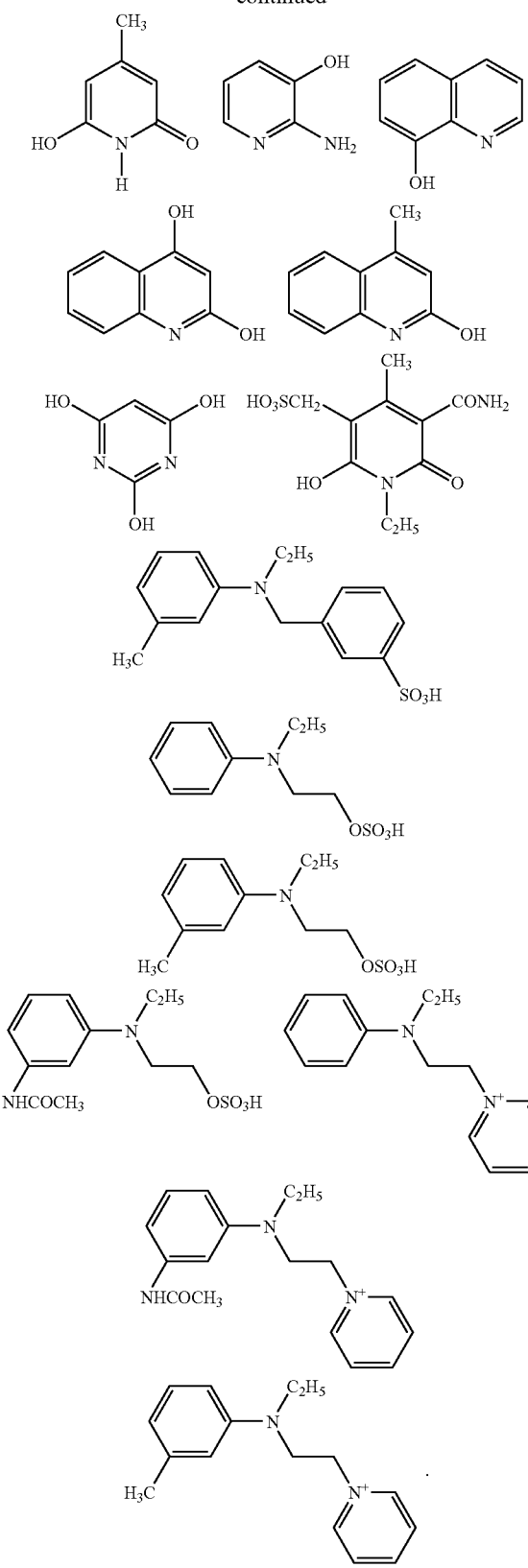

A further embodiment of the present invention is a method of colouring porous material, which comprises applying to the material being coloured, in any desired order successively, or simultaneously, a) at least one capped diazonium compound of formula (1)

(1)

and/or at least one compound of formula (2)

(2)

and/or at least one compound of formula (3)

(3)

wherein

Q is an unsubstituted phenyl; naphthyl; thiophenyl; 1,3-thiazolyl; 1,2-thiazolyl; 1,3-benzothiazolyl; 2,3-benzothiazolyl; imidazolyl; 1,3,4-thiadiazolyl; 1,3,5-thiadiazolyl; 1,3,4-triazolyl; pyrazolyl; benzimidazolyl; benzopyrazolyl; pyridinyl; quinolinyl; pyrimidinyl; isoxazolyl; aminodiphenyl; aminodiphenylether and azobenzenyl or Q is a phenyl, naphthyl, thiophenyl, 1,3-thiazolyl, 1,2-thiazolyl, 1,3-benzothiazolyl, 2,3-benzothiazolyl, imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl, aminodiphenyl, aminodiphenylether and azobenzenyl which is mono- or poly-substituted by $C_1$–$C_4$alkyl, $C_1$–$C_4$alkoxy, $C_1$–$C_4$alkylthio, halogen, e.g. fluorine, bromine or chlorine, nitro, trifluoromethyl, CN, SCN, $C_1$–$C_4$alkylsulfonyl, phenylsulfonyl, benzylsulfonyl, di-$C_1$–$C_4$alkylaminosulfonyl, $C_1$–$C_4$alkyl-carbonylamino, $C_1$–$C_4$alkoxysulfonyl or by di-(hydroxy-$C_1$–$C_4$alkyl)-aminosulfonyl, R is a radical of formula —$NR_{16}R_{17}$, wherein $R_{15}$ is H; unsubstituted linear or branched $C_1$–$C_6$alkyl or linear or branched $C_1$–$C_6$alkyl, which is substituted by one or more identical or different substituent selected from the group consisting of $OC_1$–$C_4$alkyl, COOH, $COOC_1$–$C_2$alkyl, $SO_3H$, $NH_2$, CN, halogen and OH, and $R_{17}$ is unsubstituted linear or branched $C_1$–$C_6$alkyl or linear or branched $C_1$–$C_6$alkyl, which is substituted by one or more identical or different substituent selected from the group consisting of $OC_1$–$C_4$alkyl, COOH, $COOC_1$–$C_2$alkyl, $SO_3H$, $NH_2$, CN, halogen and OH, T is a linear or branched $C_1$–$C_6$alkyl, which is substituted by one or two identical or different substituent selected from the group consisting of COOH, SO₃H, NH₂, NH(C₁–C₂alkyl) and N(C₁–C₂alkyl)₂, or T is unsubstituted phenyl; unsubstituted naphthyl; phenyl or naphthyl, which are substituted by one or more identical or different substituents selected from the group consisting of OC₁–C₄alkyl, COOH, COOC₁–C₂alkyl, SO₃H, NH₂, NH(C₁–C₂alkyl), N(C₁–C₂alkyl)₂, CN, halogen and OH, and b) at least one water-soluble coupling component selected from the group consisting of acylacetarylamides, phenols, naphthols, pyridones, quinolones, pyrazoles, indoles, diphenylamines, anilines, aminopyridines, pyrimidones, naphthylamines, aminothiazoles, thiophenes or hydroxypyridines, which all may carry further substituents, for example amino, alkylamino, dialkylamino, halogen, alkyl, alkoxy, aryl, especially phenyl or naphthyl, or aryloxy, but especially a group imparting water solubility, e.g. hydroxy, carboxy or sulfo, under conditions such that, initially, coupling does not take place, and then causing the capped diazonium compound present on the material to react with the coupling component, with the same provisos (i)–(x) as defined above.

An especially preferred embodiment of the present invention is a method of colouring porous material, which comprises applying to the material being coloured, in any desired order successively, or simultaneously, a) at least one capped diazonium compound of formula (1)

(1)

wherein

Q is an unsubstituted phenyl; naphthyl; thiophenyl; 1,3-thiazolyl; 1,2-thiazolyl; 1,3-benzothiazolyl; 2,3-benzothiazolyl; imidazolyl; 1,3,4-thiadiazolyl; 1,3,5-thiadiazolyl; 1,3,4-triazolyl; pyrazolyl; benzimidazolyl; benzopyrazolyl; pyridinyl; quinolinyl; pyrimidinyl; isoxazolyl; aminodiphenyl; aminodiphenylether and azobenzenyl or Q is a phenyl, naphthyl, thiophenyl, 1,3-thiazolyl, 1,2-thiazolyl, 1,3-benzothiazolyl, 2,3-benzothiazolyl, imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl, aminodiphenyl, aminodiphenylether and azobenzenyl which is mono- or poly-substituted by C₁–C₄alkyl, C₁–C₄alkoxy, C₁–C₄alkylthio, halogen, e.g. fluorine, bromine or chlorine, nitro, trifluoromethyl, CN, SCN, C₁–C₄alkylsulfonyl, phenylsulfonyl, benzylsulfonyl, di-C₁–C₄alkylaminosulfonyl, C₁–C₄alkyl-carbonylamino, C₁–C₄alkoxysulfonyl or by di-(hydroxy-C₁–C₄alkyl)-aminosulfonyl, R is a radical of formula —NR₁₆R₁₇, wherein R₁₆ is H; unsubstituted linear or branched C₁–C₆alkyl or linear or branched C₁–C₆alkyl, which is substituted by one or more identical or different substituent selected from the group consisting of OC₁–C₄alkyl, COOH, COOC₁–C₂alkyl, SO₃H, NH₂, CN, halogen and OH, and R₁₇ is unsubstituted linear or branched C₁–C₆alkyl or linear or branched C₁–C₆alkyl, which is substituted by one or more identical or different substituent selected from the group consisting of OC₁–C₄alkyl, COOH, COOC₁–C₂alkyl, SO₃H, NH₂, CN, halogen and OH, and b) at least one water-soluble coupling component selected from the group consisting of

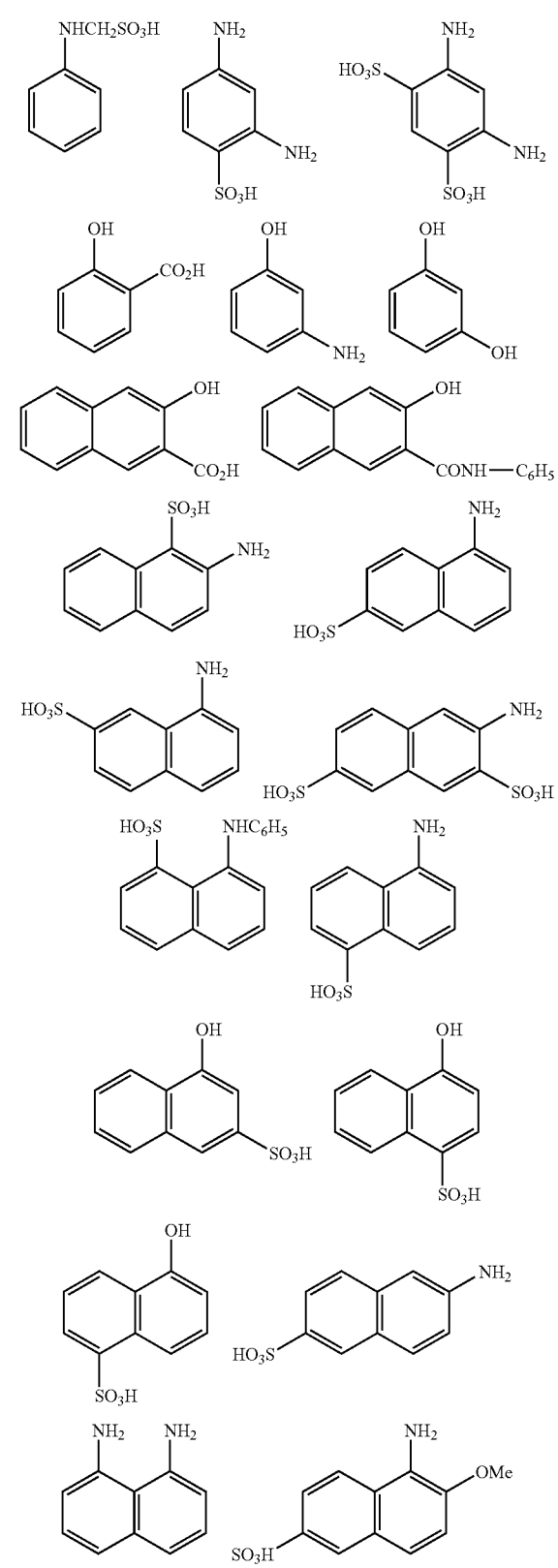

-continued
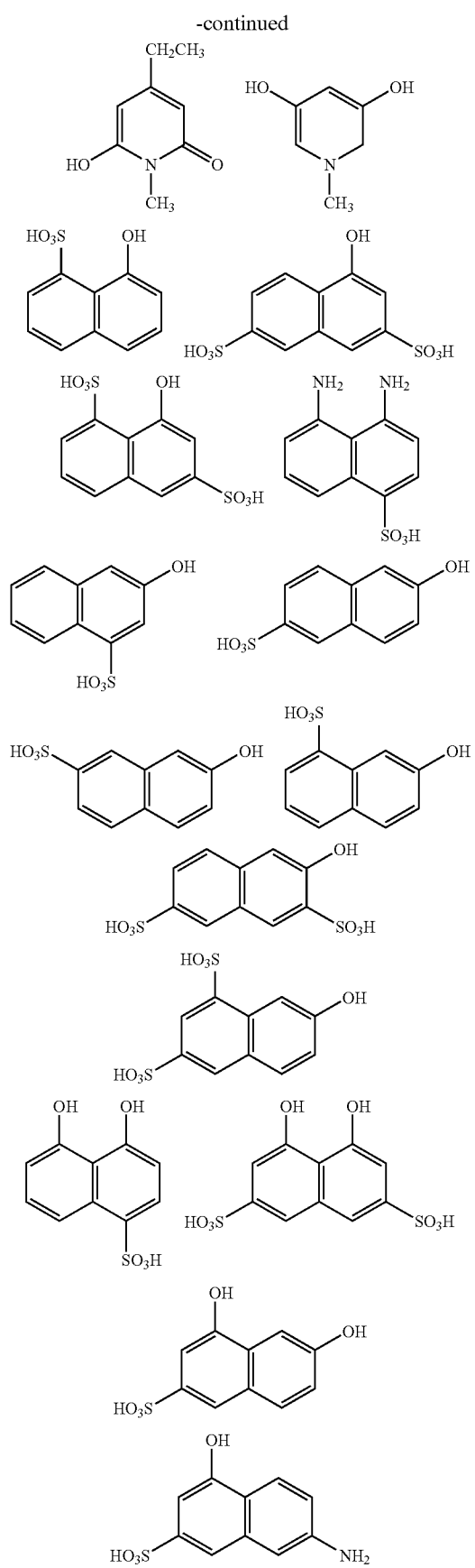
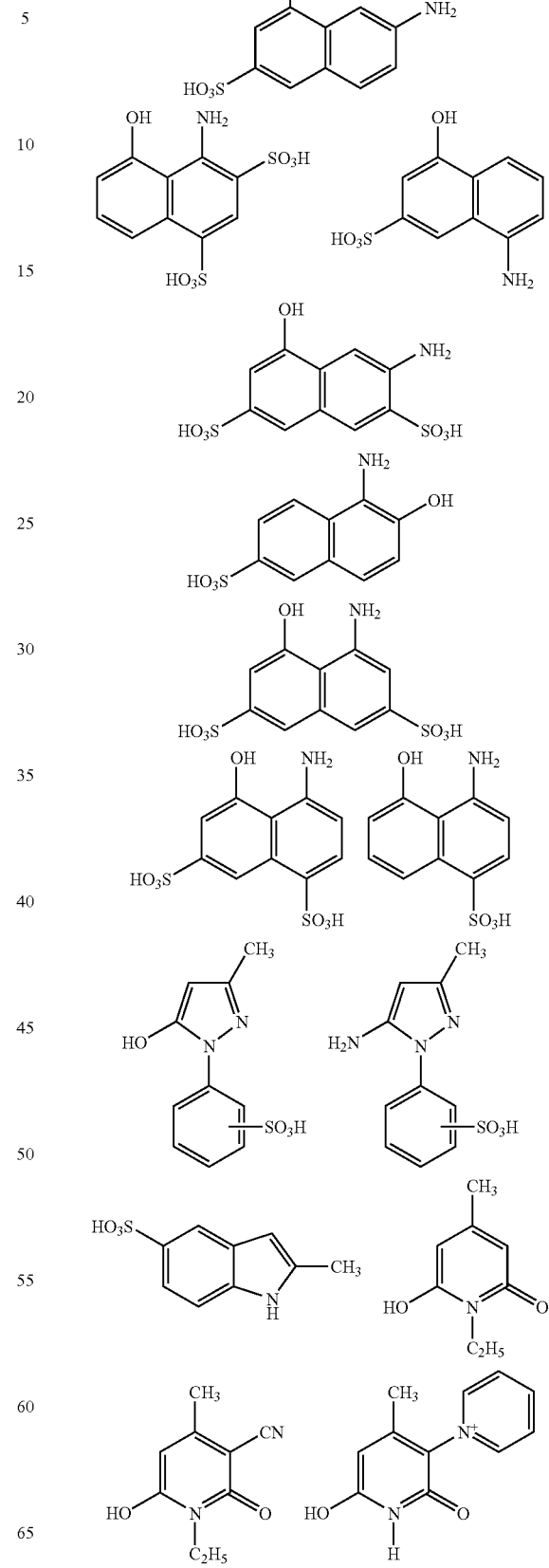

-continued

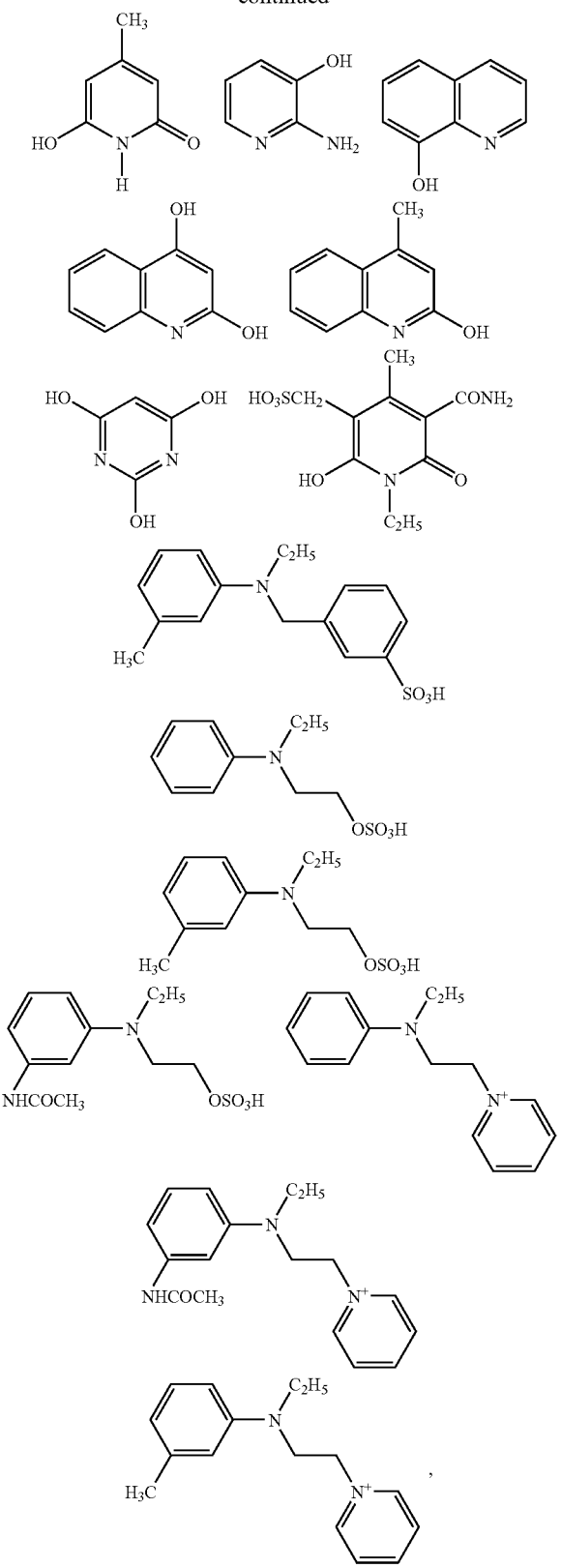

under conditions such that, initially, coupling does not take place, and then causing the capped diazonium compound present on the material to react with the coupling component, with the same provisos (i)–(x) as defined above.

An especially preferred embodiment of the present invention is a method of colouring porous material, which comprises applying to the material being coloured, in any desired order successively, or simultaneously, a) at least one capped diazonium compound of formula (1)

(1)

wherein

Q is an unsubstituted phenyl; naphthyl; thiophenyl; 1,3-thiazolyl; 1,2-thiazolyl; 1,3-benzothiazolyl; 2,3-benzothiazolyl; imidazolyl; 1,3,4-thiadiazolyl; 1,3,5-thiadiazolyl; 1,3,4-triazolyl; pyrazolyl; benzimidazolyl; benzopyrazolyl; pyridinyl; quinolinyl; pyrimidinyl; isoxazolyl; aminodiphenyl; aminodiphenylether and azobenzenyl or Q is a phenyl, naphthyl, thiophenyl, 1,3-thiazolyl, 1,2-thiazolyl, 1,3-benzothiazolyl, 2,3-benzothiazolyl, imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl, aminodiphenyl, aminodiphenylether and azobenzenyl which is mono- or poly-substituted by $C_1$–$C_4$alkyl, $C_1$–$C_4$alkoxy, $C_1$–$C_4$alkylthio, halogen, e.g. fluorine, bromine or chlorine, nitro, trifluoromethyl, CN, SCN, $C_1$–$C_4$alkylsulfonyl, phenylsulfonyl, benzylsulfonyl, di-$C_1$–$C_4$alkylaminosulfonyl, $C_1$–$C_4$alkyl-carbonylamino, $C_1$–$C_4$alkoxysulfonyl or by di-(hydroxy-$C_1$–$C_4$alkyl)-aminosulfonyl, R is a radical of formula —$NR_{16}R_{17}$, wherein $R_{16}$ is H; unsubstituted linear or branched $C_1$–$C_6$alkyl or linear or branched $C_1$–$C_6$alkyl, which is substituted by one or more identical or different substituent selected from the group consisting of $OC_1$–$C_4$alkyl, COOH, $COOC_1$–$C_2$alkyl, $SO_3H$, $NH_2$, CN, halogen and OH, and $R_{17}$ is unsubstituted linear or branched $C_1$–$C_6$alkyl or linear or branched $C_1$–$C_6$alkyl, which is substituted by one or more identical or different substituent selected from the group consisting of $OC_1$–$C_4$alkyl, COOH, $COOC_1$–$C_2$alkyl, $SO_3H$, $NH_2$, CN, halogen and OH, and b) at least one water-soluble coupling component selected from the group consisting of

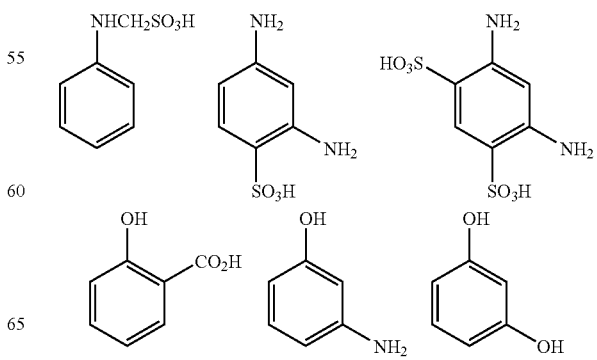

-continued
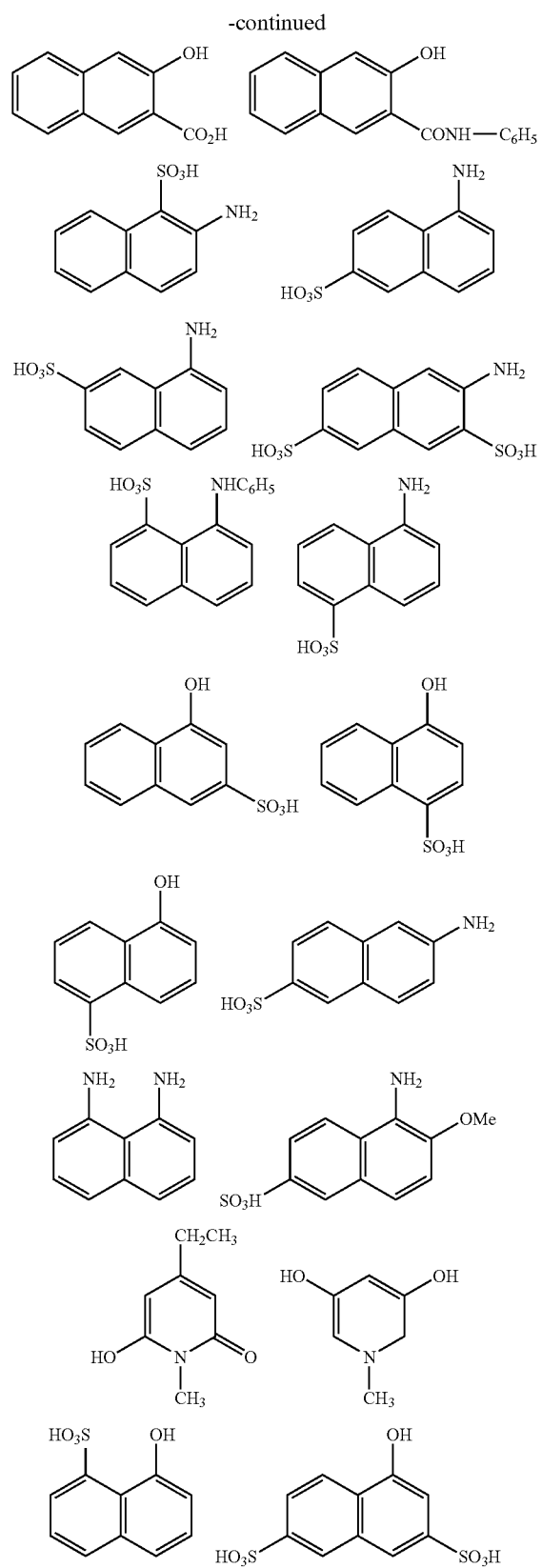
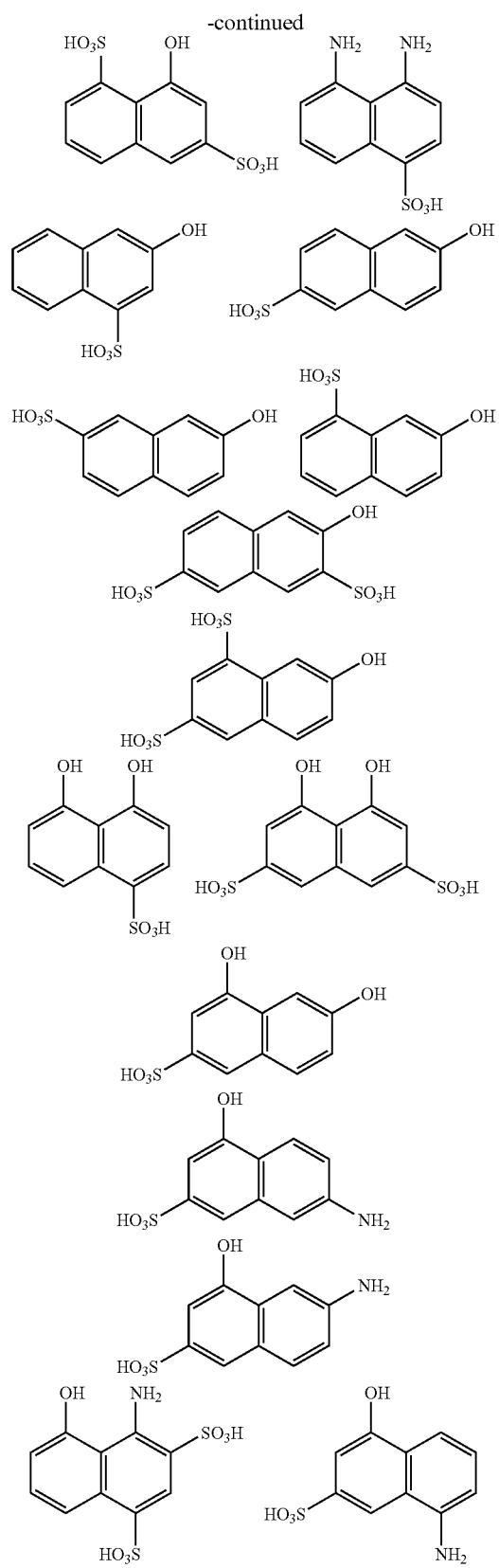

-continued

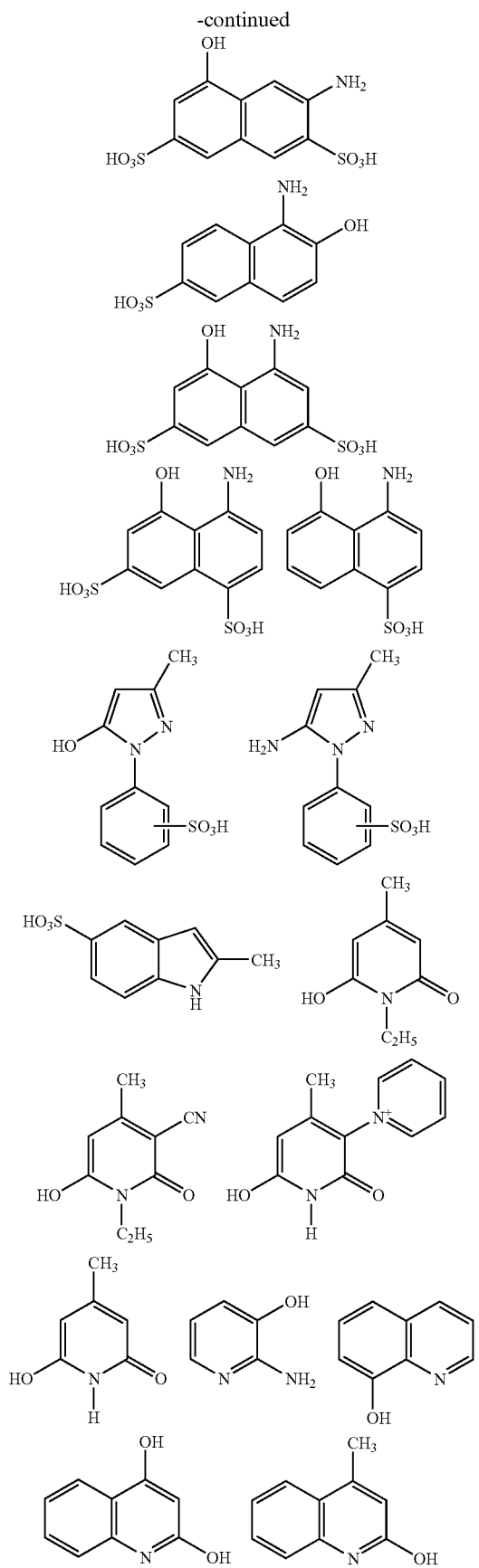

-continued

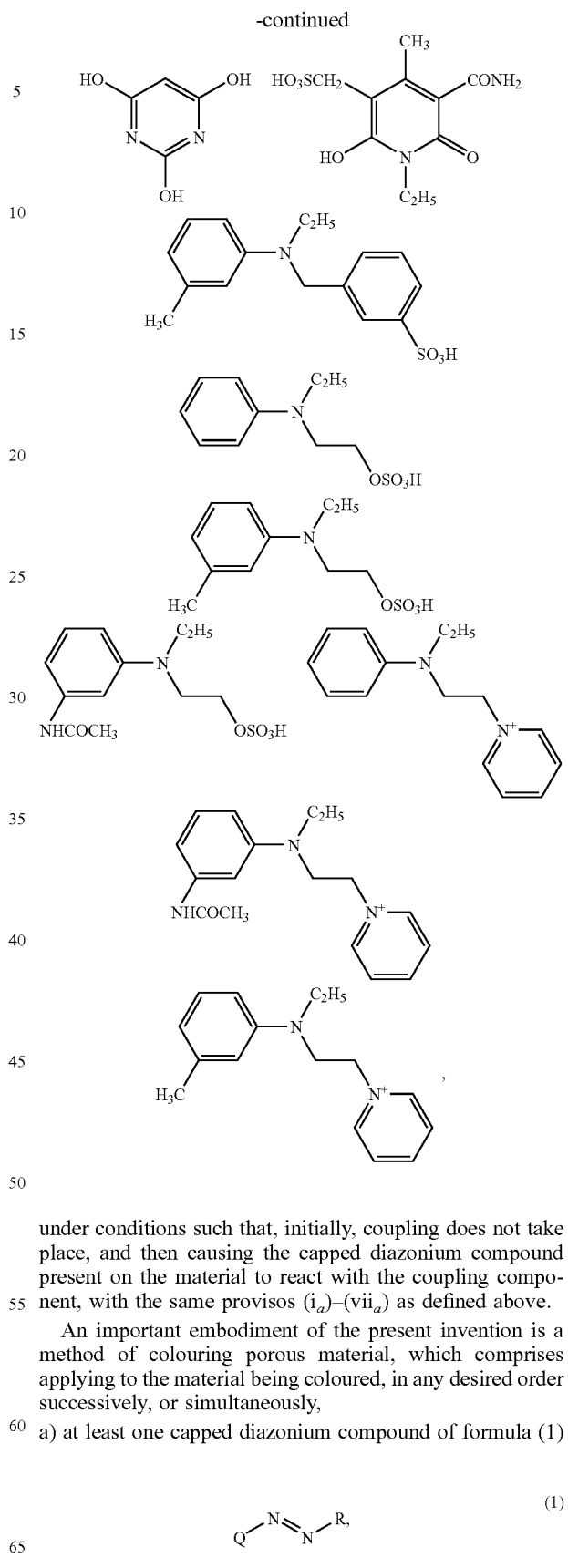

under conditions such that, initially, coupling does not take place, and then causing the capped diazonium compound present on the material to react with the coupling component, with the same provisos ($i_a$)–($vii_a$) as defined above.

An important embodiment of the present invention is a method of colouring porous material, which comprises applying to the material being coloured, in any desired order successively, or simultaneously, a) at least one capped diazonium compound of formula (1)

(1)

and/or at least one compound of formula (2)
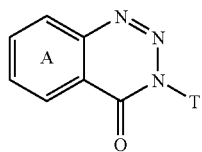
(2)
and/or at least one compound of formula (3)
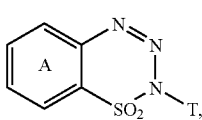
(3)
wherein
Q is
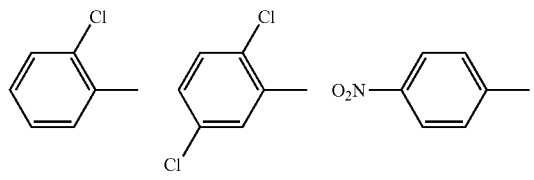
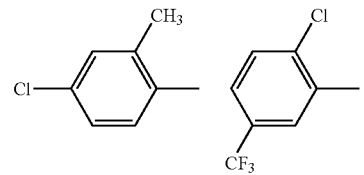
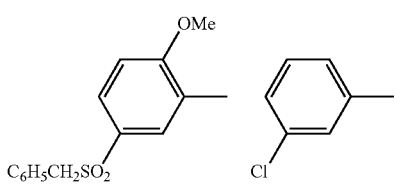
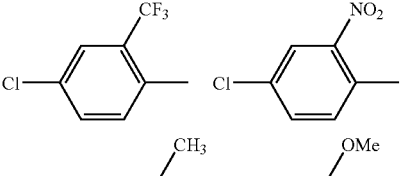
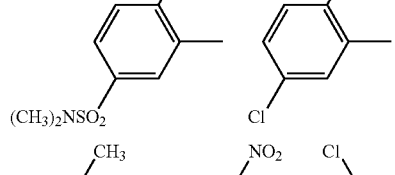
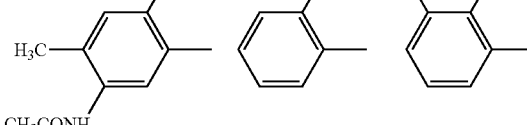
-continued
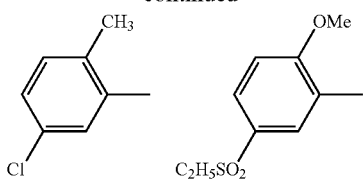
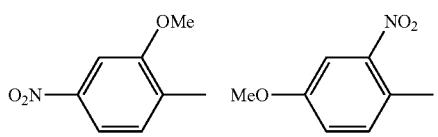
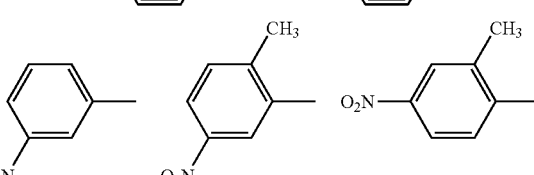
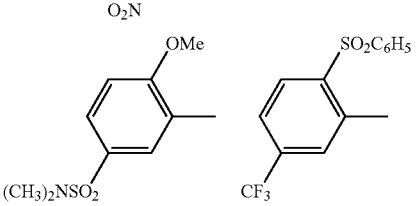
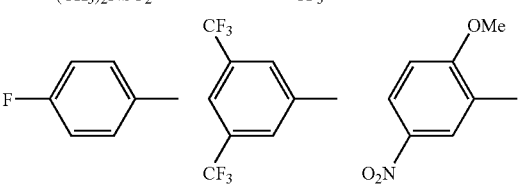
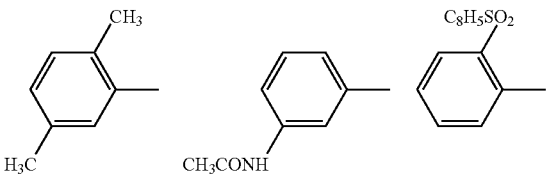
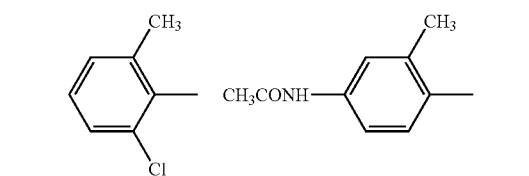
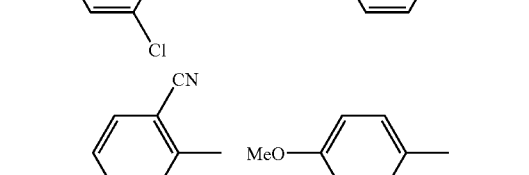
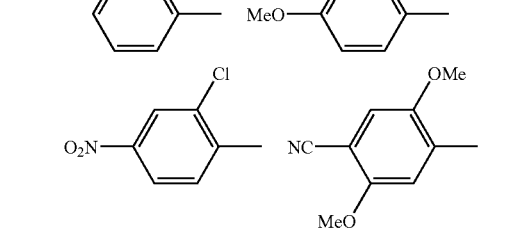

-continued
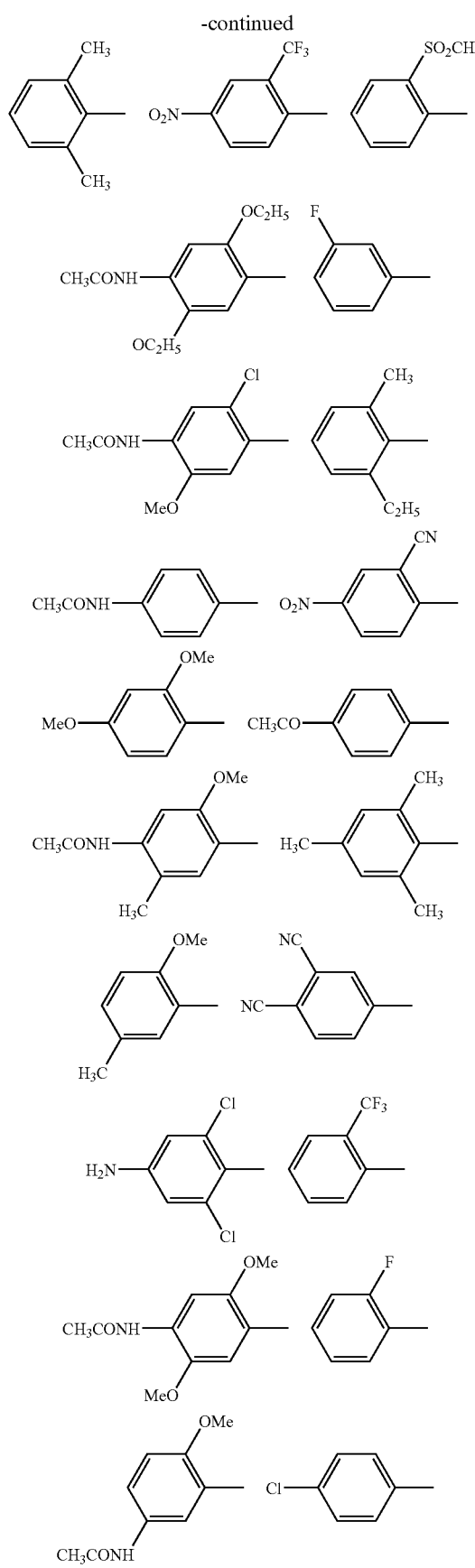
-continued
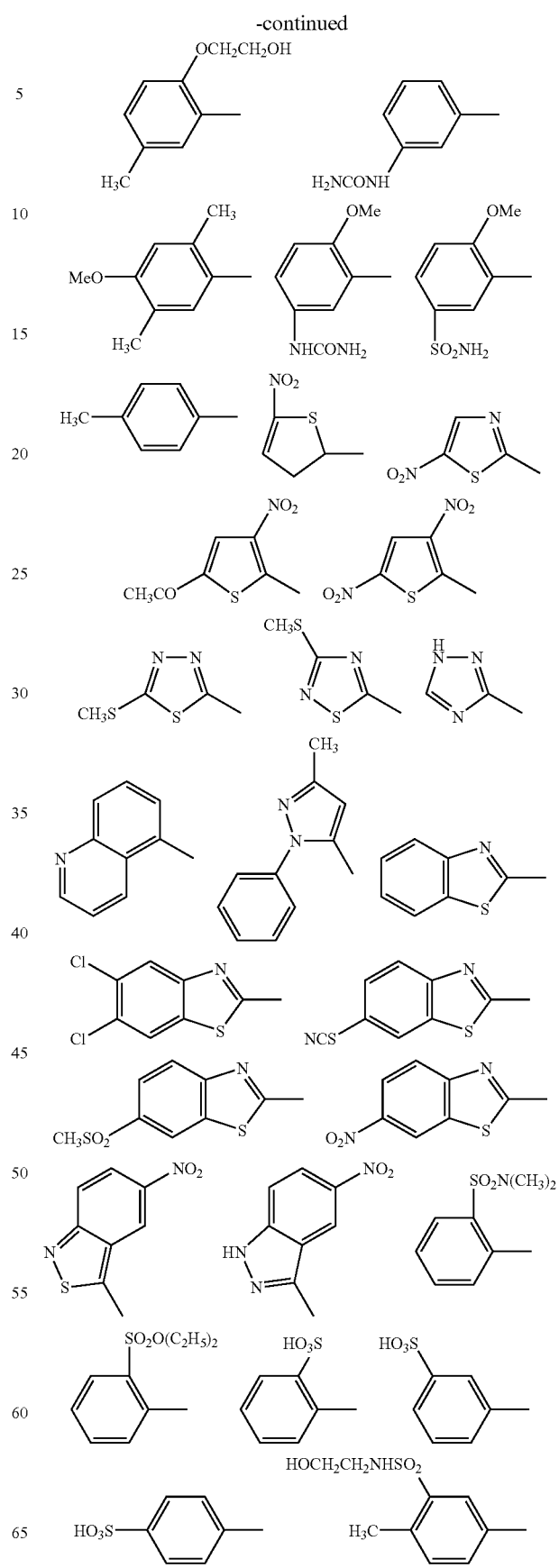

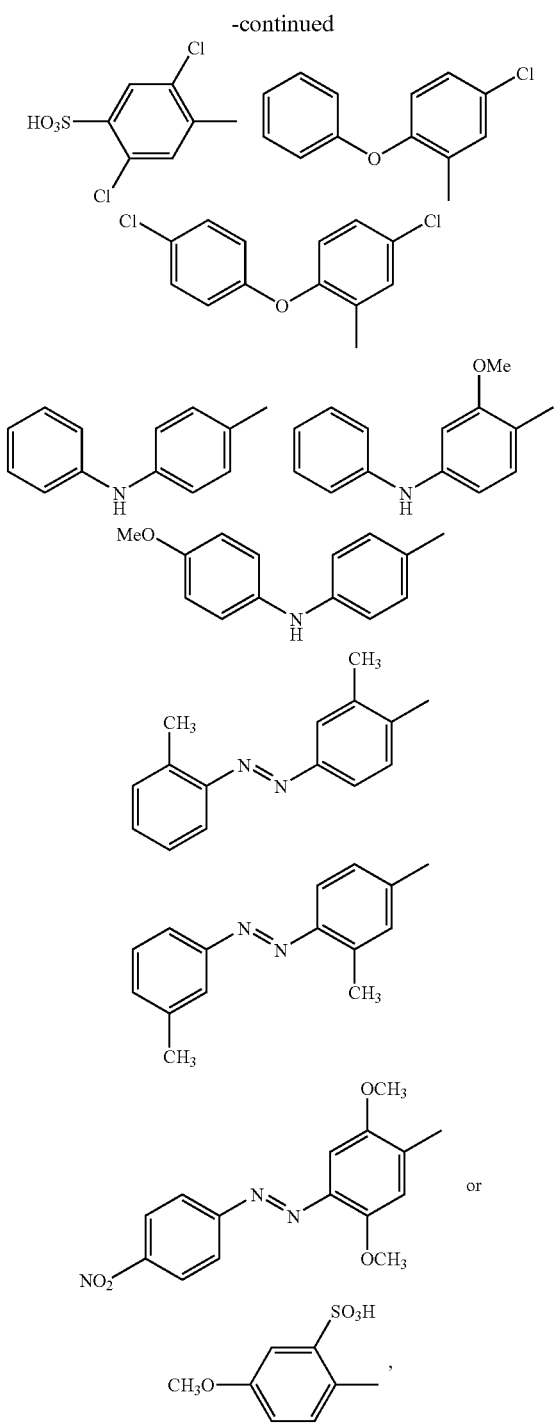
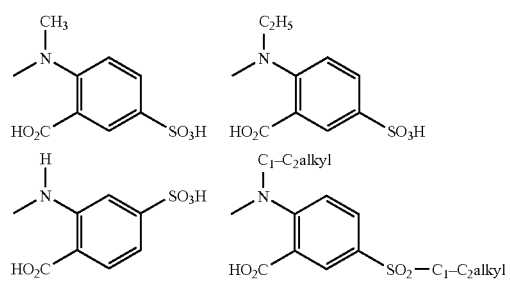
R is
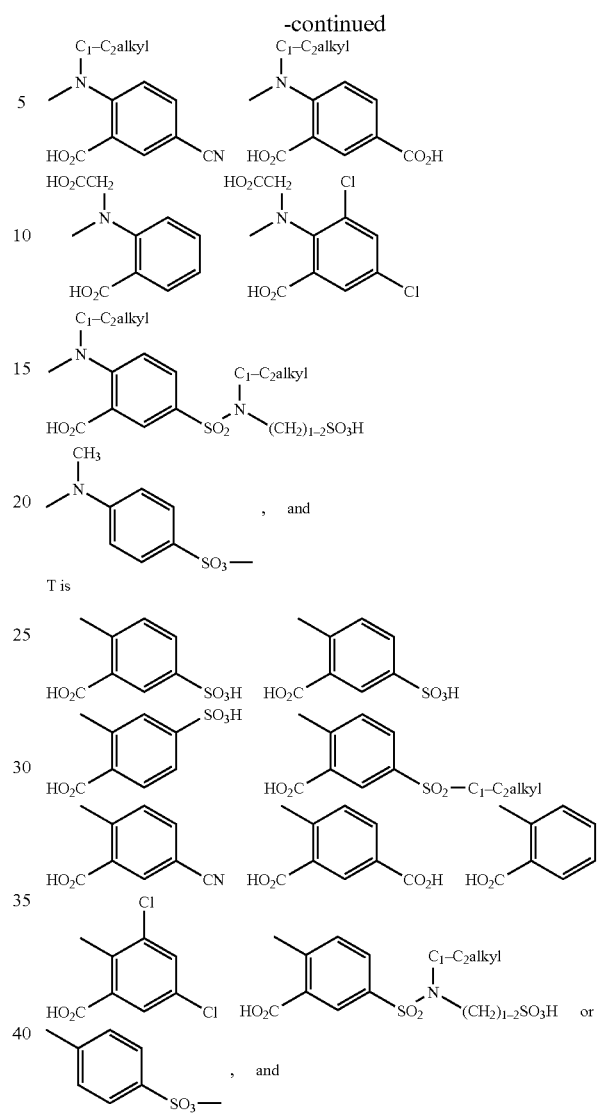
T is
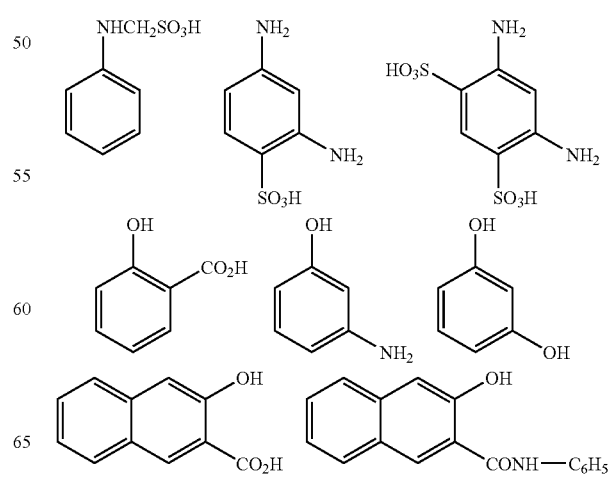
b) at least one water-soluble coupling component selected from the group consisting of -continued
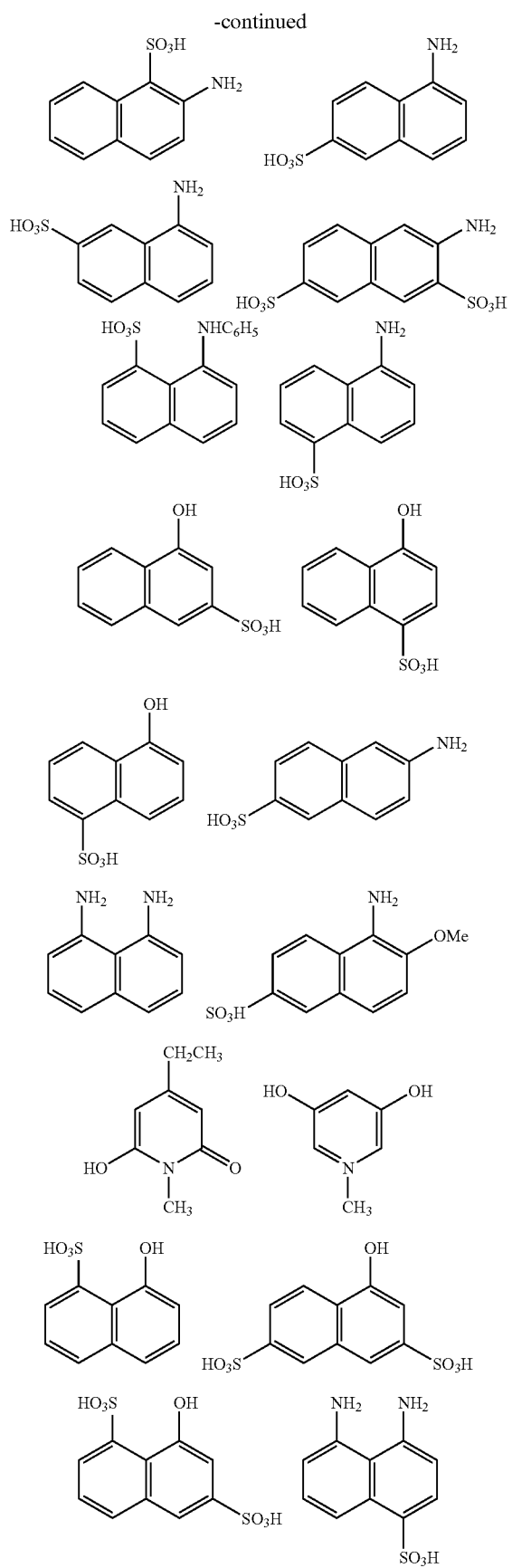
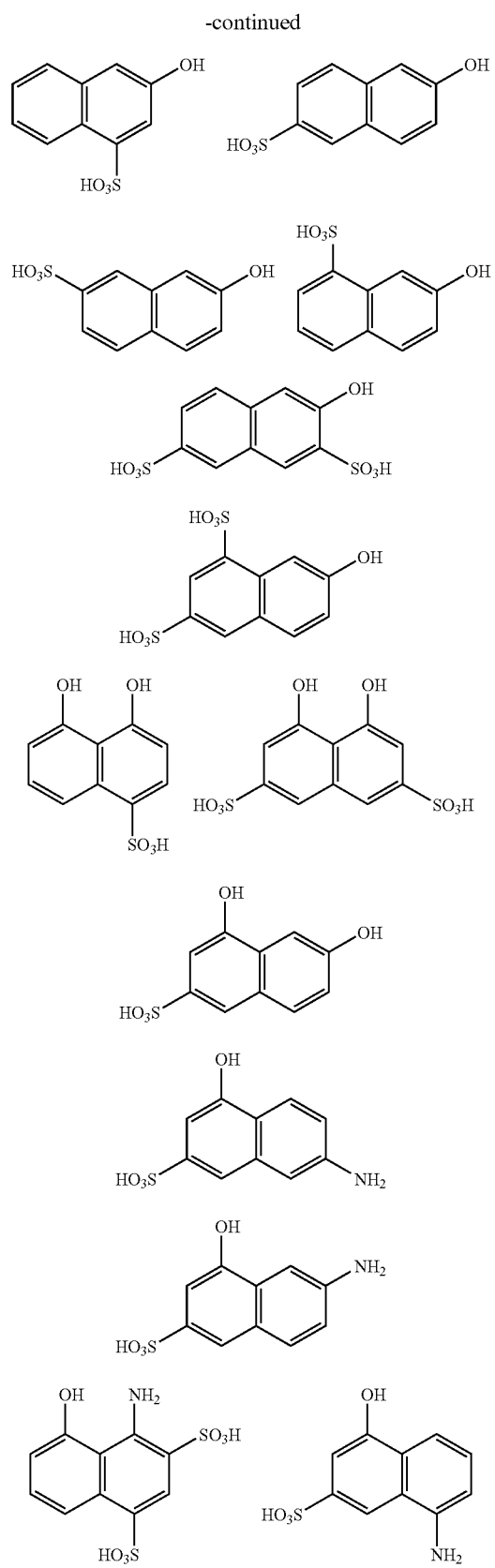

-continued

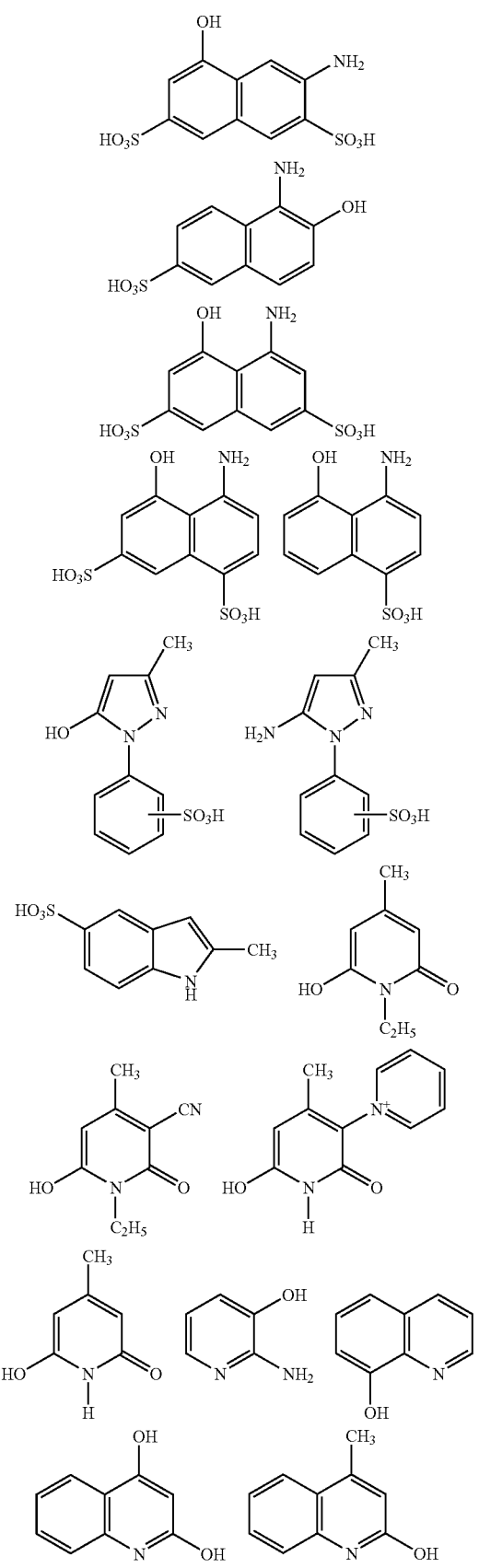

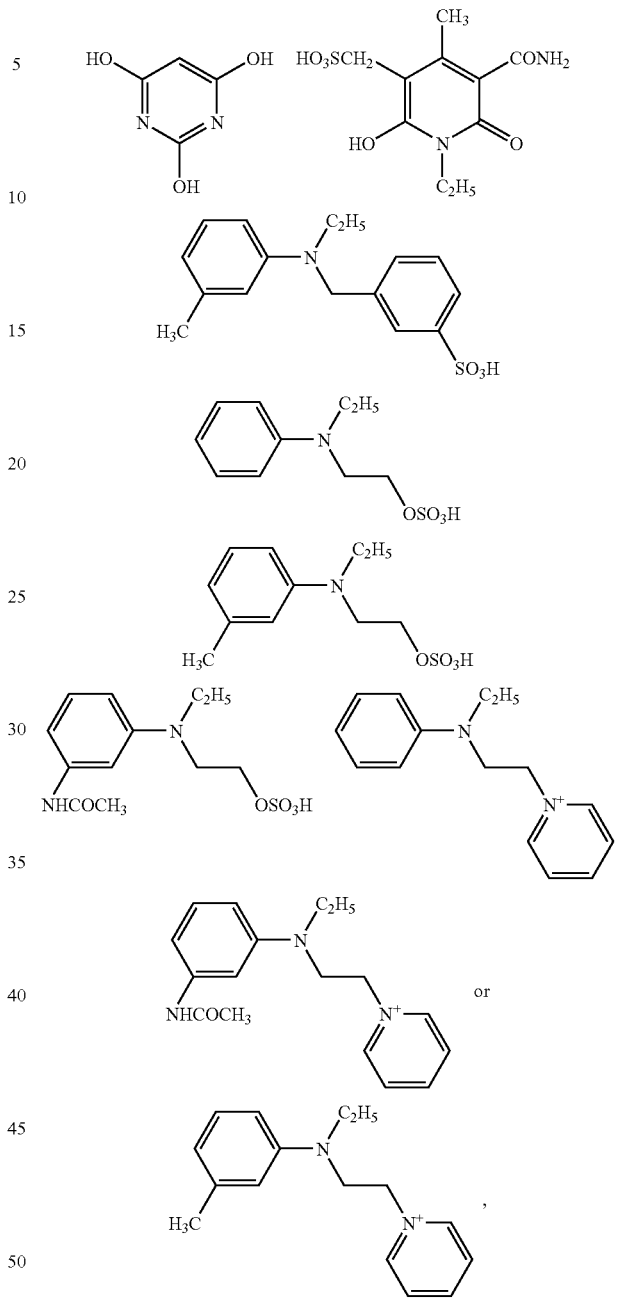

under conditions such that, initially, coupling does not take place, and then causing the capped diazonium compound present on the material to react with the coupling component, with the same provisos (i)–(x) as defined above.

The amines of formulae Q-NH$_2$ and R—H and the coupling components are known or can be synthesised in a manner known per se.

The compounds of formulae (2) and (3) are also known or can be synthesised in a manner known per se.

The compounds of formula (1) wherein R is the radical of an aliphatic amine are likewise known or can be synthesised in a manner known per se.

The compounds of formula

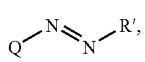 (4)

wherein

Q is an unsubstituted or substituted phenyl, naphthyl, thiophenyl, 1,3-thiazolyl, 1,2-thiazolyl, 1,3-benzothiazolyl, 2,3-benzothiazolyl, imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl, aminodiphenyl, aminodiphenylether or azobenzenyl or Q is phenyl, naphthyl, thiophenyl, 1,3-thiazolyl, 1,2-thiazolyl, 1,3-benzothiazolyl, 2,3-benzothiazolyl, imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl, aminodiphenyl, aminodiphenylether or azobenzenyl mono- or polysubstituted by $C_1$–$C_4$alkyl, $C_1$–$C_4$alkoxy, $C_1$–$C_4$alkylthio, halogen, e.g. fluorine, bromine or chlorine, nitro, trifluoromethyl, CN, SCN, $C_1$–$C_4$alkylsulfonyl, phenylsulfonyl, benzylsulfonyl, di-$C_1$–$C_4$alkylaminosulfonyl, $C_1$–$C_4$alkylcarbonylamino, $C_1$–$C_4$alkoxysulfonyl or by di-(hydroxy-$C_1$–$C_4$alkyl)-aminosulfonyl, and R' is the radical of unsubstituted aniline; the radical of unsubstituted aminonaphthalene; the radical of aniline or aminonaphthalene, wherein the phenyl or the naphthyl ring is substituted by one or more identical or different substituent selected from the group consisting of COOH, $SO_3H$, CN, halogen, $SO_2C_1$–$C_2$alkyl, unsubstituted linear or branched $C_1$–$C_4$alkyl, linear or branched $C_1$–$C_4$alkyl, substituted by OH, carboxy, $COC_1$–$C_2$alkyl or $SO_2$—N($C_1$–$C_4$alkyl)-$(CH_2)_{1-4}SO_3H$ and wherein the amino radical is substituted by H, unsubstituted linear or branched $C_1$–$C_4$alkyl or linear or branched $C_1$–$C_4$alkyl, substituted by OH or carboxy, are novel, with the exception of the compound of formula

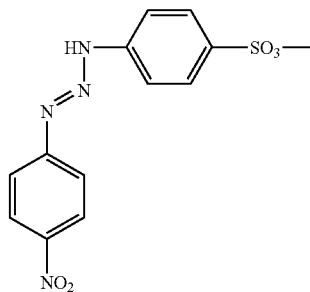

The compounds of formula (4) can likewise be prepared in a manner known per se; for example, an amine of formula q-$NH_2$ is, in customary manner, diazotised and coupled to an amine of formula R'—H, there coming into consideration as amines R—H only those compounds that couple at the nitrogen atom rather than at a carbon atom of the aromatic ring. Such compounds are, preferably, aniline derivatives substituted in the 4-position.

The multiplicity of shades of the dye, which results by the method according to the present invention, can be increased by combination with other dyes. The present invention relates also to the colouration of hair with a dye, which results by the method according to the present invention, and at least one other dye.

The dye, which results by the combination of at least one capped diazonium compound and at least one coupling compound, can be combined with dyes of the same or different class of dyes, especially with direct dyes, oxidation dyes; dye precursor combinations of a coupler compound and a diazotized compound, or a capped diazotized compound; and/or cationic reactive dyes.

Direct dyes are natural or synthetic, they are uncharged, cationic or anionic, such as acid dyes.

Oxidation dye denotes also for oxidation dye precursors, which are from the group of the developer and coupler compounds.

In the context of the invention the single classes of dyes comprise the dyes defined in the Color Index of the Society of Textile Chemist and Colorist.

In the following suitable direct dyes for the combination with the method according to the present invention are described.

Directs dyes are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, pages 248–250, and in "Europäisches Inventar der Kosmetikrohstoffe", 1996, published by The European Commission, obtainable in diskette form from the Bundesverband der deutschen Industrieund Handelsunternehmen für Arzneimittel, Reformwaren und Körperpflegemittel e.V., Mannheim.

Preferred direct dyes, which are suitable as single dye or in combination with other direct dyes, especially for semi permanent dyeing, are:

2-Amino-3-nitrophenol, 2-Amino-4-hydroxyethylaminoanisole sulfate, 2-Amino-6-chloro-4-nitrophenol, 2-Chloro-5-nitro-N-hydroxyethylene-p-phenylendiamine, 2-Hydroxyethyl-picramic acid, 2,6-Diamino-3-((pyridine-3yl)-azo)pyridine, 2-Nitro-5-glyceryl-methylaniline, 3-Methylamino-4-nitro-phenoxyethanol, 4-Amino-2-nitrodiphenyleneamine-2'-carboxilic acid, 6-Nitro-1,2,3,4,-tetrahydroquinoxaline, 4-N-Ethyl-1,4-bis(2'-hydroxyethylamino-2-nitrobenzene hydrochloride, 1-Methyl-3-nitro-4-(2'-hydroxyethyl)-aminobenzene, 3-Nitro-p-hydroxyethyl-aminophenol, 4-Amino-3-nitrophenol, 4-Hydroxypropylamine-3-nitrophenol (BN), Hydroxy-anthrylaminopropylmethyl morphlino methosulfat, 4-Nitrophenyl-aminoethylurea, 6-Nitro-p-toluidine, Acid Blue 62, Acid Blue 9, Acid Red 35, Acid Red 87 (Eosin), Acid Violet 43, Acid Yellow 1, Basic Blue 3, Basic Blue 6, Basic Blue 7, Basic Blue 9, Basic Blue 12, Basic Blue 26, Basic Blue 99, Basic Brown 16, Basic Brown 17, Basic Red 2, Basic Red 22, Basic Red 76, Basic Violet 14, Basic Yellow 57, Basic Yellow 9, Disperse Blue 3, Disperse Orange 3, Disperse Red 17, Disperse Violet 1, Disperse Violet 4, Disperse Black 9, Fast Green FCF, HC-Blue 2, HC-Blue 7, HC-Blue 8, HC-Blue 12, HC-Orange 1, HC-Orange 2, HC-Red 1, HC-Red 10-11, HC-Red 13, HC-Red 16, HC-Red 3, HC-Red BN, HC-Red 7, HC-Violet 1, HC-Violet 2, HC-Yellow 2, HC-Yellow 5, HC-Yellow 5, HC-Yellow 6, HC-Yellow 7, HC-Yellow 9, HC-Yellow 12, HC-Red 8, Hydroxyethyl-2-nitro-p-toluidine, N,N-Bis-(2-Hydroxyethyl)-2-nitro-p-phenylendiamine (BS), Picramic Acid, Solvent Green 7.

Preferred direct dyes, which are suitable as single dye or in combination with other direct dyes or oxidative dyes and oxidization agents, especially for semi permanent dyeing and permanent dyeing, are:

Disperse Violet 4, Picramic acid, N,N'-Bis-(2-Hydroxyethyl)-2-nitro-p-phenylendiamine, HC Yellow No. 5, HC Blue No. 2, HC Yellow No. 2,2-Chloro-5-nitro-N-hydroxyethyl-p-phenylendiamine, HC Red No. 3,4-Amino-3-nitrophenol, Basic Blue 99, 2-Hydroxyethyl Picramic acid, HC Yellow No. 6, Hydroxyethyl-2-nitro-p-toluidine, 2-Amino-6-chloro-4-nitrophenol, 4-Hydroxypropylamino-3-nitrophenol, Basic Red 2, HC Red No. 16 and HC Blue No. 16.

In the following suitable cationic dyes for the combination with the method according to the present invention are described.

Preferred cationic dyes are described
- in WO 95/01772, especially on page 2, line 7 to page 4, line 1, and especially on page 4, line 35 to page 8, line 21 and on pages 11 to 27, or
- in WO 01/66646, especially on page 1, line 18 to page 3, line 16, and preferred from page 16, line 20 to page 22, and cationic dyes as described on pages 10 to 17, or
- in EP 970 685, especially on page 2, line 44 to page 9, line 56 and preferably on page 9, line 58 to page 48, line 12, or
- direct dyes as described in DE-A-19 713 698, especially page 2, line 61 to page 3, line 43, or
- direct dyes and oxidizing agent as described in WO 97/20545, especially on page 1, lines 4 to 10, in particular on page 3, lines 24 to 32, and on page 11, line 6 to page 13, line 19, especially with direct dyes as described on page 5, line 28 to page 8, line 20, or
- cationic dyes and anionic UV-absorbers as described in EP 1 166 752, especially on page 3, line 20 to page 4, line 21, in particular with UV absorber on page 4, lines 26 to 3, and especially on page 7, line 47 to page 9, line 56.

More preferred are cationic dyes as described in WO 01/66646, especially on page 16, example 1, and on page 19, example 4, or as described in WO 95/01772, especially on page 11, example 1, and on page 13, example 4, or as described in WO 01/11708, especially example 6, compound of formula 106.

Also very suitable for combination with the method according to the invention are cationic nitroaniline and anthraquinone dyes, for example those described in the following patent specifications: U.S. Pat. No. 5,298,029, especially in column 2, line 33 to column 5, line 38; U.S. Pat. No. 5,360,930, especially in column 2, line 38 to column 5, line 49; U.S. Pat. No. 5,169,403, especially in column 2, line 30 to column 5, line 38; U.S. Pat. No. 5,256,823, especially in column 4, line 23 to column 5, line 15; U.S. Pat. No. 5,135,543, especially in column 4, line 24 to column 5, line 16; EP-A-818 193, especially on page 2, line 40 to page 3, line 26; U.S. Pat. No. 5,486,629, especially in column 2, line 34 to column 5, line 29; and EP-A-758 547, especially on page 7, line 48 to page 8, line 19.

Also very suitable for combination with the method according to the invention are mixtures of cationic dyes with other dyes:
- mixtures of at least two cationic dyes as described in WO 95/01772, especially on page 8, line 34 to page 10, line 22 with the given preferences, or
- combinations of Pyrazolo-[1,5-a]-pyrimidines with at least one cationic dye as described in EP 998,908, especially on page 2, line 34 to line 42, with preferred Pyrazolo-[1,5-a]-pyrimidines as described in EP 998,908, especially on page 2, line 48 to page 4, line 3, and with preferred cationic direct dyes as described in EP 998,908, especially on page 4, line 22 to page 47, line 24, or
- combinations of cationic dyes as described in FR-2788432, especially on page 53, line 1 to page 63, line 23, especially a combination of cationic dyes with Arianors in FR-2788432, especially on pages 51 to 52, or especially a combination with at least one Basic Brown 17, Basic brown 16, Basic Red 76 and Basic Red 118, and/or at least one Basic Yellow 57, and/or at least one Basic Blue 99, or
- combinations of direct dyes and/or an oxidation dye and oxidizing agents in the form of permanent-wave fixing solution, especially with direct dyes as described in DE-A-19 713 698, especially page 4, line 65 to page 35, line 59, or
- combinations of cationic dyes and an oxidation dye of the developer compound type and oxidizing agents as described in EP 850 638, especially on page 2, line 27 to page 7, line 46 and preferred on page 7, line 20 to page 9, line 26, or
- combinations of an extemporaneous mixture of a composition (A) containing one or more oxidation dye precursors and optionally one or more couplers, and of a composition (B), in powder form, containing one or more direct dye, preferably cationic, optionally dispersed in an organic pulverulent excipient and/or a mineral pulverulent excipient, and a composition (C) containing one or more oxidizing agent as described in U.S. Pat. No. 6,190,421, especially in column 2, lines 2 to 1, and preferably with oxidation dye precursors as described in column 2, line 35 to column 5, line 13, and preferably with direct dyes as described in column 5, line 30 to column 7, line 14, or
- a ready-to-use composition comprising, at least one oxidation base, at least one cationic direct dye and at least one enzyme of 2-electron oxidoreductase type in the presence of at least one donor for the said enzyme as described in U.S. Pat. No. 6,228,129, especially in column 26, line 26 to column 27, line 9 with cationic direct dyes as described in column 8, line 17 to column 13, line 65, especially those as described in column 20, line 11 to line 19, in column 23, line 61 to column 24, line 25, or
- compositions of at least one direct cationic dye and at least one nitrated benzene dye as described in WO 99/20235 on page 2, line 1 to page 7, line 9, and on page 39, line 1 to page 40b line 11, with cationic direct dyes as described on page 8, line 12 to page 25 line 6, and nitro benzene direct dyes as described on page 26, line 7 to page 30, line 15, or
- compositions of at least one direct cationic dye and at least one autooxidisable oxidation dye, especially benzene, indol and indoline derivatives as described in WO 99/20234, with in preferred direct dyes as given on page 2, line 17 to page 26, line 4, and autooxidisable oxidation dye as described especially on page 26, line 10 to page 28, line 15, or
- oxidation dyeing compositions of at least one direct dye and at least one meta-Aminophenol derivative and at least one developer compound and an oxidizing agent as described in EP 850 636, especially on page 5, line 41 to page 7, line 52, and preferably on page 19, line 50 to page 22, line 12, with preferred direct dye as described on page 18, lines 1 and 2 in connection with page 7, line 53 to page 17, line 55, and with preferred meta-Aminophenol derivatives as described on page 7, line 47 to line 52, and with preferred developer compounds as described on page 6, line 10 to page 7, line 46, or oxidation dyeing compositions of at least one direct dye and at least one developer compound selected from the group of para-Phenylenediamine derivatives and Bis-Phenylalkylenediamine and, and at least one coupler compound selected from the group of meta-Diphenols and an oxidizing agent, as described in EP-A-850 637, especially on page 6, line 50 to page 8, line 44, oxidation dyeing compositions with cationic couplers, as described in WO 99/48856, especially on page 9, line 16 to page 13, line 8, and page 11, line 20 to page 12, line 13, or cationic dye and e.g. a pyrazolo-(1,5-a)-pyrimidine derivatives, as described in EP 998 908, especially on page 2, line 34 to page 4, line 23, or arianoren and/or oxidative dyes, as described in FR-2 788 432, especially on page 2, line 16 to page 3, line 16, and page 5, line 19 to page 14, line 8, and combinations with cationic dyes as described on page 14, line 23 and following, or oxidative dye precursors (unsaturated aldehyde and coupler compounds), as described in German Patent Application 197 172 24, especially unsaturated aldehydes as described on page 2, line 50 to line 66 and page 3 line 8 to line 12 are used as developer compounds, and primary and secondary amino group compounds, nitrogen-containing heterocyclic compounds, amino acids, oligopeptids, aromatic hydroxy compounds, CH-active compounds as described on page 3, line 42 to page 5 line 25 are used as coupler compounds.

Also cationic azo dyes, e.g. according to GB-A-2 319 776, as well as the oxazine dyes described in DE-A-29 912 327 and mixtures thereof with the other direct dyes mentioned therein, can likewise readily be combined.

Especially preferred direct dye mixtures comprising a dye of formula (1) of WO 01/66646, and also the yellow dye according to Example 1 of WO 95/1772 and/or the red dye according to Example 4 of WO 95/1772 and/or the orange dye according to Example 46 of WO 95/1772.

No particular limitation is imposed on the acid dye used in the present invention so far as it is a water-soluble acid dye.

For the purpose of further modification of color shades, the method of colouring according to the invention may comprise customary acid dyes, for example from the group of the compounds known by the international names (Color index), or trade names.

Preferred examples of acid dyes are described in U.S. Pat. No. 6,248,314, they include Red Color No. 120, Yellow Color No. 4, Yellow Color No. 5, Red Color No. 201, Red Color No. 227, Orange Color No. 205, Brown Color No. 201, Red Color No. 502, Red Color No. 503, Red Color No. 504, Red Color No. 506, Orange Color No. 402, Yellow Color No. 402, Yellow Color No. 406, Yellow Color No. 407, Red Color No. 213, Red Color No. 214, Red Color No. 3, Red Color No. 104, Red Color No. 105(1), Red Color No. 106, Green Color No. 2, Green Color No. 3, Orange Color No. 207, Yellow Color No. 202(1), Yellow Color No. 202(2), Blue Color No. 202, Blue Color No. 203, Blue Color No. 205, Blue Color No. 2, Yellow Color No. 203, Blue Color No. 201, Green Color No. 201, Blue Color NO. 1, Red Color No. 230(1), Red Color No. 231, Red Color No. 232, Green Color No. 204, Green Color No. 205, Red Color No. 401, Yellow Color No. 403(1), Green Color No. 401, Green Color No. 402, Black Color No. 401 and Purple Color No. 401, especially Black Color No. 401, Purple Color 401, Orange Color No. 205.

These acid dyes may be used either single or in any combination thereof.

Preferably they are incorporated in a proportion of 0.001–5% by weight (hereinafter indicated merely by "%"), particularly 0.005–4%, more particularly 0.2–3% based on the total weight of the composition, from the viewpoint of practical use in that a sufficient hair-dyeing effect is achieved, and the hand skin is scarcely smeared.

Also very suitable for combination with the method according to the invention are uncharged dyes, for example from the group of the nitroanilines, nitrophenylenediamines, nitroaminophenols, anthraquinones, indophenols, phenazines, phenothiazines, bispyrazolons or bispyrazol aza derivatives or methines.

Also very suitable for combination with the method according to the invention are oxidation dyes.

Suitable oxidation dyes are described for example in

German Patent Application 19 94 450, especially on page 6, line 6 to line 64, or German Patent Application 19 959 479, especially in column 2, line 6 to column 3, line 11, or in the series "Dermatology", edited by Ch. Culnan, H. Maibach, Verlag Marcel Dekker Inc., New York, Basle, 1986, Vol. 7, Ch. Zviak, The Science of Hair Care, chapter 8, on pages 264–267 (oxidation dyes), or in German Patent Application 19 717 224; unsaturated aldehydes as described on page 2, line 50 to line 66 and on page 3 line 8 to line 12 are used as developer compounds, and primary and secondary amino group compounds, nitrogen-containing heterocyclic compounds, amino acids, oligopeptids, aromatic hydroxy compounds, CH-active compounds as described on page 3, line 42 to page 5 line 8 are used as coupler compounds.

Oxidation dye precursors of the developer type are for example primary aromatic amines, which are substituted in the para- or ortho-position with a substituted or unsubstituted hydroxy- or amino residue, or diaminopyridine derivatives, heterocyclic hydrazones, 4-amino-pyrazol derivatives, 2,4,5,6-tetraminopyrimidin derivatives, or unsaturated aldehydes as described in German Patent Application 19 717 224, especially on page 2, line 50 to line 66 and on page 3 line 8 to line 12, or cationic developer compounds as described in WO 00/43367, especially on page, 2 line 27 to page 8, line 24, in particular on page 9, line 22 to page 11, line 6.

Also very suitable for combination with the method according to the invention are developer dyes in their physiological compatible acid addition salt form, such as hydrochloride or sulfate. Developer dyes which have aromatic OH substituents are also suitable in their salt form with base, such as alkalimetalphenolates.

Preferred developer compounds are:

1,4-diamino-benzene (p-phenylendiamine), 1,4-diamino-2-methyl-benzene (p-toluylen-diamine), 1,4-diamino-2,6-dimethyl-benzene, 1,4-diamino-2,5-dimethyl-benzene, 1,4-diamino-2,3-dimethyl-benzene, 2-chloro-1,4-diaminobenzene, 4-phenylamino-aniline, 4-di-methylamino-aniline, 4-diethylamino-aniline, hydroxyethyl-p-phenylendiamine, 1-(2'-hydroxy-ethyl)-2,5-diaminobenzene, N,N-bis-(2-hydroxyethyl)-p-phenylendiamine, 4-[(2-methoxyethyl-)amino]-aniline, 4-[(3-hydroxypropyl) amino]-aniline, hydroxypropyl-bis-(N-hydroxyethyl-p-phenylenediamine)hydrochloride, 1,4-diamino-2-(2- hydroxyethyl)-benzene, 1,4-diamino-2-(1-methylethyl)-benzene, 2-(2,5-diaminophenoxy)-ethanol, 1,3-bis[(4-aminophenyl)(2-hydroxyethyl)amino]-2-propanol, bis-(2-hydroxy-5-aminophenyl)-methane, 1,4-bis-(4-aminophenyl)-diazacycloheptane, 1,8-bis(2,5-diaminophenoxy)-3,6-dioxaoctan, 1,10-bis-(2,5-diaminophenyl)-1,4,7,10-tetraoxadecane, hydroxyethyl-3,4-methylendioxyaniline, p-aminophenol, o-aminophenol, m-aminophenol, 2-amino-6-methyl-phenol, 4-methylaminophenol sulfate, 4-amino-m-cresol, 6-amino-m-cresol, 6-amino-m-cresol, 2-amino-4-hydroxyethylaminoanisole, 2-amino-5-methyl-phenol, 4-amino-3-methylphenol, 4-methylamino-phenol, 2-aminomethyl-4-aminophenol, 4-amino-2-[(2-hydroxyethyl)-amino]methyl-phenol, 4-amino-2-(2-hydroxyethoxy)-phenol, 4-amino-2-(methoxymethyl)-phenol, 4-amino-2-(2-hydroxyethyl)-phenol, 2-hydroxymethylamino-4-aminophenol, bis-(4-aminophenyl)amine, 4-amino-3-fluorphenol, 2-hydroxymethyl-4-aminophenol, 4-amino-2-(diethylamino)-methyl)-phenol, 5-amino-salicylsäure, 2,5-diamino-pyridine, 2-amino-3-hydroxy-pyridine, 2,6-dimethoxy-3,5-diamino-pyridine, 2,4,5,6-tetraminopyrimidine, 2-hydroxy-4,5,6-triaminopyrimidine, 4-hydroxy-2,5,6-triaminopyrimidine, 2,4-dihydroxy-5,6-diaminopyrimidine, 2-dimethylamino-4,5,6-triaminopyrimidine, 2,5,6-triamino-4-(1H)-pyrimidone, further 4,5-diaminopyrazol derivatives as described in EP 0 740 741 or WO 94/08970, especially 4,5-diamino-1-(2-hydroxyethyl)-1H-pyrazol, 4,5-diamino-1-(1-methylethyl)-1H-pyrazol, 4,5-diamino-1-[(4-methylphenyl)methyl]-1H-pyrazol, 1-[(4-chlorophenyl)methyl]-4,5-diamino-1H-pyrazol, 4,5-diamino-1-methyl-1H-pyrazol.

More preferred developer dyes are p-phenylendiamine, p-toluylendiamine, p-aminophenol, m-aminophenol, o-aminophenol, N,N-bis-(2-hydroxyethyl)-p-phenylendiamine sulfate, 2-amino-4-hydroxyethylaminoanisole sulfate, hydroxyethyl-3,4-methylenedioxyaniline, 1-(2'-hydroxyethyl)-2,5-diaminobenzene, 2,6-dimethoxy-3,5-diamino-pyridine, hydroxypropyl-bis-(N-hydroxyethyl-p-phenylenediamine)hydrochloride, hydroxyethyl-p-phenylendiamine sulfate, 4-amino-3-methylphenol, 4-methylaminophenol sulfate, 2-aminomethyl-4-aminophenol, 4,5-diamino-1-(2-hydroxyethyl)-1H-pyrazol, 4-amino-m-cresol, 6-amino-m-cresol, 5-amino-6-chloro-cresol, 2,4,5,6-tetraminopyrimidine, 2-hydroxy-4,5,6-triaminopyrimidine, 4-hydroxy-2,5,6-triaminopyrimidine sulfate.

Preferred oxidation dye precursors of the coupler type are for example m-phenylendiamine derivatives, naphthole, resorcine and resorcine derivatives, pyrazolone and m-aminophenol derivatives.

Especially preferred coupler compounds are N-(3-dimethylamino-phenyl)-urea, 4-amino-2-hydroxytoluene, 2-methyl-5-hydroxyethylaminophenol, 2,4-diaminophenoxyethanol, 2-amino-4-[(2-hydroxyethyl)amino]-anisole, p-aminophenol, m-aminophenol and its derivatives, especially 5-amino-2-methylphenol, 5-(3-hydroxypropylamino)-2-methylphenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)-amino-2-methylphenol, 3-(diethylamino)-phenol, N-cyclopentyl-3-aminophenol, 1,3-dihydroxy-5-(methylamino)-benzene, 3-(ethyl-amino)-4-methylphenol and 2,4-dichloro-3-aminophenol, o-aminophenol and its derivatives, such as 5-methyl-2-(1-methylamino)-phenol, 3-di-methylamino-phenol, 3-di-ethylamino-phenol, 5-amino-2-methyl-phenol, 5-amino-4-fluor-2-methyl-phenol, 5-amino-4-methoxy-2-methyl-phenol, 5-amino-4-ethoxy-2-methyl-phenol, 3-amino-2,4-dichlor-phenol, 5-amino-2,4-dichlor-phenol, 3-amino-2-methyl-phenol, 3-amino-2-chlor-6-methyl-phenol, 3-amino-phenol, 2-[(3-hydroxy-phenyl)amino]-acetamide, 5-[(2-hydroxyethyl)amino]-2-methyl-phenol, 3-[(2-hydroxy-ethyl)amino]-phenol, 3-[(2-methoxyethyl)amino]-phenol, 5-amino-2-ethyl-phenol, 2-(4-amino-2-hydroxyphenoxy)-ethanol, 5-[(3-hydroxypropyl)amino]-2-methyl-phenol, 3-[(2,3-dihydroxypropyl)amino]-2-methyl-phenol, 3-[(2-hydroxyethyl)amino]-2-methyl-phenol, m-diaminobenzene and its derivatives such as 2,4-diaminophenoxyethanol, 1,3-bis-(2,4-diaminophenoxy)-propane, 1-methoxy-2-amino-4-(2'-hydroxyethylamino)-benzene, 1,3-bis-(2,4-diaminophenyl)-propane, 3-[(2-aminoethyl)amino]-aniline, 1,3-di(2,4-diaminophenoxy)-propane, 1,3-diamino-2,4-dimethoxy-benzene, 2,6-bis(2-hydroxyethyl)amino-toluene, di(2,4-diaminophenoxy)-methane, 3-[di(2-hydroxyethyl)amino]-aniline, 2,6-bis-(2-hydroxyethylamino)-1-methylbenzene and 1-amino-3-bis-(2'-hydroxyethyl)-aminobenzene, o-diaminobenzene and its derivatives such as 3,4-diaminobenzoic acid and 2,3-diamino-1-methylbenzene, 2,4-diamino-1-fluor-5-methyl-benzene, 2,4-diamino-1-methoxy-5-methyl-benzene, 1-(2-aminoethoxy)-2,4-diaminobenzene, 2-amino-1-(2-hydroxyethoxy)-4-methylamino-benzene, 2,4-diaminophenoxy-acetic acid, 2,4-di-amino-1-ethoxy-5-methyl-benzene, 3-[(2-hydroxyethyl)amino]-aniline, 3,4-diamino-benzoic acid, 3,4-dihydro-6-hydroxy-1,4(2H)-benzoxazine, 6-amino-3,4-dihydro-1,4(2H)-benzoxazine, 2,4-diamino-1,5-di(2-hydroxyethoxy)-benzene, 2,4-diamino-1-(2-hydroxyethoxy)-5-methyl-benzene, 4-amino-2-di[(2-hydroxyethyl)amino]-1-ethoxy-benzene 2,4-di[(2-hydroxyethyl)amino]-1,5-dimethoxy-benzene, 3,4-dihydro-6-hydroxy-1,4(2H)-benzoxazine, 6-amino-3,4-dihydro-1,4(2H)-benzoxazine, di- or trihydroxybenzene derivatives such as resorcine, resorcinmonomethylether, 2-methylresorcine, 5-methylresorcine, 2,5-dimethylresorcine, 1-chloro-2,4-dihydroxy-benzene, 2-chlororesorcine, 4-chlororesorcine, 2,6-dihydroxyethylaminotoluene, 1,2-dichlor-3,5-dihydroxy-4-methyl-benzene, 1,5-dichlor-2,4-dihydroxy-benzene, 1,3-dihydroxy-2-methyl-benzene, pyrogallol and 1,2,4-trihydroxybenzene, pyridine derivatives such as 2,6-diamino-pyridine, 2,6-dihydroxypyridine, 2-amino-3-hydroxypyridine, 2-amino-5-chloro-3-hydroxypyridine, 5-amino-4-chloro-2-methyl-phenol, 3-diamino-6-methoxy-pyridine, 3-amino-2-methylamino-6-methoxypyridine, 2,6-dihydroxy-3,4-dimethylpyridine, 2,6-dihydroxy-4-methylpyridine, 2,6-diamino-pyridine, 2,3-diamino-6-methoxypyridine, 2,6-diamino-3,5-dimethoxy-pyridine, and 3,5-diamino-2,6-dimethoxypyridine, naphthaline derivatives such as 1-naphthol, 2-methyl-1-naphthol, 2-hydroxymethyl-1-naphthol, 2-hydroxyethyl-1-naphthol, 1,5-dihydroxynaphthaline, 1,6-dihydroxynaphthaline, 1,7-dihydroxynaphthaline, 1,8-dihydroxynaphthaline, 2,7-dihydroxy-naphthaline and 2,3-dihydroxynaphthaline, 2-methyl-1-naphthol-acetat, morpholine derivatives such as 6-hydroxybenzomorpholine and 6-aminobenzo-morpholine, chinoxaline derivatives such as 6-methyl-1,2,3,4-tetrahydrochinoxaline, pyrazol derivatives such as -phenyl-3-methylpyrazol-5-one, 3-methyl-1-phenyl-5-pyrazolone, indol derivatives such as 4-hydroxyindol, 5-hydroxy-indol, 6-hydroxyindol and 7-hydroxyindol, 2,3-indolindione, 5,6-dihydroxy-indol, 5,6-dihydroxy-indoline, methylendioxybenzene derivates such as 1-hydroxy-3,4-methylendioxybenzene, 1-amino-3,4-methylendioxybenzene and 1-(2'-hydroxyethyl)-amino-3,4-methylen-dioxybenzene, 3,4-methylendioxy-phenol, 3,4-methylendioxy-aniline, 5-[(2-hydroxy-ethyl)amino]-1,3-benzodioxol, 6-brom-1-hydroxy-3,4-methylendioxy-benzene, or cationic coupler compounds as described in FR 2 794 644, especially on page 11, line 20 to page 15, line 34, and on page 17, lines 4 to 12, page 178, line 33 to page 18, line 24.

More especially preferred coupler compounds are toluene-2,5-diamine sulfate, 1-naphthol, 1,5-, 2,7- and 1,7-dihydroxynaphthaline, 3-aminophenol, 5-amino-2-methylphenol, 2-amino-3-hydroxypyridin, resorcinol, 4-chlororesorcine, 2-chloro-6-methyl-3-aminophenol, 2,6-dihydroxyethylaminotoluene, 2-methyl-5-dihydroxyethylaminophenol, 2,4-diaminophenoxy-ethylol hydrochloride, 2-methylresorcine, 5-methylresorcine, 2,5-dimethylresorcine, 3,4-methylenedioxyphenol, 2-amino-4-hydroxyethylaminoanisole sulfate, 2,6-di-(beta-hydroxy-ethylamino)-toluene, 4-amino-2-hydroxytoluene, 6-hydroxyindol, 2-amino-3-hydroxypyridine, 2,6-dimethoxy-3,5-pyridinediamine hydrochloride and 2,6-dihydroxy-3,4-dimethylpyridine.

Most preferred coupler compounds are 2-chloro-6-methyl-3-aminophenol, 5-amino-2-methylphenol, 2-amino-3-hydroxypyridine, 2,6-di-(beta-hydroxyethylamino)-toluol, 2-methylresorcine and 1-naphthol.

The developer/-coupler combination 2,4,5,6-Tetraminopyrimidine and 2-Methylresorcine are preferred for assessing of red shades, or p-Toluenediamine and 4-Amino-2-hydroxytoluene are preferred for assessing of blue-violet shades, or p-Toluenediamine and 2-Amino-4-hydroxyethylaminoanisole are preferred for assessing of blue shades, or p-Toluenediamine and 2,4-Diamino-phenoxyethynol are preferred for assessing of blue shades, or 3-Methyl-4-aminophenol and 4-Amino-2-hydroxytlouene are preferred for assessing of orange shades, or p-Toluenediamine and resorcine are preferred for assessing of brown-green shades, or p-Toluenediamine and 1-Naphthol are preferred for assessing of blue-violet shades, or p-Toluenediamine and 2-methylresorcine are preferred for assessing of brown-gold shades.

Further, the colouring method according to the present invention may also contain autooxidizable compounds, such as, for example benzene, indol, or indoline, especially 5,6-dihydroxyindol or 5,6-dihydroxyindoline derivatives as described in WO 99/20234, especially on page 26, line 10 to page 28, line 15, or in WO 00/28957 on page 2, third paragraph.

Preferred autooxidizable benzene derivatives are:
1,2,4-trihydroxybenzene, 1-methyl-2,4,5-trihydroxybenzene, 2,4-diamnio-6-methylphenol, 2-amino-4-methylaminophenol, 2,5-diamino-4-methyl-phenol, 2,6-diamino-4-diethylamino-phenol, 2,6-diamino-1,4-dihydroxybenzen, and the salts of these compounds, which are accessible with acid.

Preferred autooxidizable indol derivatives are:
5,6-dihydroxyindol, 2-methyl-5,6-dihydroxyindol, 3-methyl-5,6-dihydroxyindole, 1-methyl-5,6-dihydroxyindol, 2,3-dimethyl-5,6-dihydroxyindol, 5-methoxy-6-dihydroxyindol, 5-acetoxy-6-hydroixyindol, 5,6-diacetoxyindol, acid of 5,6-dihydroxyindol-2-carbonacid, and the salts of these compounds, which are accessible with acid.

Preferred autooxidizable indoline derivatives are:
5,6-dihydroxyindoline, 1-methyl-5,6-dihydroxyindoline, 1-ethyl-5,6-dihydroxyindoline, and the salts of these compounds, which are accessible with acid. The colouring method according to the present invention also concerns the joint use of at least two different developers and at least one coupler compound, or combinations of at least two different couplers and at least one developer compound. Such combinations are for example described in German Patent Application 197 172 24, especially on page 3, line 31 to page 5, line 8.

In addition, the colouring method according to the present invention may also contain naturally occurring dyes, such as, for example, henna red, henna neutral, henna black, camomile blossom, sandalwood, black tea, *Rhamnus frangula* bark, sage, campeche wood, madder root, catechu, sedre and alkanet root. Such colouring methods are described, for example, in EP-A-404 868, especially on page 3, line 55 to page 4, line 9.

One further embodiment of the present invention concerns formulations, which are used for the colouration of keratin fibres, especially human hair. The formulations are applicable on human hair in different technical forms. The specific technical form may be chosen in view of the envisaged application and/or dye or dye composition. Technical forms of formulation are for example a solution, especially a thickened watery or watery alcoholic solution, a cream, foam, a gel, or an emulsion.

Preferred forms of formulations are ready to use compositions or a multi-compartment dyeing device or 'kit' or any of the multi-compartment packaging systems with compartments as described for example as described in U.S. Pat. No. 6,190,421, column 2, lines 16 to 31.

The colouring compositions for carrying out the method according to the invention may furthermore comprise any active ingredient, additive or adjuvant known for such preparations.

Adjuvants that are suitable for such formulations are in general customary in the field hair-colouring, such as for example surfactants or tensides, solvents, bases, acids, perfumes, polymeric adjuvant, thickeners and light stabilisers.

Suitable combinations of the colouring compositions for carrying out the method according to the invention with adjuvant used in the colouring of hair, for example with combination of direct dyes with oxidizing agents to achieve lightened colouration; wherein oxidizing agents especially described in WO 97/20545, especially page 9, lines 5 to 9, combination of direct dyes and/or an oxidation dye and oxidizing agents in the form of permanent-wave fixing solution, especially oxidizing agents as described in DE-A-19 713 698, especially page 4, lines 52 to 55, or EP-A-1 062 940, especially page 6, lines 41 to 47, (and in the equivalent WO 99/40895), oxidation dyes in the presence of oxidoreductase enzyme, as described in WO 99/17730, especially page 4, line 11 to page 13, line 28, and WO 99/36034, especially pages 3 to 15, combination of cationic dyes with polyols or polyethers; polyols or polyethers as described in EP-A-962 219, especially page 27, lines 14 to 38, thickening polymers, as described in EP-A-970 684, especially page 48, line 16 to page 51, line 4, sugar-containing polymers, as described in EP-A-970 687, especially page 28, line 17 to page 29, line 23, quaternary ammonium salts, as described in WO 00/10517, especially page 44, line 16 to page 46, line 23, anionic surfactants, as described in WO 00/10518, especially page 45, line 11 to page 48, line 3, non-ionic surfactants, as described in WO 00/10519, especially page 45, line 11 to page 50, line 12, or silicones, as described in WO 00/12057, especially page 45, line 9 to page 55, line 2.

oxidative agent or laser and direct dyes, as described in EP-920 856, especially on page 2, line 31 to page 53 line 36, and on page 49, line 38 to page 50, line 41, with direct dyes as described on page 3, line 54 to page 48, line 52, or direct dyes in the presence of cationic amphotere, substantive polymer, as described in EP-953 334, especially on page 2, line 39 to page 7, line 44, with direct dyes as described on page 8, line 54 to page 27, line 16, and polymers as described on page 27, line 17 to page 30, line 14, or direct dyes formulations with polymer thickener on the basis of acrylic acid, as described in EP-970 685, especially on page 2, line 39 to page 10, line 1, with direct dyes as described on page 10, line 7 to page 48, line 15, with polymers as described on page 48, line 17 to page 49, line 28.

The colouring composition for carrying out the method according to the invention in many cases comprise at least one surfactant, there being suitable in principle anionic and also zwitterionic, ampholytic, non-ionic and cationic surfactants. In many cases, however, it has proved advantageous to select the surfactants from anionic, zwitterionic and non-ionic surfactants.

Anionic surfactants suitable for use in the colouring compositions for carrying out the method according to the invention include all anionic surface-active substances that are suitable for use on the human body. Such substances are characterised by an anionic group that imparts water solubility, for example a carboxylate, sulfate, sulfonate or phosphate group, and a lipophilic alkyl group having approximately from 10 to 22 carbon atoms. In addition, glycol or polyglycol ether groups, ester, ether and amide groups and also hydroxy groups may be present in the molecule. The following are examples of suitable anionic surfactants, each in the form of sodium, potassium or ammonium salts or mono-, di- or tri-alkanolammonium salts having 2 or 3 carbon atoms in the alkanol group:

linear fatty acids having from 10 to 22 carbon atoms (soaps), ether carboxylic acids of formula $R-O-(CH_2-CH_2-O)_x-CH_2-COOH$, in which R is a linear alkyl group having from 10 to 22 carbon atoms and $x=0$ or from 1 to 16, acyl sarcosides having from 10 to 18 carbon atoms in the acyl group, acyl taurides having from 10 to 18 carbon atoms in the acyl group, acyl isothionates having from 10 to 18 carbon atoms in the acyl group, sulfosuccinic mono- and di-alkyl esters having from 8 to 18 carbon atoms in the alkyl group and sulfosuccinic monoalkylpolyoxyethyl esters having from 8 to 18 carbon atoms in the alkyl group and from 1 to 6 oxyethyl groups, linear alkane sulfonates having from 12 to 18 carbon atoms, linear α-olefin sulfonates having from 12 to 18 carbon atoms, α-sulfo fatty acid methyl esters of fatty acids having from 12 to 18 carbon atoms, alkyl sulfates and alkyl polyglycol ether sulfates of formula $R'-O(CH_2-CH_2-O)_{x'}-SO_3H$, in which R' is a preferably linear alkyl group having from 10 to 18 carbon atoms and $x'=0$ or from 1 to 12, mixtures of surface-active hydroxysulfonates according to DE-A-3 725 030, especially page 3, lines 40 to 55, sulfated hydroxyalkylpolyethylene and/or hydroxyalkylenepropylene glycol ethers according to DE-A-3 723 354, especially page 4, lines 42 to 62, sulfonates of unsaturated fatty acids having from 12 to 24 carbon atoms and from 1 to 6 double bonds according to DE-A-3 926 344, especially page 2, lines 36 to 54, esters of tartaric acid and citric acid with alcohols which are addition products of approximately from 2 to 15 molecules of ethylene oxide and/or propylene oxide with fatty alcohols having from 8 to 22 carbon atoms, or anionic surfactants, as described in WO 00/10518, especially page 45, line 11 to page 48, line 3.

Preferred anionic surfactants are alkyl sulfates, alkyl polyglycol ether sulfates and ether carboxylic acids having from 10 to 18 carbon atoms in the alkyl group and up to 12 glycol ether groups in the molecule, and also especially salts of saturated and especially unsaturated $C_8-C_{22}$carboxylic acids, such as oleic acid, stearic acid, isostearic acid and almitic acid.

Surface-active compounds that carry at least one quaternary ammonium group and at least one $-COO^{(-)}$ or $-SO_3^{(-)}$ group in the molecule are termed zwitterionic surfactants. Zwitterionic surfactants that are especially suitable are the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyl-dimethylammonium glycinate, and 2-alkyl-3-carboxymethyl-3-hydroxyethylimidazolines having from 8 to 18 carbon atoms in the alkyl or acyl group and also cocoacylaminoethylhydroxyethylcarboxymethyl glycinate. A preferred zwitterionic surfactant is the fatty acid amide derivative known by the CTFA name cocoamidopropyl betaine.

Ampholytic surfactants are to be understood as meaning surface-active compounds that, in addition to a $C_8-C_{18}$-alkyl or -acyl group, contain at least one free amino group and at least one $-COOH$ or $-SO_3H$ group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group. Ampholytic surfactants to which special preference is given are N-cocoalkyl-aminopropionate, cocoacylaminoethylaminopropionate and $C_{12}-C_{18}$acylsarcosine.

Non-ionic surfactants are described in WO 00/10519, especially page 45, line 11 to page 50, line 12.

Non-ionic surfactants contain as the hydrophilic group, for example, a polyol group, a polyalkylene glycol ether group or a combination of polyol and polyglycol ether groups.

Such compounds are, for example:

addition products of from 2 to 30 mol of ethylene oxide and/or from 0 to 5 mol of propylene oxide with linear fatty alcohols having from 8 to 22 carbon atoms, with fatty acids having from 12 to 22 carbon atoms and with alkylphenols having from 8 to 15 carbon atoms in the alkyl group, $C_{12}$–$C_{22}$ fatty acid mono- and di-esters of addition products of from 1 to 30 mol of ethylene oxide with glycerol, $C_8$–$C_{22}$alkyl-mono- and -oligo-glycosides and ethoxylated analogues thereof, addition products of from 5 to 60 mol of ethylene oxide with castor oil and hydrogenated castor oil, addition products of ethylene oxide with sorbitan fatty acid esters, addition products of ethylene oxide with fatty acid alkanolamides.

Examples of cationic surfactants that can be used in the colouring compositions for carrying out the method according to the invention are especially quaternary ammonium compounds. Preference is given to ammonium halides, such as alkyltrimethylammonium chlorides, dialkyldimethylammonium chlorides and trialkylmethylammonium chlorides, for example cetyltrimethylammonium chloride, stearyltrimethylammonium chloride, distearyldimethy-lammonium chloride, lauryidimethylammonium chloride, lauryidimethylbenzylammonium chloride and tricetylmethylammonium chloride. Further cationic surfactants that can be used in accordance with the invention are quaternised protein hydrolysates.

Also suitable in accordance with the invention are cationic silicone oils, such as, for example, the commercially available products Q2-7224 (manufacturer: Dow Corning; a stabilised trimethylsilylamodimethicone), Dow Corning 929 emulsion (comprising a hydroxylamino-modified silicone, which is also referred to as amodimethicone), SM-2059 (manufacturer: General Electric), SLM-55067 (manufacturer: Wacker) and also Abil®-Quat 3270 and 3272 (manufacturer Th. Goldschmidt; diquaternary polydimethylsiloxanes, quaternium-80), or silicones, as described in WO 00/12057, especially page 45, line 9 to page 55, line 2.

Alkylamidoamines, especially fatty acid amidoamines, such as the stearylamidopropyl-dimethylamine obtainable under the name Tego Amid® 18, are distinguished not only by a good conditioning action but also especially by their good biodegradability.

Quaternary ester compounds, so-called "esterquats", such as the methyl hydroxyalkyl-dialkoyloxyalkylammonium methosulfates marketed under the trademark Stepantex®, are also very readily biodegradable.

An example of a quaternary sugar derivative that can be used as cationic surfactant is the commercial product Glucquat® 100, according to CTFA nomenclature a "lauryl methyl gluceth-10 hydroxypropyl dimonium chloride".

The alkyl-group-containing compounds used as surfactants may be single substances, but the use of natural raw materials of vegetable or animal origin is generally preferred in the preparation of such substances, with the result that the substance mixtures obtained have different alkyl chain lengths according to the particular starting material used.

The surfactants that are addition products of ethylene and/or propylene oxide with fatty alcohols or derivatives of such addition products may either be products having a "normal" homologue distribution or products having a restricted homologue distribution. "Normal" homologue distribution is to be understood as meaning mixtures of homologues obtained in the reaction of fatty alcohol and alkylene oxide using alkali metals, alkali metal hydroxides or alkali metal alcoholates as catalysts. Restricted homologue distributions, on the other hand, are obtained when, for example, hydrotalcites, alkali metal salts of ether carboxylic acids, alkali metal oxides, hydroxides or alcoholates are used as catalysts. The use of products having restricted homologue distribution may be preferred.

Examples of further active ingredients, adjuvants and additives are as follows:

non-Ionic polymers, for example vinylpyrrolidone/vinyl acrylate copolymers, polyvinylpyrrolidone and vinylpyrrolidone/vinyl acetate copolymers and polysiloxanes, cationic polymers, such as quaternised cellulose ethers, polysiloxanes having quaternary groups, dimethyldiallylammonium chloride polymers, copolymers of dimethyldiallylammonium chloride and acrylic acid, as available commercially under the name Merquat® 280 and the use of which in hair colouring is described, for example, in DE-A-4 421 031, especially page 2, lines 20 to 49, or EP-A-953 334, especially page 27, line 17 to page 30, line 11, acrylamide/dimethyldiallylammonium chloride copolymers, diethyl-sulfate-quaternised dimethylaminoethyl methacrylate/vinylpyrrolidone copolymers, vinylpyrrolidone/imidazolinium methochloride copolymers, quaternised polyvinyl alcohol, zwitterionic and amphoteric polymers, such as, for example, acrylamido-propyl-trimethylammonium chloride/acrylate copolymers and octylacrylamide/methyl methacrylate/tert-butylaminoethyl methacrylate/2-hydroxypropyl methacrylate copolymers, anionic polymers, such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butyl acrylamide terpolymers, thickeners, such as agar, guar gum, alginates, xanthan gum, gum arabic, karaya gum, locust bean flour, linseed gums, dextrans, cellulose derivatives, e.g. methyl cellulose, hydroxyalkyl cellulose and carboxymethyl cellulose, starch fractions and derivatives, such amylose, amylopectin and dextrins, clays, e.g. bentonite or fully synthetic hydrocolloids such as, for example, polyvinyl alcohol, structuring agents, such as glucose and maleic acid, hair-conditioning compounds, such as phospholipids, for example soya lecithin, egg lecithin, and cephalins, silicone oils, and also conditioning compounds, for example such as those described in DE-A-19 729 080, especially page 2, lines 20 to 49, EP-A-834 303, especially page 2, line 18 to page 3, line 2, or EP-A-312 343, especially page 2, line 59 to page 3, line 11, protein hydrolysates, especially elastin, collagen, keratin, milk protein, soya protein and wheat protein hydrolysates, condensation products thereof with fatty acids and also quaternised protein hydrolysates, perfume oils, dimethyl isosorbitol and cyclodextrins, solubilisers, such as ethanol, isopropanol, ethylene glycol, propylene glycol, glycerol and diethylene glycol, anti-dandruff active ingredients, such as piroctones, olamines and zinc Omadine, further substances for adjusting the pH value, active ingredients such as panthenol, pantothenic acid, allantoin, pyrrolidonecarboxylic acids and salts thereof, plant extracts and vitamins, cholesterol, light stabilisers and UV absorbers, as described, for example, in EP-A-819 422, especially page 4, lines 34 to 37, consistency regulators, such as sugar esters, polyol esters or polyol alkyl ethers, fats and waxes, such as spermaceti, beeswax, montan wax, paraffins, fatty alcohols and fatty acid esters,
fatty alkanolamides,
polyethylene glycols and polypropylene glycols having a molecular weight of from 150 to 50 000, for example such as those described in EP-A-801 942, especially page 3, lines 44 to 55,
complexing agents, such as EDTA, NTA and phosphonic acids,
swelling and penetration substances, such as polyols and polyol ethers, as listed extensively, for example, in EP-A-962 219, especially page 27, lines 18 to 38, for example glycerol, propylene glycol, propylene glycol monoethyl ether, butyl glycol, benzyl alcohol, carbonates, hydrogen carbonates, guanidines, ureas and also primary, secondary and tertiary phosphates, imidazoles, tannins, pyrrole,
opacifiers, such as latex,
pearlising agents, such as ethylene glycol mono- and di-stearate,
propellants, such as propane-butane mixtures, $N_2O$, dimethyl ether, $CO_2$ and air, and also
antioxidants,
polyols or polyethers, as described in EP-A-962 219, especially page 27, lines 14 to 38,
thickening polymers, as described in EP-A-970 684, especially page 48, line 16 to page 51, line 4,
sugar-containing polymers, as described in EP-A-970 687, especially page 28, line 17 to page 29, line 23,
quaternary ammonium salts, as described in WO 00/10517, especially page 44, line 16 to page 46, line 23.

In the context of the present invention, oxidizing agents are understood to be any oxidizing agent customarily used for oxidative hair colouring, for example dilute hydrogen peroxide solutions, hydrogen peroxide emulsions or hydrogen peroxide gels, alkaline earth metal peroxides, organic peroxides, such as urea peroxides, melamine peroxides, or alkalimetalbromat fixations are also applicable if a shading powder on the basis of semi-permanent, direct hair dyes is used.

Preferred oxidizing agent is hydrogen peroxide, preferred in about 2 to 30% by weight, more preferred in 3 to 20% by weight, and most preferred in 6 to 12% by weight of the total weight of a watery composition such as a solution, dispersion, a gel or emulsion.

The watery composition can comprise all customary components, which are used for the different applications of oxidizing agent compositions as described in K. Schrader, "Grundlagen und Rezepturen der Kosmetika", 2. Aufl. (1989), page 832–840.

Further preferred oxidizing agents are
oxidizing agents to achieve lightened colouration, as described in WO 97/20545, especially page 9, lines 5 to 9,
oxidizing agents in the form of permanent-wave fixing solution, as described in DE-A-19 713 698, especially page 4, lines 52 to 55, and lines 60 and 61 or EP-A-1 062 940, especially page 6, lines 41 to 47, (and in the equivalent WO 99/40895).

An oxidizing agents may be present in the colouring compositions for carrying out the method according to the invention preferably in an amount of from 0.01% to 6%, especially from 0.01% to 1%, based on the total dyeing composition.

Preferred catalysts are metal ions, such as for example $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$ and $Al^{3+}$, preferably $Zn^{2+}$, $Cu^{2+}$ and $Mn^{2+}$.

The metal ions are applicable in any physiological suitable salts form. Preferred salts are acetate, sulfate, halogenide, lactate and tartrate.

Alkalimetalsulfits, such as sodium-, potassium-, lithium-sulfite, Alkalimetaldisulfits, such as sodium-, potassium-, lithium-disulfite, ascorbic acid, tert.-Butylhydrochinon and Ammoniumthiolactat.

In general, the coloration with an oxidative agent is conducted in the presence of a base. Bases are for example ammonia, alkali metal carbonates, earth metal carbonates, alkanol amines, such as for example mono-, di- or triethanolamine, alkali metal hydroxides, earth metal hydroxides, compounds of the formula

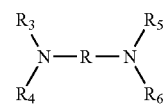

wherein,
R is a propyl residue, which substituted with OH or $C_1$–$C_4$-alkyl,
$R_3$, $R_4$, $R_5$ and $R_6$ are independently or dependently from each other hydrogen, $C_1$–$C_4$-alkyl or hydroxy-($C_1$–$C_4$)-alkyl.

Alkali metal is for example sodium, potassium or lithium. Earth metal is for example magnesium or calcium.

Acids are inorganic or organic acids, such as hydrochloride, tartrat acid, citric acid, ascorbine acid and phosphor acid.

The use of UV absorbers can effectively protect natural and dyed hair from the damaging rays of the sun and increase the wash fastness of dyed hair.

Suitable UV absorbers the colouring compositions for carrying out the method according to the invention are:
cationic benzotriazole UV absorbers as for example described in WO 01/36396 especially on page 1, line 20 to page 2, line 24, and preferred on page 3 to 5, and on pages 26 to 37, or
cationic benzotriazole UV in combination with antioxidants as described in WO 01/36396, especially on page 11, line 14 to page 18, or
UV absorbers in combination with antioxidants as described in U.S. Pat. No. 5,922,310, especially in column 2, lines 1 to 3,
UV absorbers in combination with antioxidants as described in U.S. Pat. No. 4,786,493, especially in column 1, 42 to column 2, line 7, and preferred in column 3, 43 to column 5, line 20, or
combination of UV absorbers as described in U.S. Pat. No. 5,830,441, especially in column 4, lines 53 to 56, or
combination of UV absorbers as described in WO 01/36396, especially on page 11, lines 9 to 13, or
triazine derivatives provide effective UV protection as described in WO 98/22447, especially on page 1, line 23 to page 2, line 4, and preferred on page 2, line 11 to page 3, line 15 and most preferred on pages 6 to 7, and 12 to 16, or
combination of the cosmetic formulations as described in WO 98/22447 with one or more than one further UV filter as described in the following patents:

(Abbreviations T: table, R: row, Comp: compound, Ex: compound(s) of patent example, p: page)

| | |
|---|---|
| EP 895776 | Comp. in Rows 48–58, p 3; R 25 + 33, p 5 |
| WO 9220690 | Polymeric comp in Examples 3–6 |
| EP 1000950 | Comp. in Table 1, pp 18–21 |
| EP 1060734 | T 1–3, pp 11–14 |
| EP 1059082 | Ex 1; T 1, pp 9–11 |
| EP 1008586 | Ex 1–3, pp 13–15 |
| EP 1005855 | T 3, p 13 |
| EP 1129695 | Ex 1–7, pp 13–14 |
| EP 967200 | Ex 2; T 3–5, pp 17–20 |
| EP 945125 | T 3 a + b, pp 14–15 |
| EP 924246 | T 2, p 9 |
| EP 911020 | T 2, p 11–12 |
| EP 916335 | T 2–4, pp 19–41 |
| EP 852137 | T 2, pp 41–46 |
| EP 858318 | T 1, p 6 |
| EP 826361 | T 1, pp 5–6 |
| EP 503338 | T 1, pp 9–10 |
| WO 9301164 | T 1 + 2, pp 13–22 |
| EP 823418 | Ex 1–4, pp 7–8 |
| WO 9714680 | Ex 1–3, p 10 |
| EP 1027883 | Compound VII, p 3 |
| EP 832641 | Ex 5 + 6 p 7; t 2, p 8 |
| U.S. Pat. No. 5338539 | Ex 1–9, pp 3 + 4 |
| EP 517103 | Ex 3, 4, 9, 10 pp 6–7 |
| EP 1123934 | T 3, p 10 |
| EP 1027883 | Comp I–VI, p 3 |
| EP 969004 | Ex 5, T 1, pp 6–8 |
| U.S. Pat. No. 5801244 | Ex 1–5, pp 6–7 |
| EP 832642 | Ex 22, T 3 pp, 10–15; T 4, p 16 |
| U.S. Pat. No. 5346691 (EP 570838) | Ex 40, p 7; T 5, p 8 |
| EP 517104 | Ex 1, T 1, pp 4–5; Ex 8, T 2, pp 6–8 |
| WO 200149686 | Ex 1–5, pp 16–21 |
| EP 944624 | Ex 1 + 2, pp13–15 |
| EP 933376 | Ex 1–15, pp 10–21 |
| EP 863145 | Ex 1–11, pp 12–18 |
| EP 780382 | Ex 1–11, pp 5–7 |
| EP 626950 | |
| EP 1081140 | Ex 1–9, pp 11–16 |
| WO 9217461 | Ex 1–22, pp 10–20 |
| WO 0168047 | Tables on pp 85–96 |
| EP 613893 | Ex 1–5 + 15, T 1, pp 6–8 |
| EP 1064922 | Compounds 1–34, pp 6–14 |
| EP 1028120 | Ex 1–5, pp 5–13 |
| EP 1008593 | Ex 1–8, pp 4–5 |
| EP 669323 | Ex 1–3, p 5 |
| EP 1108712 | 4,5-Dimorpholino-3-hydroxypyridazine |
| JP 2000319629 | CAS Regno. 80142-49-0, 137215-83-9, 307947-82-6 |
| EP 420707 B1 | Ex 3, p 13 (80142-49-0) |
| U.S. Pat. No. 5635343 | |
| EP 1167358 | |

In addition to the triazine UV absorbers described in WO 98/22447, the cosmetic formulations can also contain one or more than one further UV protective of the following substance classes:

p-aminobenzoic acid derivatives, for example 4-dimethylaminobenzoic acid 2-ethylhexyl ester;

salicylic acid derivatives, for example salicylic acid 2-ethylhexyl ester;

benzophenone derivatives, for example 2-hydroxy-4-methoxybenzophenone and its 5-sulfonic acid derivative;

dibenzoylmethane derivatives, for example 1-(4-tert-butylphenyl)-3-(4-methoxyphenyl)propane-1,3-dione;

diphenylacrylates, for example 2-ethylhexyl 2-cyano-3,3-diphenylacrylate, and 3-(benzofuranyl)2-cyanoacrylate;

3-imidazol-4-ylacrylic acid and esters;

benzofuran derivatives, especially 2-(p-aminophenyl)benzofuran derivatives, described in EP-A-582 189, U.S. Pat. No. 5,338,539, U.S. Pat. No. 5,518,713 and EP-A-613 893;

polymeric UV absorbers, for example the benzylidene malonate derivatives described in EP-A-709 080;

cinnamic acid derivatives, for example the 4-methoxycinnamic acid 2-ethylhexyl ester and isoamyl ester or cinnamic acid derivatives described in U.S. Pat. No. 5,601, 811 and WO 97/00851;

camphor derivatives, for example 3-(4'-methyl)benzylidenebornan-2-one, 3-benzyl-idenebornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylenedimethine)-bis(7, 7-dimethyl-2-oxo-bicyclo[2.2.1]heptane-1-methanesulfonic acid) and salts, 3-(4'-sulfo)benzylidenebornan-2-one and salts; camphorbenzalkonium methosulfate;

hydroxyphenyltriazine compounds, for example 2-(4'-methoxyphenyl)-4,6-bis(2'-hydroxy-4'-n-octyloxyphenyl)-1,3, 5-triazine; 2,4-bis{[4-(3-(2-propyloxy)-2-hydroxy-propyloxy)-2-hydroxy]-phenyl}-6-(4-methoxyphenyl)-1,3,5-triazine; 2,4-bis{[4-(2-ethyl-hexyloxy)-2-hydroxy]-phenyl}-6-[4-(2-methoxyethyl-carboxyl)-phenylamino]-1,3,5-triazine; 2,4-bis{[4-(tris(trimethylsilyloxy-silylpropyloxy)-2-hydroxy]-phenyl}-6-(4-methoxyphenyl)-1,3,5-triazine; 2,4-bis{[4-(2"-methylpropenyloxy)-2-hydroxy]-phenyl}-6-(4-methoxyphenyl)-1,3,5-triazine; 2,4-bis{[4-(1',1',1',3',5', 5',5'-heptamethyltrisilyl-2"-methyl-propyloxy)-2-hydroxy]-phenyl}-6-(4-methoxyphenyl)-1,3,5-triazine; 2,4-bis{[4-(3-(2-propyloxy)-2-hydroxy-propyloxy)-2-hydroxy]-phenyl}-6-[4-ethylcarboxy)-phenylamino]-1,3,5-triazine;

benzotriazole compounds, for example 2,2'-methylene-bis (6-(2H-benzotriazol-2-yl)-4-(1,1,3,3-tetramethylbutyl)-phenol;

trianilino-s-triazine derivatives, for example 2,4,6-trianiline-(p-carbo-2'-ethyl-1'-oxy)-1,3,5-triazine and the UV absorbers disclosed in U.S. Pat. No. 5,332,568, EP-A-517 104, EP-A-507 691, WO 93/17002 and EP-A-570 838;

2-phenylbenzimidazole-5-sulfonic acid and salts thereof;

methyl o-aminobenzoates;

physical sunscreens coated or not as titanium dioxide, zinc oxide, iron oxides, mica, MnO, $Fe_2O_3$, $Ce_2O_3$, $Al_2O_3$, $ZrO_2$. (surface coatings: polymethylmethacrylate, methicone (methylhydrogenpolysiloxane CAS 9004-73-3), dimethicone, isopropyl titanium triisostearate (CAS 61417-49-0), metal soaps as magnesium stearate (CAS 4086-70-8), perfluoroalcohol phosphate as C9-15 fluoroalcohol phosphate (CAS 74499-44-8; JP 5-86984, JP 4-330007)). The primary particle size is an average of 15 nm-35 nm and the particle size in dispersion is in the range of 100 nm-300 nm.

aminohydroxy-benzophenone derivatives disclosed in DE 10011317, EP 1133980 and EP 1046391 phenyl-benzimidazole derivatives as disclosed in EP 1167358

The UV absorbers described in "Sunscreens", Eds. N. J. Lowe, N. A. Shaath, Marcel Dekker, Inc., New York and Basle or in Cosmetics & Toiletries (107), 50ff (1992) also can be used as additional UV protective substances.

Examples of (synergistic) combinations of UV absorbers in cosmetic or pharmaceutical preparations are also described in the following table. The combinations of UV filters are useful to protect skin, hair and/or natural or artificial hair color (ratio of UV absorbers in columns C1–C12).

| No | | Chemical Name | CAS No. | C1 | C2 | C3 | C4 | C5 | C6 | C7 | C8 | C9 | C10 | C11 | C12 |
|---|---|---|---|---|---|---|---|---|---|---|---|---|---|---|---|
| UV | 1 | (+/−)-1,7,7-trimethyl-3-[(4-methylphenyl)-methylene]bicyclo[2.2.1]heptan-2-one | 36861-47-9 | | 15 | | | | | | | | | | |
| UV | 2 | 1,7,7-trimethyl-3-(phenylmethylene)-bicyclo[2.2.1]heptan-2-one | 15087-24-8 | | | | | | | | | | | | |
| UV | 3 | (2-Hydroxy-4-methoxyphenyl)(4-methylphenyl)methanone | 1641-17-4 | | | | | | | | | | 10 | | |
| UV | 4 | 2,4-dihydroxy-benzophenone | 131-56-6 | | | | | | | | | | 10 | | |
| UV | 5 | 2,2',4,4'-tetrahydroxy-benzophenone | 131-55-5 | | | | | | | | | | 10 | | |
| UV | 6 | 2-Hydroxy-4-methoxybenzophenone; | 131-57-7 | | | | | | | | | | | | |
| UV | 7 | 2-Hydroxy-4-methoxybenzophenone-5-sulfonic acid | 4065-45-6 | | | | | | | | | | | | |
| UV | 8 | 2,2'-dihydroxy-4,4'-dimethoxybenzo-phenone | 131-54-4 | | | | | 10 | | | | | 10 | | |
| UV | 9 | 2,2'-Dihydroxy-4-methoxybenzophenone | 131-53-3 | | | | | | | | | | 10 | | |
| UV | 10 | Alpha-(2-oxoborn-3-ylidene)toluene-4-sulphonic acid and its salts | 56039-58-8 | | | | 15 | 10 | | | | | 10 | | |
| UV | 11 | 1-[4-(1,1-dimethylethyl)phenyl]-3-(4-methoxyphenyl)-propane-1,3-dione | 70356-09-1 | | 15 | | | | | | 10 | | | | |
| UV | 12 | Methyl N,N,N-trimethyl-4-[(4,7,7-trimethyl-3-oxobicyclo[2,2,1]hept-2-ylidene)methyl]-anilinium sulphate; | 52793-97-2 | | | | | | | | | | | | |
| UV | 22 | 3,3,5-Trimethyl cyclohexyl-2-hydroxy benzoate | 118-56-9 | | | | | | | | | | | | |

| No | | Chemical Name | CAS No. | C1 | C2 | C3 | C4 | C5 | C6 | C7 | C8 | C9 | C10 | C11 | C12 |
|---|---|---|---|---|---|---|---|---|---|---|---|---|---|---|---|
| UV | 23 | Isopentyl p-methoxy-cinnamate | 71617-10-2 | | | | | | | | | | | 10 | |
| UV | 27 | Menthyl-o-aminobenzoate | 134-09-8 | | | | | | | | | | | | |
| UV | 28 | Methyl salicylate | 89-46-3 | | | | 15 | | | | | | | | |
| UV | 29 | 2-Ethylhexyl 2-cyano,3,3-diphenylacrylate | 6197-30-4 | 15 | | | | | | | | | 10 | | |
| UV | 30 | 2-ethylhexyl 4-(dimethyl-amino)benzoate | 21245-02-3 | | | | | | | | | | | | |
| UV | 31 | 2-ethylhexyl 4-methoxycinnamate | 5466-77-3 | 20 | | | | | | | 25 | 50 | | | |
| UV | 32 | 2-ethylhexyl salicylate | 118-60-5 | | | | | | | | | | | | |
| UV | 33 | Benzoic acid, 4,4',4''-(1,3,5-triazine-2,4,6-triyltri-imino)tris-, tris(2-ethylhexyl) ester; 2,4,6-Trianilino-(p-carbo-2'-ethylhexyl-1'-oxi)-1,3,5-triazine | 88122-99-0 | | | | | 20 | | | | | 10 | | |
| UV | 34 | 4-aminobenzoic acid | 150-13-0 | | | | | | | | | | | | |
| UV | 35 | Benzoic acid, 4-amino-, ethyl ester, polymer with oxirane | 113010-52-9 | | | | | | | | | | | | |
| UV | 38 | 2-phenyl-1H-benzimidazole-5-sulphonic acid | 27503-81-7 | | | | | 15 | | | | | 10 | 10 | |
| UV | 39 | 2-Propenamide, N-[[4-[(4,7,7-trimethyl-3-oxobicyclo-[2.2.1]hept-2-ylidene)methyl]-phenyl]methyl]-, homopolymer | 147897-12-9 | | | | | | | | | | | | |

| No | | Chemical Name | CAS No. | C1 | C2 | C3 | C4 | C5 | C6 | C7 | C8 | C9 | C10 | C11 | C12 |
|---|---|---|---|---|---|---|---|---|---|---|---|---|---|---|---|
| UV | 40 | Triethanolamine salicylate | 2174-16-5 | | | | | | | | | | | | |
| UV | 41 | 3,3'-(1,4-phenylene-dimethylene)bis[7,7-dimethyl-2-oxo-bicyclo[2.2.1]heptane-1-methanesulfonic acid] | 90457-82-2 | | | | | | | | | | | | |
| UV | 42 | Titanium dioxide | 13463-67-7 | 5 | 7.5 | | | | | 25 | | | | 10 | 10 |
| UV | 44 | Zinc oxide | 1314-13-2 | | | | 15 | | | 10 | | | | | 10 |
| UV | 45 | 2,2'-Methylene-bis-[6-(2H-benzotriazol-2-yl)-4-(1,1,3,3-tetramethyl-butyl)-phenol] | 103597-45-1 | | | | | 15 | | 20 | 20 | | | 10 | 10 |
| UV | 46 | 2,4-bis{[4-(2-ethyl-hexyloxy)-2-hydroxy]-phenyl}-6-(4-methoxyphenyl)(1,3,5)-triazine | 187393-00-6 | 10 | 15 | | | 15 | 15 | | | | | | 10 |
| UV | 47 | 1H-Benzimidazole-4,6-disulfonic acid, 2,2'-(1,4-phenylene)bis-, disodium salt | 180898-37-7 | | | | | | 15 | | | | | | 10 |
| UV | 48 | Benzoic acid, 4,4'-[[6-[[4-[[(1,1-dimethyl-ethyl)amino]carbonyl]-phenyl]amino]1,3,5-triazine-2,4-diyl]diimino]bis-, bis(2-ethylhexyl)ester | 154702-15-5 | 20 | | | | 15 | | | | | | 10 | 10 |
| UV | 49 | Phenol, 2-(2H-benzotriazol-2-yl)-4-methyl-6-[2-methyl-3-[1,3,3,3-tetramethyl-1-[(trimethylsilyl)oxy]-disiloxanyl]propyl]- | 155633-54-8 | | | 15 | | | | 15 | | | | 10 | 10 |
| UV | 50 | alpha-(trimethylsilyl)-omega-(trimethylsilyloxy) poly[oxy(dimethyl)silylene]-co-[oxy(methyl)(2-{p-[2,2-bis(ethoxy-carbonyl)vinyl]phenoxy}-1-methyleneethyl)silylene]-co-[oxy(methyl)(2-{p-[2,2-bis(ethoxycarbonyl)vinyl]phenoxy}prop-1-enyl)silylene] | 207574-74-1 | | | 15 | | | | 15 | | | | | 10 |
| UV | 51 | Benzenesulfonic acid, 3-(2H-benzotriazol-2-yl)-4-hydroxy-5-(1-methy-lpropyl)-, monosodium salt | 92484-48-5 | | | | | | | | | | 10 | | |
| UV | 52 | Benzoic acid, 2-[4-(diethylamino)-2-hydroxybenzoyl]-, hexyl ester | 302776-68-7 | 40 | 25 | 15 | 15 | | 30 | 10 | 10 | 25 | 10 | | |
| UV | 53 | 1-Dodecanaminium, N-[3-[[4-(dimethylamino)benzoyl]amino]propyl]-N,N-dimethyl-, salt with 4-methylbenzenesulfonic acid (1:1) | 156679-41-3 | | | | | | | | | | | | |
| UV | 54 | 1-Propanaminium, N,N,N-trimethyl-3-[(1-oxo-3-phenyl-2-propenyl)amino]-, chloride | 177190-98-6 | | | | | | | | | | | | |
| UV | 55 | 1H-Benzimidazole-4,6-disulfonic acid, 2,2'-(1,4-phenylene)bis- | 170864-82-1 | | | 15 | | 10 | | | | | | 10 | 10 |
| UV | 56 | 1,3,5-Triazine, 2,4,6-tris(4-methoxyphenyl)- | 7753-12-0 | 10 | 7.5 | 15 | 10 | 5 | 50 | 25 | 25 | 25 | 10 | | 10 |
| UV | 57 | 1,3,5-Triazine, 2,4,6-tris[4-[(2-ethylhexyl)oxy]phenyl]- | 208114-14-1 | | 15 | 10 | | | | | | | | | 10 |

-continued

| No | | Chemical Name | CAS No. | C1 | C2 | C3 | C4 | C5 | C6 | C7 | C8 | C9 | C10 | C11 | C12 |
|---|---|---|---|---|---|---|---|---|---|---|---|---|---|---|---|
| UV | 58 | 1-Propanaminium, 3-[[3-[3-(2H-[[3-[3-(2H-benzotriazol-2-yl)-5-(1,1-dimethylethyl)-4-hydroxyphenyl]-1-oxopropyl]amino]-N,N-diethyl-N-methyl-, methyl sulfate (salt) | 340964-15-0 | | | | | | | | | | | | |
| UV | 59 | 2-Propenoic acid, 3-(1H-imidazol-4-yl)- | 104-98-3 | | | | | | | | | | | | |
| UV | 60 | Benzoic acid, 2-hydroxy-, [4-(1-methylethyl)phenyl]methyl ester | 94134-93-7 | | | | | | | | | | | | |
| UV | 61 | 1,2,3-Propanetriol, 1-(4-aminobenzoate) | 136-44-7 | | | | | | | | | | | | |
| UV | 62 | Benzeneacetic acid, 3,4-dimethoxy-a-oxo- | 4732-70-1 | | | | | | | | | | | | |
| UV | 63 | 2-Propenoic acid, 2-cyano-3,3-diphenyl-, ethyl ester | 5232-99-5 | | | | | | | | | | | | |

The following examples C1–C12 illustrate combinations of UV absorbers and antioxidants in cosmetic preparations which are useful to protect hair and natural or artificial hair color (% by weight, based on the total weight of the composition).

| Compound (CAS No.) | C1 | C2 | C3 | C4 | C5 | C6 | C7 | C8 | C9 | C10 |
|---|---|---|---|---|---|---|---|---|---|---|
| [Structure shown: benzotriazole UV absorber with methyl sulfate salt] | 2 | 3 | 4 | 1 | 2 | 3 | 1 | 2 | 2.5 | 1 |
| BENZENESULFONIC ACID, 3-(2H-BENZOTRIAZOL-2-YL)-4-HYDROXY-5-(1-METHYLPROPYL)-, MONOSODIUM SALT (92484-48-5) | 1 | 1 | | | | | | | | |
| PROPYL GALLATE (121-79-9) | 1 | 0.5 | | | | 1 | | | 1 | |
| N-[3-(3,5-DI-TERT-BUTYL-4-HYDROXYPHENYL)PROPIONYL] SULFANILC ACID (OR SALTS E.G. WITH SODIUM) | | | | 2 | 1 | | | 1 | 2 | |
| BENZYLIDENE MALONATE POLYSILOXANE (207574-74-1) | | | | 2 | | | 0.2 | | | |
| DROMETRIZOLE TRISILOXANE (155633-54-8) | | | 1 | | | | 0.5 | | | |
| DIETHYLHEXYL BUTAMIDO TRIAZONE (154702-15-5) | | | | | | 0.2 | | | | |

-continued

| Compound (CAS No.) | C1 | C2 | C3 | C4 | C5 | C6 | C7 | C8 | C9 | C10 |
|---|---|---|---|---|---|---|---|---|---|---|
| PHENOL, 2,2'-[6-(4-METHOXYPHENYL)-1,3,5-TRIAZINE-2,4-DIYL]BIS[5-[(2-ETHYLHEXYL)OXY]- (187393-00-6) | | | | | 0.2 | | | | | |
| 1H-BENZIMIDAZOLE-4,6-DISULFONIC ACID, 2,2'-(1,4-PHENYLENE)BIS-, DISODIUM SALT (180898-37-7) | | | | | | 1 | | | | |

| Compound (CAS No.) | C1 | C2 | C3 | C4 | C5 | C6 | C7 | C8 | C9 | C10 |
|---|---|---|---|---|---|---|---|---|---|---|
| BIS-BENZOTRIAZOLYL TETRAMETHYLBUTYL-PHENOL (103597-45-1) | | | | | 0.5 | | | | | |
| TEREPHTHALYLIDENE DICAMPHOR SULFONIC ACID (90457-82-2) | | | | | 0.5 | | | | | |
| POLYACRYLAMIDOMETHYL BENZYLIDENE CAMPHOR (113783-61-2) | | | | | 1 | | | | | |
| PHENYLBENZIMIDAZOLE SULFONIC ACID (27503-81-7) | | | | | | 1 | | | | |
| ETHYLHEXYL METHOXY-CINNAMATE (5466-77-3) | 0.5 | 0.5 | | | 0.2 | | | | 0.5 | |
| OCTOCRYLENE (6197-30-4) | | | | | | 0.5 | | 0.5 | | |
| CAMPHOR BENZALKONIUM METHOSULFATE (52793-97-2) | | | | | | 0.5 | 0.1 | | | |
| BUTYL METHOXYDIBENZOYL-METHANE (70356-09-1) | | | | | | 1 | | | | |
| BENZOPHENONE-3 (131-57-7) | 0.1 | 0.1 | | | | 0.5 | 0.2 | | | |
| BENZOPHENONE-4 (4065-45-6) | 0.1 | 0.1 | | | | 0.5 | | | | |
| 1-DODECANAMINIUM, N-[3-[[4-(DIMETHYLAMINO)-BENZOYL]AMINO]PROPYL]-N,N-DIMETHYL-, SALT WITH 4-METHYLBENZENESULFONIC ACID (156679-41-3) | | | | | | | | | 1 | |
| 1-PROPANAMINIUM, N,N,N-TRIMETHYL-3-[(1-OXO-3-PHENYL-2-PROPENYL)AMINO]-, CHLORIDE (177190-98-6) | | | | | | | 1 | | 1 | |
| 3-BENZYLIDENE CAMPHOR (15087-24-8) | | | | | | | 0.5 | | | |
| 4-METHYLBENZYLIDENE CAMPHOR (36861-47-9) | | | | | | | 0.2 | | | |
| BENZYLIDENE CAMPHOR SULFONIC ACID (56039-58-8) | | | | | | | | | | 1 |

Preference is given to the use of mixing ratios of triazine derivatives of formula 1–8/further light-protective agents from 1:99 to 99:1, especially from 1:95 to 95:1 and preferably from 10:90 to 90:10, based on weight. Of special interest are mixing ratios of from 20:80 to 80:20, especially from 40:60 to 60:40 and preferably approximately 50:50. Such mixtures can be used, inter alia, to improve solubility or increase UV absorption.

Synergistic effects are observed when UV absorbers are used in combination with antioxidants. Examples of antioxidants that can be used are listened in WO 01/36396 (pages 11–18), U.S. Pat. No. 5,922,310 and U.S. Pat. No. 4,786,493.

Examples of UV absorbers used in addition to the uncharged and cationic benzotriazole UV absorbers in the formulations without limitation to those listed in the following might be benzophenone-type substances such as benzophenone-1, benzophenone-2, benzophenone-3, benzophenone-4, benzophenone-5 (sodium salt) or benzotriazol-type substances such as benzenesulfonic acid, 3-(2H-benzotriazol-2-yl)-4-hydroxy-5-(1-methylpropyl)-, monosodium salt; 2-(5-chloro-2H-benzotriazol-2-yl)-6-(1,1-dimethylethyl)-4-methyl-phenol; 2-(2H-benzotriazol-2-yl)-6-dodecyl-4-methyl-phenol, branched and linear. Typical ingredients in the oil phase of emulsions (water in oil, oil in water or triple emulsion) or used in hair oils can be chosen from the following substance groups without limiting the kind of lipophilic ingredients to those substances:

Suitable cosmetic preparations may contain usually from 0.05 to 40% by weight, preferably from 0.1 to 20% by weight, based on the total weight of the composition, of one or more UV absorbers.

Preferred are the cosmetic preparations contain at least one triazine derivative UV absorber, for example, from 0.1 to 40% by weight, preferably from 0.1 to 20% by weight and especially from 0.5 to 10% by weight, based on the total weight of the composition, and the cosmetic preparations contain at least one cationic benzotriazole from 0.05–20% by weight, preferred from 0.1–20% by weight, based on the total weight of the composition. Typical cosmetic formulations containing uncharged and/or cationic benzotriazoles and/or antioxidants alone or in combinations are rinse-off products (e.g. shampoos, hair rinses, conditioners etc.), Suitable cosmetic formulations are:

cosmetic hair-treatment preparations, e.g. hair-washing preparations in the form of shampoos and conditioners, hair-care preparations, e.g. pre-treatment preparations or leave-on products such as sprays, creams, gels, lotions, mousses and oils, or hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellant gas or pump-action spray) or an aerosol, in the form of a foam, or in the form of a paste.

Of special importance as cosmetic preparations for the hair are the above-mentioned preparations for hair treatment, especially hair-washing preparations in the form of shampoos, hair conditioners, hair-care preparations, e.g. pre-treatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocoamidopropyl betaine, 3.0% by weight of sodium chloride, and water ad 100%.

Any known process suitable for the preparation of microparticles can be used for the preparation of the micronised UV absorbers, for example:

wet-grinding with a hard grinding medium, for example zirconium silicate and a protective surfactant or a protective polymer in water or in a suitable organic solvent;

spray-drying from a suitable solvent, for example aqueous suspensions or suspensions containing organic solvents, or true solutions in water, ethanol, dichloroethane, toluene or N-methylpyrrolidone etc.;

by the expansion according to the RESS process (Rapid Expansion of Supercritical Solutions) of supercritical fluids (e.g. $CO_2$) in which the UV filter or filters is/are dissolved, or the expansion of fluid carbon dioxide together with a solution of one or more UV filters in a suitable organic solvent;

by reprecipitation from suitable solvents, including supercritical fluids (GASR process=Gas Anti-Solvent Recrystallisation/PCA process=Precipitation with Compressed Anti-solvents).

As grinding apparatus for the preparation of the micronised organic UV absorbers there may be used, for example, a jet mill, ball mill, vibratory mill or hammer mill, preferably a high-speed mixing mill. The grinding is preferably carried out with a grinding aid, for example an alkylated vinylpyrrolidone polymer, a vinylpyrrolidone/vinyl acetate copolymer, an acyl glutamate, an alkyl polyglucoside, ceteareth-25 or a phospholipid.

The micronised UV absorbers so obtained usually have an average particle size that is from 0.02 to 2 μm, preferably from 0.05 to 1.5 μm, and more especially from 0.1 to 1.0 μm.

The UV absorbers can also be used dry in powder form. For that purpose the UV absorbers are subjected to known grinding methods, such as vacuum atomization, countercurrent spray-drying etc. Such powders have a particle size of from 0.1 μm to 2 μm. To avoid the occurrence of agglomeration, the UV absorbers can be coated with a surface-active compound prior to the pulverisation process, for example with an anionic, non-ionic or amphoteric surfactant, e.g. a phospholipid or a known polymer, such as PVP, or an acrylate. The colouring compositions for carrying out the method according to the invention may further comprise antimicrobial agents.

Typical antimicrobial preservatives and antimicrobial actives used in formulations (in most cases the INCI name of the antimicrobial substances is mentioned):

formaldehyde and paraformaldehyde, hydroxy biphenyls and its salts such as ortho-phenylphenol, zinc pyrithion, chlorobutanol, hydroxy benzoic acids and their salts and esters such as methyl paraben, ethyl paraben, propyl paraben, butyl paraben, dibromo hexamidine and its salts including isothionate (4,4'-hexamethylenedioxy-bis(3-bromo-benzamidine) and 4,4'-hexamethylenedioxy-bis(3-bromo-benzamidinium 2-hydroxyethanesulfonate), mercury, (aceto-O)phenyl (especially phenyl mercuric acetate) and Mercurate(2-),(orthoborate(3-)-O)phenyl, dihydrogene (especially phenyl mercuric borate), 1,3-bis (2-ethylhexyl)-hexahydro-5-methyl-5-pyrimidine (Hexetidin), 5-bromo-5-nitro-1,3-dioxan, 2-bromo-2-nitro-1,3-propandiol, 2,4-dichlorobenzyl alcohol, 3,4,4' trichlorocarbanilide (Trichlorcarban), p-chloro-m-cresol, 2,4,4'-trichloro 2-hydroxy diphenylether (triclosan), 4,4'-dichloro 2-hydroxy diphenylether, 4-chloro-3,5-dimethylphenol (Chloroxylenol), imidazolidinyl urea, poly-(hexamethylene biguanide) hydrochloride, 2-phenoxy ethanol (phenoxyethanol), hexamethylene tetramine (Methenamine), 1-(3-chloroallyl)-3,5,7-triaza-1-azoniaadamantanchloride (Quaternium 15), 1-(4-chlorophenyoxy)-1-(1-imidazolyl)3,3-dimethyl-2-butanone (Climbazole), 1,3-bis(hydroxymethyl)-5,5-dimethyl-2,4-imidazolidinedione (DMDM hydantoin), benzyl alcohol, 1,2-dibromo-2,4-dicyano butane, 2,2' methylene-bis(6-bromo-4-chloro phenol) (bromochlorophene), methylchloroisothiazolone, methylisothiazolone, octylisothiazolone, benzylisothiazolone, 2-benzyl-4-chlorophenol (Chlorophenone), chloracetamide, chlorhexidine, chlorhexidine acetate, chlorhexidine gluconate, chlorhexidine hydrochloride, 1-phenoxy-propane-2-ol (phenoxyisopropanol), 4,4-dimethyl-1,3-oxazolidine (dimethyl oxazolidine), diazolidinyl urea, 4,4'-hexamethylenedioxybisbenzamidine and 4,4'-hexamethylenedioxybis(benzamidinium-2-hydroxyethanesulfonate), glutaraldehyde (1,5-pentanedial), 7-ethylbicyclooxazolidine, 3-(4-chlorophenoxy)-1,2-propandiol (chlorophenesin), phenylmethoxymethanol and ((phenylmethoxy)methoxy)-methanol (benzylhemiformal), N-alkyl (C12–C22)trimethyl ammoniumbromide and -chloride (cetrimonium bromide, cetrimonium chloride), benzyldimethyl-(4-(2-(4-(1,1,3,3-tetramethylbutyl)-phenoxy)-ethoxy)-ethyl)-ammoniumchloride (benzethonium chloride), Alkyl-($C_8$–$C_{18}$)-dimethyl-benzylammonium chloride, -bromide and saccharinate (benzalkonium chloride, benzalkonium bromide, benzalkonium saccharinate), benzoic acid and its salts and esters, propionic acid and its salts, salicylic acid and its salt, sorbic acid and its salts, sodium iodiate, inorganic sulfites and bisulfites such as sodium sulfite, dehydroacetic acid, formic acid, mercurate(1-ethyl)2-mercaptobenzoate(2-)-O,S-,hydrogene (Thiomersal or Thiomerosal), 10-undecylenic acid and its salts, octopirox (piroctone olamine), sodium hydroxy methyl-aminoacetate (sodium hydroxymethylglycinate), 3-iodo-2-propynyl butylcarbamate, 10-undecylenic acid, sulfur.

Combinations with natural antimicrobials or chemically modified natural substances with antimicrobial activities such as chitosans and chitosan derivatives, farnesol, plant extracts such as clove oil, blue cypres oil etc. can be also used.

For use on human hair, the dyeing compositions can usually be incorporated into an aqueous cosmetic carrier. Suitable aqueous cosmetic carriers include, for example, creams, sprays, emulsions, gels, powders and also surfactant-containing foaming solutions, e.g. shampoos or other preparations, that are suitable for use on keratin-containing fibers. Such forms of use are described in detail in Research Disclosure 42448 (August 1999). If necessary, it is also possible to incorporate the dyeing compositions into anhydrous carriers, as described, for example, in U.S. Pat. No. 3,369,970, especially column 1, line 70 to column 3, line 55. The dyeing compositions according to the invention are also excellently suitable for the colouring method described in DE-A-3 829 870 using a colouring comb or a colouring brush.

Further carriers for dying compositions are for example described in "Dermatology", edited by Ch. Culnan, H. Malbach, Verlag Marcel Dekker Inc., New York, Basle, 1986, Vol. 7, Ch. Zviak, The Science of Hair Care, chapter 7, pages 248–250, especially on page 243, line 1 to page 244, line 12.

Suitable formulations of cationic dyes, which can be used in the colouring compositions for carrying out the method according to the invention are described for example in in WO 95/01772, especially on page 11, line 29 to page 12, line 7, or in WO 01/66646, especially on page 7, line 1 to page 22, and preferred from page 16, line 20 to page 22, or direct dyes as described in DE-A-19 713 698, especially page 3, line 51 to page 4, line 29 and page 4, line 65 to page 5, line 60, or direct dyes and oxidizing agent as described in WO 97/20545, especially on page 9, line 1 to page 11, line 4, in particular on page 11, line 6 to page 13, line 19.

Preferred formulations of cationic dyes with other dyes, which can be used in the colouring compositions for carrying out the method according to the invention, are:

combinations of Pyrazolo-[1,5-a]-pyrimidines with at least one cationic dye as described in EP 998,908, especially on page 47, line 3 to page 49, line 26, and preferred on page 51, line 4 to page 52, line 5, or combinations of cationic dyes as described in FR-2788432, especially on page 53, line 1 to page 63, line 23, especially a combination of cationic dyes with Arianors in FR-2788432, especially on pages 51 to 52, or especially a combination with at least one Basic Brown 17, Basic brown 16, Basic Red 76 and Basic Red 118, and/or at least one Basic Yellow 57, and/or at least one Basic Blue 99, or combinations of direct dyes and/or an oxidation dye and oxidizing agents in the form of permanent-wave fixing solution, especially with direct dyes as described in DE-A-19 713 698, especially page 4, line 65 to page 35, line 59, or combinations of cationic dyes and an oxidation dye of the developer compound type and oxidizing agents as described in EP 850 638, especially on page 2, lines 3 to 12 and line 30 to page 14, and page 28, line 35 to page 30, line 20, preferred on page 30, line 25 to page 32, line 30, or ready-to-use dyeing compositions and multicompartment device for dyeing keratin fibers comprising combinations of an extemporaneous mixture of a composition (A) containing one or more oxidation dye precursors and optionally one or more couplers, and of a composition (B), in powder form, containing one or more direct dye, preferably cationic, optionally dispersed in an organic pulverulent excipient and/or a mineral pulverulent excipient, and a composition (C) containing one or more oxidizing agent as described in U.S. Pat. No. 6,190,421, especially in column 2, line 20 to line 31 in column 7, line 15 to column 8, line 43, and preferably in column 8, line 55 to column 9, line 56, and preferably with direct dyes as described in column 5, line 30 to column 7, line 14, or a ready-to-use composition comprising, at least one oxidation base, at least one cationic direct dye and at least one enzyme of 2-electron oxidoreductase type in the presence of at least one donor for the said enzyme as described in U.S. Pat. No. 6,228,129, especially in column 2, line 16 to column 25, line 55, and a multicompartment dyeing device as described in column 26, lines 13 to 24, especially in column 26, line 26 to column 27, line 9, or a ready-to-use composition comprising compositions of at least one direct cationic dye and at least one nitrated benzene dye as described in WO 99/20235 especially on page 1, line 25 to page 8, line 5, and on page 30, line 17 to page 34 line 25, with cationic direct dyes as described on page 8, line 12 to page 25 line 6, and a multi-compartment dyeing device as described on page 35, lines 21 to 27, especially on page 36, line 1 to page 37, or a ready-to-use composition or a multi-compartment dyeing device comprising compositions of at least one direct cationic dye and at least one autooxidisable oxidation dye, especially benzene, indol and indoline derivatives as described in WO 99/20234, especially on page 26, line 5 to page 32, line 18, or oxidation dyeing compositions of at least one direct dye and at least one meta-Aminophenol derivative and at least one developer compound and an oxidizing agent as described in EP 850 636, especially on page 18, line 1 to page 22, line 11, or oxidation dyeing compositions of at least one direct dye and at least one developer compound selected from the group of para-Phenylenediamine derivatives and Bis-Phenylalkylenediamine and, and at least one coupler compound selected from the group of meta-Diphenols and an oxidizing agent, as described in EP-A-850 637, especially on page 19, line 24 to page 22, line 57, cationic dye and e.g. a pyrazolo-(1,5-a)-pyrimidine derivatives, as described in EP 998 908, especially on page 47, line 25 to page 50, line 29, or oxidative dye precursors (unsaturated aldehyde and coupler compounds), as described in German Patent Application 197 172 24, especially on page 3, line 36 to page 9 line 64.

Cationic dyes may be present in the colouring compositions for carrying out the method according to the invention preferably in an amount of from 0.001% to 5%, especially from 0.01% to 1%, based on the total dyeing composition.

The pH value of the ready-to-use dyeing preparations is usually from 2 to 11, preferably from 5 to 10.

The constituents of the aqueous carrier are used in the colouring compositions for carrying out the method according to the invention in the amounts customary for that purpose; for example emulsifiers may be used in concentrations of from 0.5 to 30% by weight and thickeners in concentrations of from 0.1 to 25% by weight of the total dyeing composition.

If direct dyes are used together with oxidation dyes, they may be stored separately or together.

It is preferred to store the oxidation dyes and direct dyes, which are not stable to reduction, separate They may be stored in a liquid to paste-like preparation (aqueous or non-aqueous) or in the form of a dry powder.

When the dyes and adjuvants are stored together in a liquid preparation, the preparation should be substantially anhydrous in order to reduce reaction of the compounds.

When they are stored separately, the reactive components are intimately mixed with one another only immediately before use. In the case of dry storage, before use a defined amount of hot (from 50 to 80° C.) water is usually added and a homogeneous mixture prepared.

One preferred method of applying direct dyes containing formulations on hair is by using a multi-compartment dyeing device or "kit" or any other multi-compartment packaging system, as described for example in WO 97/20545 on page 4, line 19 to line 27.

The colouring compositions for carrying out the method according to the invention may combined with a suitable ready-to-use composition for the oxidation dyeing of keratin fibers, in particular human keratin, comprising an oxidizing agent, at least one direct dye and at least one oxidation dye precursor, as described in U.S. Pat. No. 6,190,421, in column 1, line 65 to column 3, line 65, especially in column 10, line 62 to column 12, line 65.

Preferably, such a ready-to-use composition is prepared according to a first preferred embodiment by a process which comprises a preliminary step which involves separately storing, on the one hand, a composition (A) comprising, in a medium which is suitable for dyeing, at least one developer compound, especially selected from para-phenylenediamines and bis(phenyl)alkylenediamines, and the acid-addition salts thereof, at least one coupler, especially selected from meta-phenylenediamines and the acid-addition salts thereof, and at least one cationic direct dye, on the other hand, a composition (B) containing, in a medium which is suitable for dyeing, at least one oxidizing agent and mixing them together at the time of use before applying this mixture to the keratin fibers.

According to a second preferred embodiment for the preparation of the ready-to-use dye composition, the process includes a preliminary step which involves separately storing, on the one hand, a composition (A) comprising, in a medium which is suitable for dyeing, at least one developer compound, especially selected from para-phenylenediamines and bis(phenyl)alkylenediamines, and the acid-addition salts thereof, at least one coupler compound, especially selected from meta-phenylenediamines and the acid-addition salts thereof; on the other hand, a composition (A') comprising, in a medium which is suitable for dyeing, at least one cationic direct dye and, lastly, a composition (B) containing, in a medium which is suitable for dyeing, at least one oxidizing agent as defined above, and mixing them together at the time of use before applying this mixture to the keratin fibers.

The composition (A') used according to this second variant of the process in accordance with the invention can optionally be in powder form, the cationic direct dye(s) in accordance with the invention itself (themselves) constituting, in this case, all of the said composition (A') or optionally being dispersed in an organic and/or inorganic pulverulent excipient.

When it is present in the composition A', the organic excipient can be of synthetic or plant origin and is selected in particular from crosslinked and non-crosslinked synthetic polymers, polysaccharides such as celluloses and modified or unmodified starches, as well as natural products containing them such as sawdust and plant gums (guar gum, carob gum, xanthan gum, etc.).

When it is present in the composition (A'), the inorganic excipient can contain metal oxides such as titanium oxides, aluminium oxides, kaolin, talc, silicates, mica and silicas.

An very suitable excipient in the colouring compositions for carrying out the method according to the invention is sawdust.

The powdered composition (A') can also contain binders or coating products in an amount which preferably does not exceed approximately 3% by weight relative to the total weight of the said composition (A').

These binders are preferably selected from oils and liquid fatty substances of inorganic, synthetic, animal or plant origin.

The composition (A') may optionally also contain other adjuvants, in powdered form, in particular surfactants of any kind, hair conditioners such as, for example, cationic polymers, etc.

Another subject of the invention is a multi-compartment dyeing device or "kit" or any other multi-compartment packaging system, as described for example in U.S. Pat. No. 6,228,129, especially in column 26, lines 13 to 24, especially in column 26, line 26 to column 27, line 9, or. A first compartment which contains the composition (A) as defined above, an optional second compartment contains the composition (A) as defined above, when it is present, and a third compartment contains the oxidizing composition (B) as defined above. These devices can be equipped with means which allow the desired mixture to be applied to the hair, such as the devices described in French patent FR-2,586,913, the disclosure of which is specifically incorporated by reference herein.

An oxidizing agent, which may be added to the colouring compositions for carrying out the method according to the invention containing composition, comprises an oxidizing agent and a base.

Further, this composition comprises for this oxidizing agent containing composition customary adjuvant and additives.

The formulations are for example a solution, especially a thickened watery or watery alcoholic solution, a cream, foam, a gel, a powder or an emulsion.

In general, preference is given to a cream formulation, a gel formulation or a foam formulation, and especially a foam formulation.

But, if stability- or solubility-problems arise it may of advantage to use powder formulation as for example described in DE 197 13 698, page 2, line 26 to 54 and page 3, line 51 to page 4, line 25, and page 4, line 41 to page 5 line 59.

The oxidizing agent (calculated as hydrogen peroxide) is present in this composition in 0.5 to 12% by weight, in particular from 1 to 6% by weight based on the totals weight of the oxidizing agent containing composition.

The pH-value of the oxidizing agent containing composition is usually about 2 to 7, and in particular about 3 to 6.

An oxidizing agent free composition, which may be added to the colouring compositions for carrying out the method according to the invention, comprises a developer compound and a coupler compound and a reduction agent, or a developer compound or/and optionally a reduction agent, or a coupler compound and a reduction agent.

Further, an oxidizing agent free composition may additionally comprise a direct dye as for example described in German Patent Application 199 59 479, column 3, line 12 to line 16.

Additionally, the oxidizing agent free composition usually comprises customary adjuvant and additives. Preferred are those, which are described in German Patent Application, in column 3, line 17 to line 41.

The pH-value of the oxidizing agent free composition is usually about 3 to 11, and in particular about 5 to 10, and most particular about 9 to 10.

For adjusting the pH-value organic or inorganic acids, as for example described in German Patent Application 199 59 479, column 3, line 46 to line 53 are suitable.

The colouring compositions for carrying out the method according to the invention may also be combined with hair dye compositions comprising an acid dye. Hair dye compositions comprising an acid dye are known. For example, they are described in "Dermatology", edited by Ch. Culnan, H. Maibach, Verlag Marcel Dekker Inc., New York, Basle, 1986, Vol. 7, Ch. Zviak, The Science of Hair Care, chapter 7, pages 248–250, especially on page 253 and 254.

The hair dye compositions comprising an acid dye have a pH of 2–6, preferably 2–5, more preferably 2.5–4.0. If the pH is too low, the resulting composition may roughen the hair, scalp and hand skin due to an acid component in some cases. If the pH is too high, the penetration accelerating effect on the acid dye is lowered.

The colouring method according to the present invention may also readily be used in combination with other dyes and/or adjuvants used in the colouring of hair, for example acid dye and an alkylene carbonate, as described in U.S. Pat. No. 6,248,314, especially in examples 1 and 2, or acid hair dye compositions comprise various kinds of organic solvents represented by benzyl alcohol as a penetrant solvent have good penetrability into hair, as described in Japanese Patent Application Laid-Open Nos. 210023/1986 and 101841/1995, or acid hair dye compositions with a water-soluble polymer or the like to prevent the drooping of the hair dye composition, as described for example in Japanese Patent Application Laid-Open Nos. 87450/1998, 255540/1997 and 245348/1996, or acid hair dye compositions with a water-soluble polymer of aromatic alcohols, lower alkylene carbonates, or the like as described in Japanese Patent Application Laid-Open No. 53970/1998 and Japanese Patent Publication No. 23911/1973.

Preferred keratin fibers are human hair.

The dyes or dye precursors are suitable for all-over colouring of the hair, that is to say when colouring the hair on a first occasion, and also for re-colouring subsequently, or colouration of locks or parts of the hair.

The dyes or dye precursors are applied to hair for example through massage in by hand, a comb, a brush, or a bottle, or a bottle, which is combined with a comb or a nozzle.

In general, the dyes or dye precursors are applied to the hair in a formulation with further components, like adjuvants or additional dyes or dye precursors.

After the application of the dyeing composition the dyed hair is customary rinsed. Customary, the rinsing is conducted with water.

In a suitable embodiment of the processes of the present invention for dyeing human hair, the dyeing composition is not rinsed off, but washed off with a commercially available hair shampoo.

In general, the dyed hair is dried after rinsing and/or washing.

Customary, drying is conducted with hot air by means of a drier or the like, since color migration to clothes and the like becomes scarcely caused.

In the context of the present invention, the expression "a further dye", denotes preferably an oxidation dye, a diazotised compound, a capped diazotised compound and/or coupler compound, or acid dye, especially selected a cationic, anionic or uncharged direct dye.

A very suitable process for dyeing keratin fibers comprise contacting the keratin fibers under alkaline conditions with at least one capped diazotized compound and a coupler compound, with the proviso that the pH is adjusted in the range from 2 to 6 in the last process step.

Adjusting the pH is achieved in conventional manner by adding an acid as described for example in EP 962218, especially on page 3, lines 12 to 16.

Acids are for example tartaric acid or citric acid, a citric acid gel, a suitable buffer solution with optionally an acid dye.

Preferred technical forms of acids are a solution, a gel, a cream, a foam, a conditioner, a emulsion, a shampoo and more preferred a shampoo or a conditioner.

In the context of the present invention, the expression "alkaline condition", denotes to all process steps without those wherein acid conditions are explicitly described.

All processes for dyeing keratin fibers, in particular human hair, usually comprise after contacting the keratin fiber with a dye and/or optionally or an oxidizing agent a) leaving the fibers to stand, and
b) then rinsing the fibers.

The process for dyeing keratin fibers, in particular human hair, with direct dyes comprises a) contacting the keratin fibers with a direct dye.

The process for dyeing is for example described in WO 01/66646 on page 15, line 32 to page 16, line 2.

Usually, the dyeing compositions are usually applied to the hair in an amount of from 50 to 100 g.

This composition is left on the fiber at 15 to 45° C. for 5 to 30 minutes, and in particular for 10 to 20 minutes at 20 to 30° C.

The method of colouring according to the invention in combination with at least one direct dye may further concerns a process for dyeing keratin fibres comprises
   a) contacting the keratin fibers with at least one direct dye, a base and an oxidizing agent.

Compositions comprising at least one direct dye and an oxidizing agent, are for example described in WO 97/20545, on page 3, line 24 to page 11, line 4, and especially on page 4, line 9 to 17.

The composition comprising at least one direct dye, a base and an oxidizing agent is prepared by mixing at least one direct dye and a base, and then just before the dyeing of the hair, adding an oxidizing agent.

Alternatively, the oxidizing agent can be applied simultaneously with a composition comprising at least one dye and a base.

Preferably, the process for dyeing keratin fibres with at least on direct dye comprises using a multi-compartment dyeing device or 'kits' as described for example in WO 97/20545, especially on page 4, line 19 to line 27.

Suitable processes for enlightening dyeing, which can be used in combination with the method for colouring according to the invention are described in WO 97/20545, on page 11 to page 13.

Suitable processes for dyeing with cationic dyes, which can be combined with the method of colouring according to the present invention, are described
   in WO 95/01772, especially on page 10, line 24 to page 11, line 16, and especially on page 11, line 29 to page 28, or
   in WO 01/66646, especially on page 1, line 18 to page 3, line 16, and preferred from page 16, line 20 to page 22, or
   in EP 970 685, especially on page 50, lines 15 to 43, and preferred from page 50, line 46 to page 51, line 40, or
   in DE-A-19 713 698, especially page 5, lines 26 to 60, or
   a process of dyeing with direct dyes and oxidizing agent is described in WO 97/20545, especially on page 10, line 10 to page 11, line 55 and preferably on page 11, line 6 to page 13, line 19.

Suitable processes for dyeing with combinations of cationic dyes and other dyes, which can be combined with the method of colouring according to the present invention, are:
   mixtures of at least two cationic dyes as described in WO 95/01772, especially on page 11, lines 1 to 15, or
   combinations of Pyrazolo-[1,5-a]-pyrimidines with at least one cationic dye as described in EP 998,908, especially on page 50, lines 15 to 28, or
   combinations of cationic dyes as described in FR-2788432, especially on page 49, line 28 to page 52, and preferred on page 50, lines 16 to 28, or
   combinations of direct dyes and/or an oxidation dye and oxidizing agents in the form of permanent-wave fixing solution, especially with direct dyes as described in DE-A-19 713 698, especially on page 2, lines 12 to 23, especially on page 4, line 65 to page 5, line 59, or
   combinations of cationic dyes and an oxidation dye of the developer compound type and oxidizing agents as described in EP 850 638, especially on page 29, line 42 to page 30, line 20 and preferred on page 30, line 25 to page 32, line 30, or
   combinations of an extemporaneous mixture of a composition (A) containing one or more oxidation dye precursors and optionally one or more couplers, and of
   a composition (B), in powder form, containing one or more direct dye, preferably cationic, optionally dispersed in an organic pulverulent excipient and/or a mineral pulverulent excipient, and a composition (C) containing one or more oxidizing agent as described in U.S. Pat. No. 6,190,421, especially in column 8, lines 43 to 52, and preferably in column 8, line 55 to column 9, line 55, or
   a ready-to-use composition comprising, at least one oxidation base, at least one cationic direct dye and at least one enzyme of 2-electron oxidoreductase type in the presence of at least one donor for the said enzyme as described in U.S. Pat. No. 6,228,129, especially in column 25, line 56 to column 27, line 9, or
   a ready-to-use composition or multi-compartment dyeing device comprising compositions of at least one direct cationic dye and at least one nitrated benzene dye as described in WO 99/20235 on page 34, line 27 to page 37, or
   a ready-to-use composition or multi-compartment dyeing device comprising compositions of at least one direct cationic dye and at least one autooxidisable oxidation dye, especially benzene, indol and indoline derivatives as described in WO 99/20234, especially on page 32, line 20 to page 35, oxidation dyeing compositions of at least one direct dye and at least one meta-Aminophenol derivative and at least one developer compound and an oxidizing agent as described in EP 850 636, especially on page 18, line 1 to page 22, line 11, or
   oxidation dyeing compositions of at least one direct dye and at least one developer compound selected from the group of para-Phenylenediamine derivatives and Bis-Phenylalkylenediamine and, and at least one coupler compound selected from the group of meta-Diphenols and an oxidizing agent, as described in EP-A-850 637, especially on page 19, line 24 to page 22, line 57,
   cationic dye and e.g. a pyrazolo-(1,5-a)-pyrimidine derivatives, as described in EP 998 908, especially on page 47, line 25 to page 50, line 29, or
   arianors and/or oxidative dyes, as described in FR-2 788 432, especially on page 2, line 16 to page 3, line 16, and page 5, line 19 to page 14, line 8, and combinations with cationic dyes as described on page 14, line 23 and following, or
   oxidative dye precursors (unsaturated aldehyde and coupler compounds), as described in German Patent Application 197 172 24, especially on page 3, line 36 to page 9 line 64.

The method of colouring of keratin fibers, especially human hair, according to the present invention may combined with direct dyes and oxidative dyes.

The process for dyeing keratin fibers with direct dyes and oxidative dyes, in particular human hair, comprises
   a) contacting the keratin fibers with an oxidizing agent, optionally containing at least a direct dye,
   b) then contacting the keratin fibers with an oxidizing agent free composition, optionally containing at least a direct dye, or
   a) contacting the keratin fibers with an oxidizing agent free composition, optionally containing at least a direct dye,
   b) then contacting the keratin fibers with an oxidizing agent, optionally containing at least a direct dye.

The method of colouring according to the present invention may combined with a process for dyeing keratin fibers with direct dyes and oxidative dyes, which comprises a) contacting the keratin fibers with at least one direct dye,
b) then contacting the keratin fibers with an oxidizing agent free composition.

Such process is for example described in DE 199 41 450, especially on page 5, lines 50 to 58, and on page 8, line 31 to 46.

Oxidizing agent is usually applied in form of an oxidizing agent containing composition. Oxidizing agent free composition containing at least one coupler compound, at least one developer compound, a base and a reduction agent.

Customary, the oxidizing agent containing composition is evenly applied in a sufficient amount related to the amount of hair, usually with 30 to 200 g.

In general, the oxidizing agent containing composition is left on the fiber at 15 to 45° C. for 0 to 15 minutes, and in particular for 0 to 5 minutes.

Then the oxidizing agent free composition is applied to the hair.

In general, the direct dye and oxidizing agent free composition is left on the fiber at 15 to 50° C. for 5 to 45 minutes, and in particular for 10 to 25 minutes.

The coupler and developer compounds of the oxidizing agent free composition can be applied simultaneously or in succession. Preferred is a simultaneous application.

One preferred embodiment of the process is to wash the hair with shampoo and or a weak acid, such as citric acid or tartrate acid.

The direct dyes, which are stable to reduction can stored together with the oxidizing agent free compositions and are applicable as composition.

It is of advantage to prepare compositions of direct dyes, which are not stable to reduction, with oxidizing agent free compositions just before the dyeing process.

Further, a direct dye and an oxidizing agent free composition can be applied simultaneously or in succession.

A suitable process for the coloration of keratin fiber with direct dyes and oxidation dyes, which can be used in combination with the method of colouring according to the present invention, comprises
  a) mixing at least one direct dye and optionally at least one coupler compound and at least one developer compound, and an oxidizing agent, which optionally contains at least one direct dye, and
  b) then contacting the keratin fibers with the mixture as prepared in step a).

A further suitable process for the coloration of keratin fiber with direct dyes and oxidation dyes, which can be used in combination with the method of colouring according to the present invention, comprises
  a) mixing at least one autooxidable compound and at least one developer compound and at least one direct dye, and
  b) then contacting the keratin fibers with the mixture prepared in step a).

The direct dye is usually applied in form of a composition, comprising further adjuvants, in particular an aqueous composition.

In general the mixing is conducted just before contacting the keratin fibers. Usually, the mixture prepared in process step a) is evenly applied in a sufficient amount related to the amount of hair, usually with 30 to 200 g. In general, the mixture is left on the fiber at 15 to 45° C. for 0 to 50 minutes, and in particular for 30 to 45 minutes.

One preferred embodiment of the processes is to wash the hair with shampoo and or a weak acid, such as citric acid or tartrate acid, as for example described in EP 962218, especially on page 3, lines 9 to 18.

One suitable embodiment of the present invention concerns in addition to the method according to the present invention, the separate application of a direct dye an oxidation dye is for example as described in DE-A-19 713 698, especially page 4, line 65 to page 35, line 59, wherein the keratin fibres are contacted in a first step with a direct dye, especially in form of a tinting powder, and an oxidizing agent, and then, in a second step, with an oxidizing free composition, especially in form of a powder.

Further, it is possible to apply a for example a ready-to-use composition for the oxidation dyeing of keratin fibers, in particular human keratin fibers such as hair, as described in U.S. Pat. No. 6,190,421, in column 1, line 65 to column 3, line 65, especially in column 10, line 62 to column 12, line 65.

According to this process, the ready-to-use dye composition as defined above is applied to the fibers and is left on them for an exposure time preferably of from approximately 3 to approximately 40 minutes, more preferably from approximately 5 to approximately 30 minutes, after which the fibers are rinsed, optionally washed with shampoo, rinsed again and dried.

If unsaturated aldehydes are used as oxidative precursor dye together with a coupler compound no oxidizing agent is needed as described in German Patent Application 19 717 224.5. Nevertheless, it may be desirable to conduct the colouring in the presence of oxidizing agents, if lightening or a unified colouration of the keratin fiber is envisaged.

The process of dyeing keratin fibers with oxidative dye precursors, which can be used in combination with the method of colouring according to the present invention, comprises
  a) contacting the keratin fibers with an unsaturated aldehyde, a coupler compound and a direct dye.

In all above-cited dyeing processes it is also possible to apply a mixture of coupler compounds/and or developer compounds and/different direct dyes.

Another preferred embodiment of the processes for oxidative dyeing of keratin fibers, which can be used in combination with the method of colouring according to the present invention, comprise applying to the keratin fibers after contacting with an oxidizing agent free composition containing a coupler compound and a developer compound and optionally a direct dye with a further oxidizing agent free composition containing a coupler compound and a developer compound and optionally an oxidizing agent containing composition and optionally a direct dye by a pH range from 5 to 7, preferred from 6.5 to 7. In general the keratin fiber is not washed or rinsed afterwards as for example described in EP 962217, especially on page 3, lines 9 to 17.

The developer and coupler compounds can be applied separately, simultaneously or in succession.

In all above-cited dyeing processes with oxidation dye precursors it is also possible to apply a mixture of coupler compounds/and or developer compounds.

A more suitable process for the dyeing of keratin fibers with oxidative dyes, which can be used in combination with the method of colouring according to the present invention, comprises,
  a) contacting the keratin fibers with an oxidizing agent containing composition,
  b) then contacting the keratin fibers with an oxidizing agent free composition.

Such process is for example described in DE 19959479, especially in column 3, line 54 to column 4, line 8.

Usually, the oxidizing agent containing composition is evenly applied in a sufficient amount related to the amount of hair, usually with 30 to 200 g.

In general, the oxidizing agent containing composition is left on the fiber at 15 to 50° C. for 0 to 15 minutes, and in particular for 0 to 30 minutes.

Then the oxidizing agent free composition is applied.

Customary, the oxidizing agent free composition is left on the fiber at 15 to 50° C. for 5 to 45 minutes, and in particular for 10 to 25 minutes.

The coupler and developer compounds of oxidizing agent free compositions can be applied as an admixture, or separately simultaneously or in succession. Preferred is the application of an admixture.

One suitable embodiment of the processes is to wash the hair with shampoo and or a weak acid, such as citric acid or tartrate acid, as for example described in EP 962218, especially on page 3, lines 9 to 18.

A further suitable process for the coloration of keratin fiber with oxidation dyes, which can be used in combination with the method of colouring according to the present invention, comprises
  a) mixing at least one coupler compound and developer compound, and an oxidizing agent, and
  b) then contacting the keratin fibers with the mixture as prepared in step a).

A further suitable process for the coloration of keratin fiber with an oxidation dye, which can be used in combination with the method of colouring according to the present invention, comprises
  a) mixing an autooxidable compound and a developer compound, and
  b) then contacting the keratin fibers with the mixture prepared in step a).

Especially preferred is a process for dyeing keratin fibers, in particular human hair, with capped diazotised compounds, which comprises,
  a) contacting the keratin fibers, under alkaline conditions, with at least one capped diazotised compound and a coupler compound, and optionally an oxidising agent, and optionally in the presence of a further dye,
  b) then adjusting the pH in the range of 6 to 2 by treatment with acid, optionally in the presence of a further dye.

The capped diazotised compound and coupler compound and optionally the oxidizing agent, can be applied in any desired order successively, or simultaneously.

Preferably, however, the capped diazotised compound and the coupler compound are applied simultaneously, in a single composition.

Customary the dyeing composition is applied to the hair in an amount of from 50 to 100 g.

In the context of the present invention, the expression "alkaline conditions" denotes a pH in the range from 8 to 10, preferably 9–10, especially 9.5–10.

Adding bases, for example sodium carbonate, ammonia or sodium hydroxide, to the hair or to the dye precursors, the capped diazotised compound and/or the water-soluble coupling component, or to colouring compositions comprising the dye precursors, customarily achieve the alkaline conditions.

In the second stage, the diazotised compound and the coupler compound are then caused to react, preferably by lowering the pH to a value of from 6 to 2, especially from 3 to 4.

A preferred embodiment of all processes of the present invention for dyeing keratin fibers comprise contacting the keratin fibers under alkaline conditions with at least one capped diazotized compound and a coupler compound, with the proviso that the pH is adjusted in the range from 2 to 6 in the last process step.

Adjusting the pH is achieved in conventional manner by adding an acid as described for example in EP 962218, especially on page 3, lines 12 to 16.

Acids are for example tartaric acid or citric acid, a citric acid gel, a suitable buffer solution with optionally an acid dye.

Preferred technical forms of acids are a solution, a gel, a cream, a foam, a conditioner, a emulsion, a shampoo and more preferred a shampoo or a conditioner.

The ratio of the amount of alkaline colouring composition applied in the first stage to that of acid colouring composition applied in the second stage is preferably about from 1:3 to 3:1, especially about 1:1.

This first alkaline and then acid dyeing compositions each are left on the fiber at 15 to 45° C. for 5 to 60 minutes, and in particular for 5 to 45 minutes at 20 to 30° C.

In the methods according to the invention, whether or not colouring is to be carried out in the presence of a further dye will depend upon the colour shade to be obtained. In the context of the present invention, the expression "a further dye", denotes preferably an oxidation dye, a diazotised compound, a capped diazotised compound and/or coupler compound, or acid dye, especially selected a cationic, anionic or uncharged direct dye, especially a cationic dye selected from the group of the cationic dyes as described in WO 95/01772, especially on page 2, line 7 to page 4, line 1, and preferred on page 4, line 35 to page 8, line 21 with the given preferences, and as described in WO 01/66646, especially on page 1, line 18 to page 3, line 16, or a mixture of at least two cationic dyes as described in WO 95/01772, especially on page 8, line 34 to page 10, line 22.

A preferred embodiment of the process for dyeing keratin fibres with capped diazotised compounds and a coupler compound, comprises contacting the keratin fibres with more than one capped diazotised compound and/or more than one coupler compound.

Preferred is a process of the present invention for the coloration of keratin fiber with capped diazotised compounds comprises
  a) mixing, under alkaline conditions, at least one with capped diazotised compound and at least one coupler compound and at least one direct dye and optionally at least one developer compound; and an oxidizing agent, which optionally contains at least one direct dye, and
  b) then contacting the keratin fibers with the mixture as prepared in step a),
  c) then adjusting the pH in the range of 6 to 2 by treatment with acid, optionally in the presence of a further dye.

More preferred is a process for dyeing keratin fibres with at least one capped diazotized compound, which comprises
  a) mixing under alkaline conditions, at least one capped diazotized compound and at least one direct dye, a base and an oxidizing agent, and
  b) then contacting the keratin fibers with the mixture as prepared in step a),
  c) then adjusting the pH in the range of 6 to 2 by treatment with acid, optionally in the presence of a further dye.

Further, preferred is a process for the coloration of keratin fiber with capped diazotised compounds comprising
  a) mixing under alkaline conditions, at least one with capped diazotised compound and at least one coupler compound and optionally at least one direct dye and optionally at least one developer compound, and optionally at least one autooxidable compound, and b) then contacting the keratin fibers with the mixture prepared in step a), c) then adjusting the pH in the range of 6 to 2 by treatment with acid, optionally in the presence of a further dye.

A further suitable process for the two-step direct dyeing of keratin fibres, which can be used in combination with the method of colouring according to the present invention, is characterized in that, a) contacting the keratin fibers with an oxidizing agent or an oxidizing agent containing composition, b) then contacting the keratin fibers with at least one capped diazotised compound and at least a coupler compound and optionally a direct dye or/and optionally an oxidizing agent free composition, c) then adjusting the pH in the range of 6 to 2 by treatment with acid, optionally in the presence of a further dye.

or a) contacting the keratin fibers with at least one capped diazotised compound and a coupler compound and optionally a direct dye or/and optionally an oxidizing agent free composition, b) then contacting the keratin fibers with an oxidizing agent or an oxidizing agent containing composition, c) then adjusting the pH in the range of 5 to 2 by treatment with acid, optionally in the presence of a further dye.

d)

The present invention also concerns a process for the colouration of keratin fibers, especially human hair, with acid dyes, which can be used in combination with the method of colouring according to the present invention.

The process comprises additionally a) contacting the keratin fiber with an acid dye.

Customary, the dyeing composition comprising an acid dye is applied to the hair in an amount of from 50 to 100 g.

This in a composition is left on the fiber at 15 to 45° C. for 1 to 30 minutes, and in particular for 0 to 15 minutes at 20 to 30° C.

Preferably the hair is rinsed and than washed with shampoo and more preferably not rinsed, but washed with shampoo.

The shampoo used herein includes a shampoo comprising 5–20% of a usual anionic surfactant such as an alkylsulfate or polyoxyethylene alkylsulfate.

The invention relates also to colouring compositions for carrying out the method according to the invention, which compositions comprise a) at least one compound of formula (1), (2) and/or (3) indicated hereinbefore, b) a medium for adjusting the pH, c) water, and, optionally, d) further additives.

Further, the invention relates also to colouring compositions for carrying out the method according to the invention, which compositions comprise a) at least one compound of formula (1), (2) and/or (3) indicated hereinbefore, b) a medium for adjusting the pH, c) water, d) at least one coupling component, and, optionally, e) further additives, with the provisos that (i) if the water-soluble coupling component is

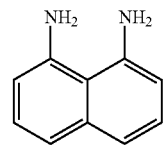

then the capped diazonium compound must not be

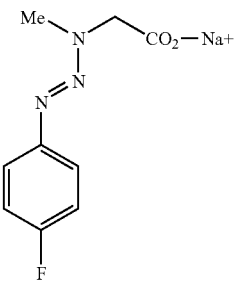

and (ii) if the water-soluble coupling component is

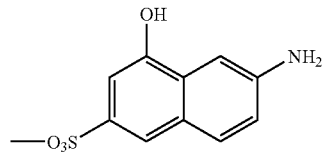

then the capped diazonium compound must not be

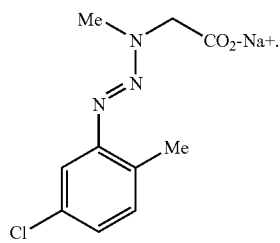

Further, the invention relates also to colouring compositions for carrying out the method according to the invention, which compositions comprise a) at least one compound of formula (1), (2) and/or (3) indicated hereinbefore, b) a medium for adjusting the pH, c) water, d) at least one water-soluble coupling component selected from the group consisting of acylacetarylamides, phenols, naphthols, pyridones, quinolones, pyrazoles, indoles, diphenylamines, anilines, aminopyridines, pyrimidones, naphthylamines, aminothiazoles, thiophenes or hydroxy-pyridines, which all may carry further substituents, for example amino, alkylamino, dialkylamino, halogen, alkyl, alkoxy, aryl, especially phenyl or naphthyl, or aryloxy, but especially a group imparting water solubility, e.g. hydroxy, carboxy or sulfo, and, optionally, e) further additives, with the provisos that
(i) if the water-soluble coupling component is

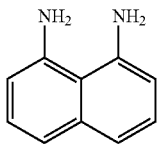

then the capped diazonium compound must not be

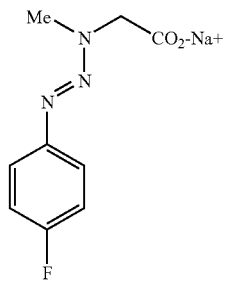

and
(ii) K the water-soluble coupling component is

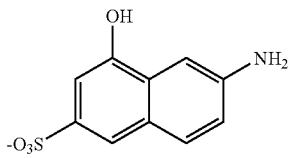

then the capped diazonium compound must not be

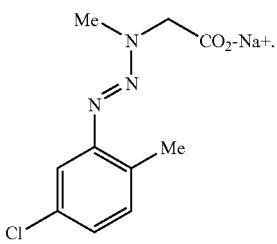

Especially preferred compositions comprise
a) at least one compound of formula (1), (2) and/or (3) indicated hereinbefore,
b) a medium for adjusting the pH,
c) water,
d) at least one water-soluble coupling component selected from the group consisting of acylacetarylamides, phenols, naphthols, pyridones, quinolones, pyrazoles, indoles, diphenylamines, anilines, aminopyridines, pyrimidones, naphthylamines, aminothiazoles, thiophenes or hydroxypyridines, which all may carry further substituents, for example amino, alkylamino, dialkylamino, halogen, alkyl, alkoxy, aryl, especially phenyl or naphthyl, or aryloxy, but especially a group imparting water solubility, e.g. hydroxy, carboxy or sulfo, e) a further dye, preferably an oxidation dye, or a cationic, anionic or uncharged direct dye, especially a cationic dye selected from the group of the cationic dyes as described in WO 95/01772 and WO 01/66646, and, optionally, f) further additives, with the provisos that
(i) if the water-soluble coupling component is

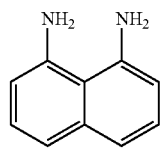

then the capped diazonium compound must not be

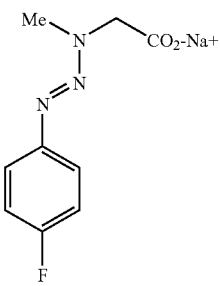

and
(ii) if the water-soluble coupling component is

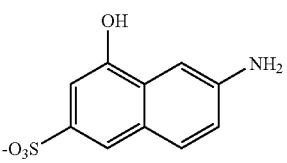

then the capped diazonium compound must not be

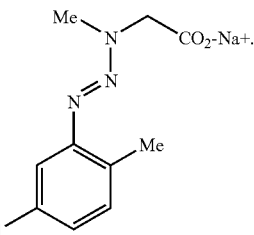

The colouring compositions used in accordance with the invention and the optionally used oxidation dye precursors may be stored either separately or together, either in a liquid to paste-like preparation (aqueous or non-aqueous) or in the form of a dry powder. When the components are stored together in a liquid preparation, the preparation should be substantially anhydrous in order to reduce reaction of the components. When they are stored separately, the reactive components are intimately mixed with one another only immediately before use. In the case of dry storage, before use a defined amount of hot (from 50 to 80° C.) water is usually added and a homogeneous mixture prepared.

The following Examples serve to illustrate the invention without limiting the invention thereto. Unless specified otherwise, parts and percentages relate to weight. The amounts of dye specified are relative to the material being coloured.

EXAMPLE 1

A) Preparation of Triazenes 43.4 g of 4-chloro-2-amino-1-methylbenzene are mixed with 81 g of 32% hydrochloric acid and cooled to 0° C. Then, over the course of one hour, 75 ml of 4N aqueous sodium nitrite solution are added dropwise, with stirring, the temperature being maintained at from 0 to 5° C. The resulting solution is then added dropwise, over the course of 15 minutes, to an aqueous solution of 30 g of sarcosine and 90 g of sodium carbonate in 250 ml of water at a temperature of 0–5° C. The resulting brown suspension is filtered, the residue is recrystallised from ethanol and dried in air. 66.2 g of 3-methyl-1-(5-chloro-2-methylphenyl)-3-(carboxylmethyl)triazene are obtained in the form of brownish-yellow powder. (Yield: 91%). The compound has the following formula and its $^1$H-NMR spectrum exhibits the chemical shifts indicated.

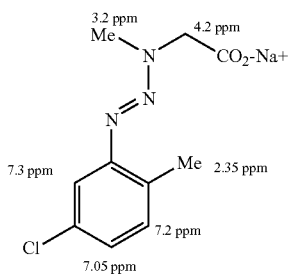

EXAMPLES 2 TO 4

Using a procedure analogous to that described in Example 1, the following compounds are prepared Colouring Method A:

A strand of bleached human hair is immersed, for 30 minutes at room temperature, in an aqueous solution containing 0.2M triazene and 0.2M coupling component, which has been adjusted to pH 10.0 using sodium carbonate, ammonia or NaOH. The strand is removed, excess solution is wiped off and the strand is immersed for 5 minutes in a pH 3 buffer solution containing 4% sodium citrate and 2% citric acid. The strand is then thoroughly rinsed using water and, where appropriate, a shampoo solution and is dried. Hair coloured in the shades mentioned is obtained, with outstanding fastness properties, especially fastness to washing properties.

Colouring Method B:

A strand of bleached human hair is immersed, for 30 minutes at room temperature, in an aqueous solution that contains 0.2M triazene, 0.2M coupling component and 0.2M of hydrogen peroxide (6%) and that has been adjusted to a pH in the range pH 9.8–10 using sodium carbonate, ammonia or NaOH. After contact for 5–30 minutes, there is applied to the strand, without its being rinsed, an amount, corresponding to the weight of triazene and coupling component originally used, of a mixture comprising 12.5% strength aqueous citric acid gel, which contains 0.1% by weight of a cationic dye selected from the group of the cationic dyes as disclosed in WO 95/01772 and in WO 01/66646. The strand is then combed through thoroughly, a pH of about 7 being obtained. After contact for 15 minutes, the treated strand is treated again with the above mixture comprising 12.5% strength citric acid gel and 0.1% by weight of a cationic dye selected from the group of the cationic dyes as disclosed in WO 95/01772 and in WO 01/66646 at pH 4 for 5 minutes, rinsed thoroughly with water and then dried. Hair is obtained with outstanding fastness properties, especially fastness to washing and fastness to shampooing properties.

Colouring Method C:

A strand of bleached human hair is immersed, for 30 minutes at room temperature, in an aqueous solution that contains 0.2M triazene, 0.2M coupling component and 0.2 mol of hydrogen peroxide (6%) and that has been adjusted to a pH in the range pH 9.8–10 using sodium carbonate, ammonia or NaOH. After contact for 5–30 minutes, there is applied to the hair, without its being rinsed, an amount, corresponding to the weight of triazene and coupling component originally used, of a 12.5% strength aqueous citric acid gel containing 0.1% by weight of a cationic dye selected from the group of the cationic dyes as disclosed in WO 95/01772 and in WO 01/66646 and 4% sodium citrate; the hair is combed through thoroughly, a pH of about 3 being obtained. Then, after a contact time of 5–30 minutes, the hair is rinsed thoroughly with water and dried. Hair is obtained with outstanding fastness properties, especially good fastening to washing properties.

Colouring Method D:

A strand of bleached human hair is immersed, for 30 minutes at room temperature, in an aqueous solution containing 0.2M triazene, 0.2M coupling component, 0.2 mol of hydrogen peroxide (6%) and from 0.1 to 1% by weight, based on the weight of the triazene and coupling component, of a cationic dye selected from the group of the cationic dyes as described in WO 95/01772 and in WO 01/66646. The strand is then adjusted to a pH in the range pH 9.8–10 using sodium carbonate, ammonia or NaOH. After contact for 5–30 minutes, there is applied to the hair, without its being rinsed, an amount, corresponding to the weight of triazene and coupling component originally used, of a 12.5% strength aqueous citric acid gel and 4% sodium citrate and the hair is combed through thoroughly, a pH of about 3 being obtained. Then, after a contact time of 5–30 minutes, the hair is rinsed thoroughly with water and dried. Hair is obtained with outstanding fastness properties, especially good fastness to washing properties.

| Triazene | Coupler | Hair colour |
|---|---|---|
| Example 5: | | carmine-red |
| Example 6: | | cherry-red |
| Example 7: | | reddish orange |
| Example 8: | | purple |

-continued
| Triazene | Coupler | Hair colour |
|---|---|---|
Example 9:
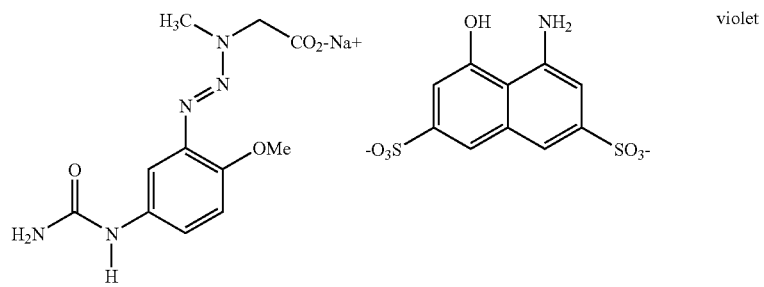
violet
Example 10:
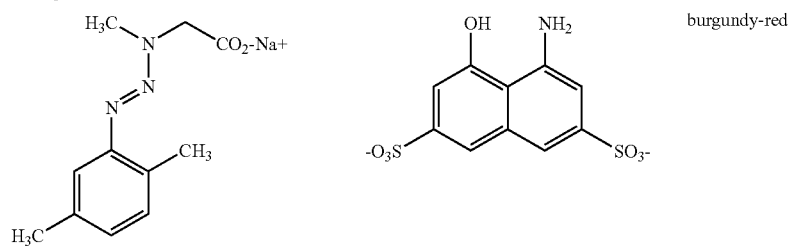
burgundy-red
Example 11:
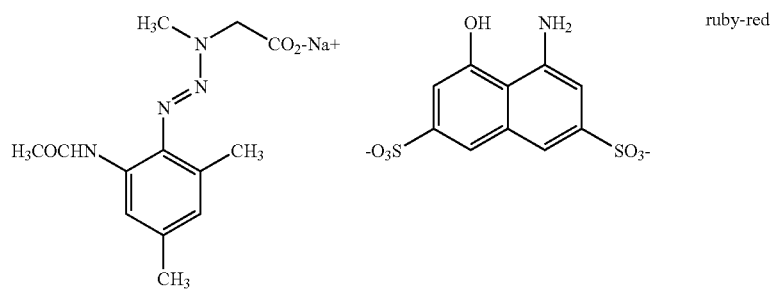
ruby-red
Example 12:
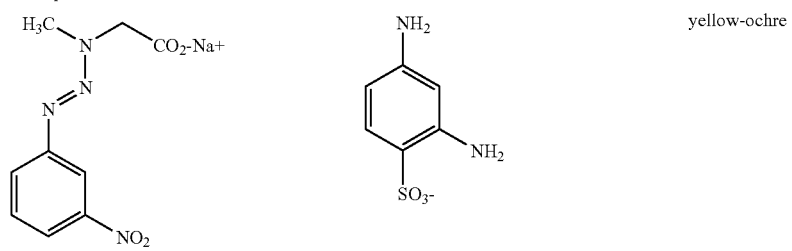
yellow-ochre
Example 13:
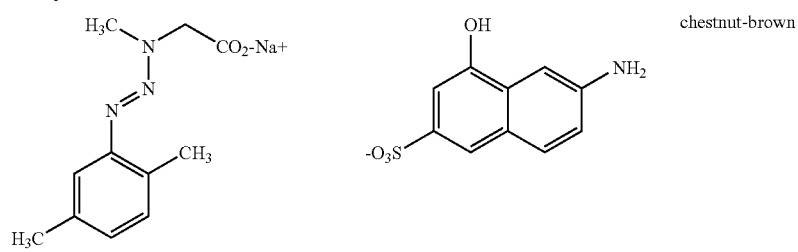
chestnut-brown -continued
| Triazene | Coupler | Hair colour |
|---|---|---|
| Example 14: 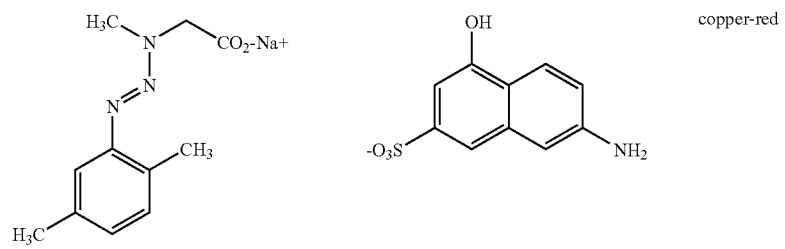 | | copper-red |
| Example 15: 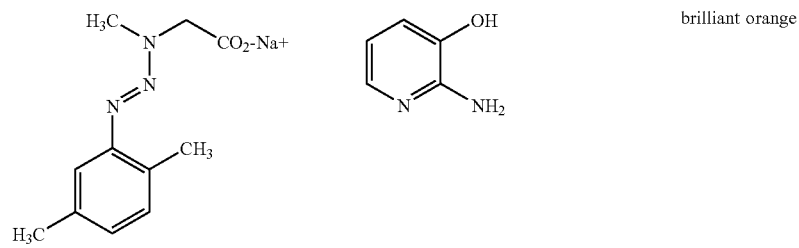 | | brilliant orange |
| Example 16: 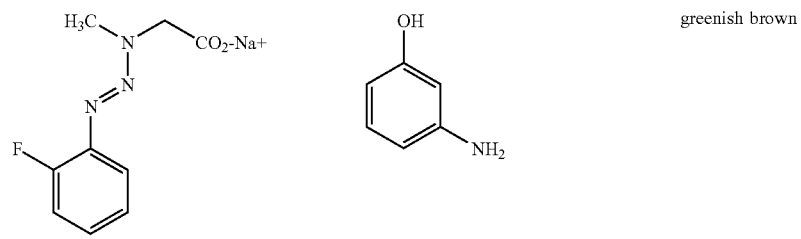 | | greenish brown |
| Example 17: 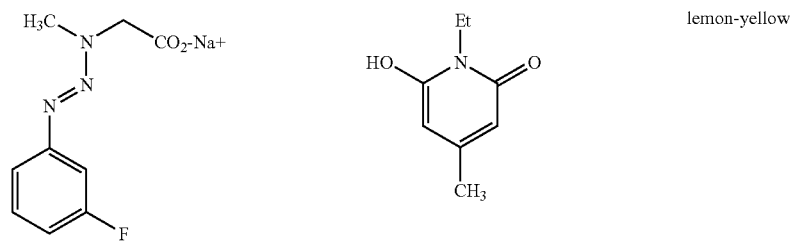 | | lemon-yellow |
| Example 18: 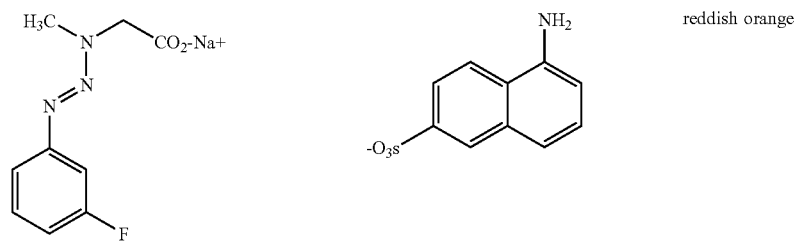 | | reddish orange |

-continued
| Triazene | Coupler | Hair colour |
|---|---|---|
| Example 19: 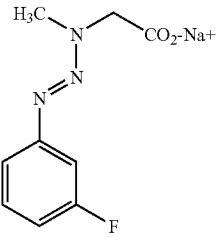 | 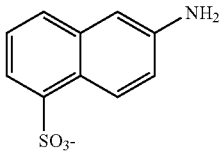 | golden-yellow |
| Example 20: 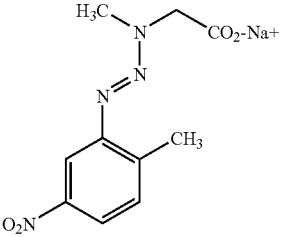 | 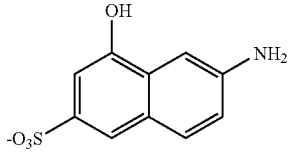 | copper-red |
| Example 21: 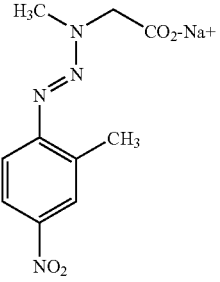 | 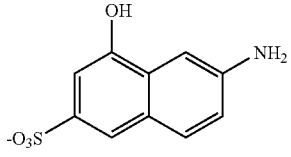 | copper-red |
| Example 22: 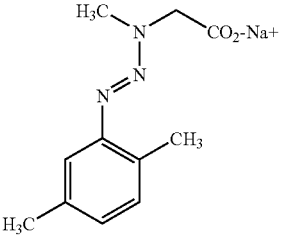 | 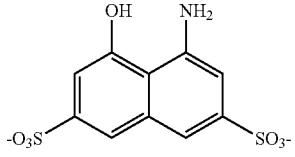 | rust-red |
| Example 23: 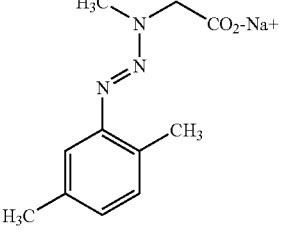 | 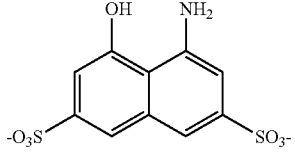 | wine-red |

-continued
| Triazene | Coupler | Hair colour |
|---|---|---|
| Example 24: 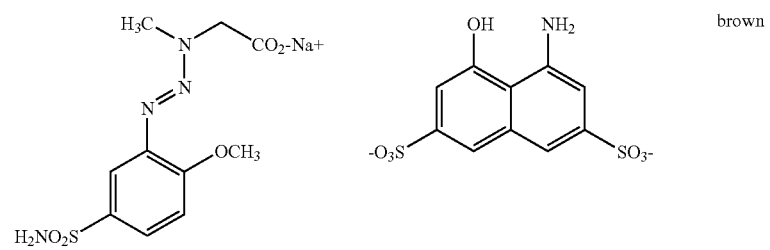 | | brown |
| Example 25: 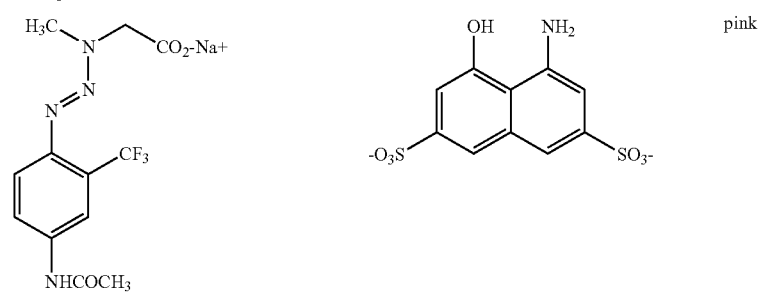 | | pink |
| Example 26: 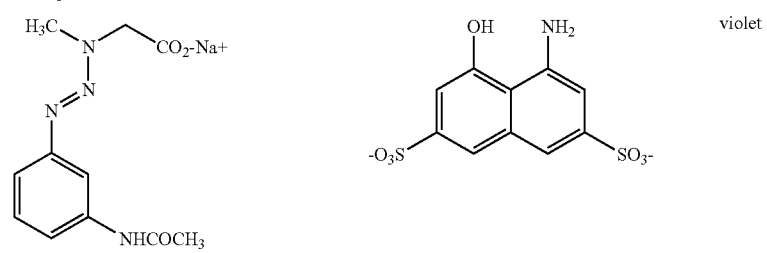 | | violet |
| Example 27: 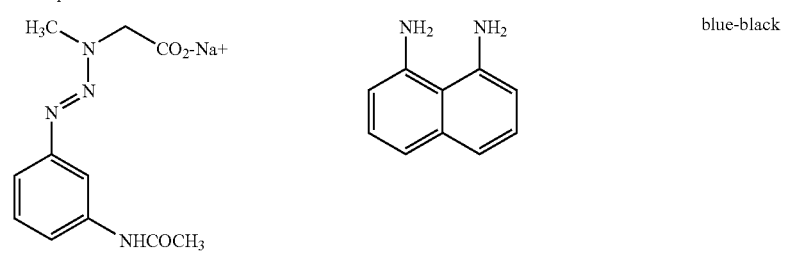 | | blue-black |
| Example 28: 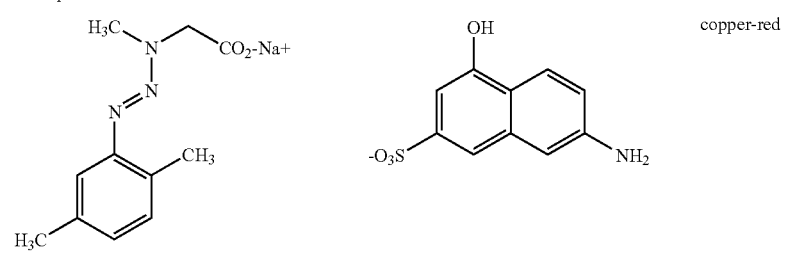 | | copper-red |

| Triazene | Coupler | Hair colour |
|---|---|---|
| Example 29: 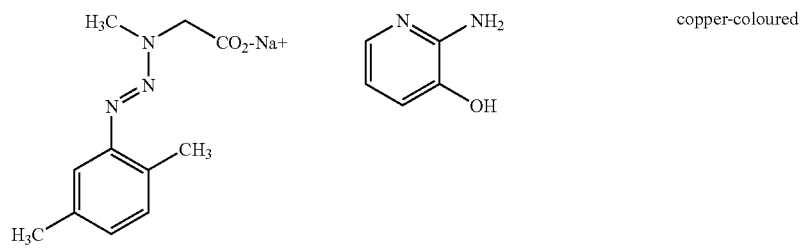 | | copper-coloured |
| Example 30: 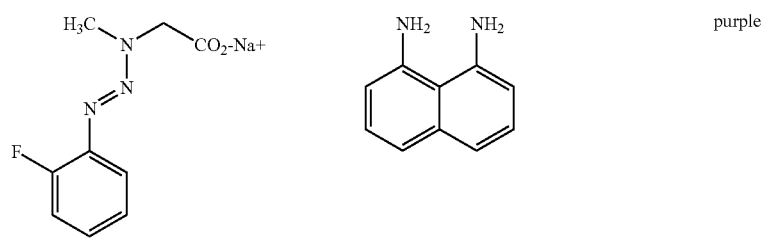 | | purple |
| Example 31: 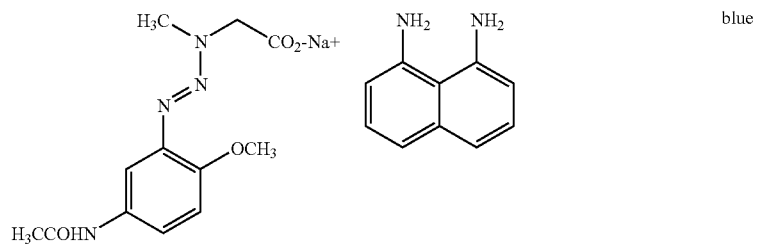 | | blue |
| Example 32: 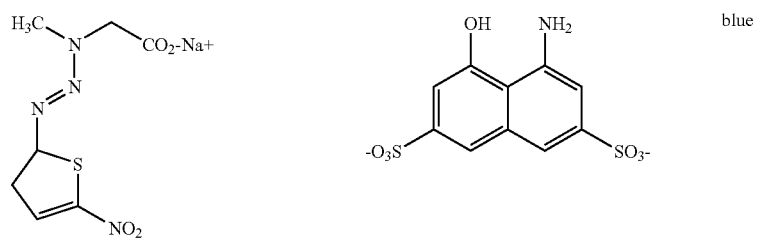 | | blue |
| Example 33: 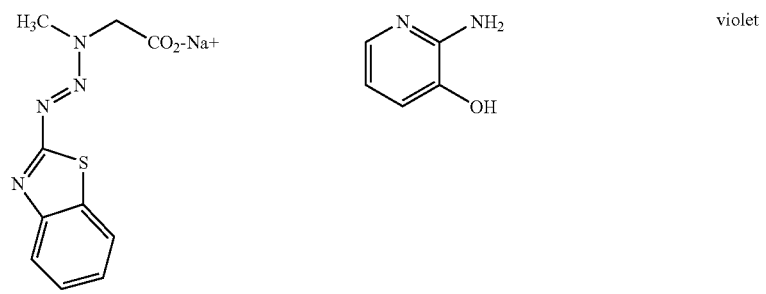 | | violet |

-continued
| Triazene | Coupler | Hair colour |
|---|---|---|
| Example 34: 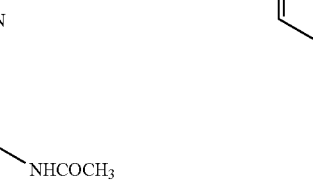 | 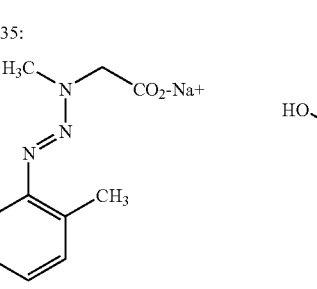 | red |
| Example 35: 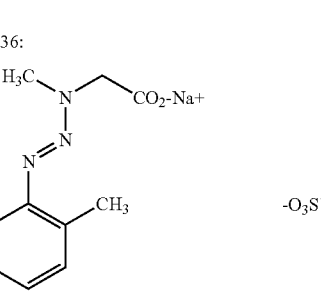 | 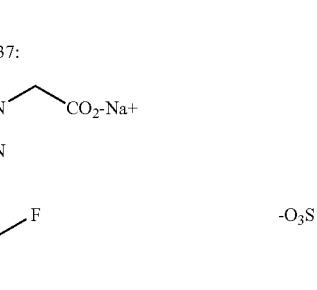 | vivid yellow |
| Example 36: 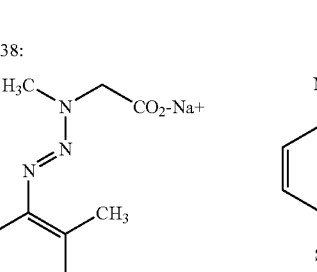 | | scarlet |
| Example 37: | | copper-red |
| Example 38: | | vivid red |

-continued
| Triazene | Coupler | Hair colour |
|---|---|---|
| Example 39: 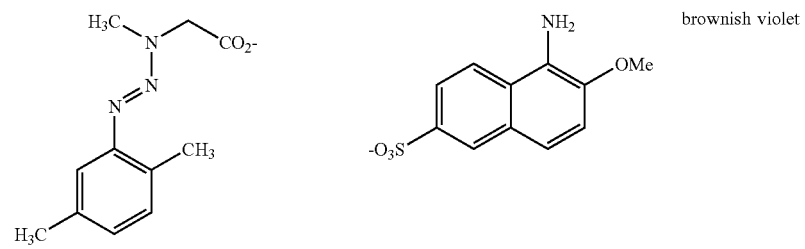 | | brownish violet |
| Example 40: 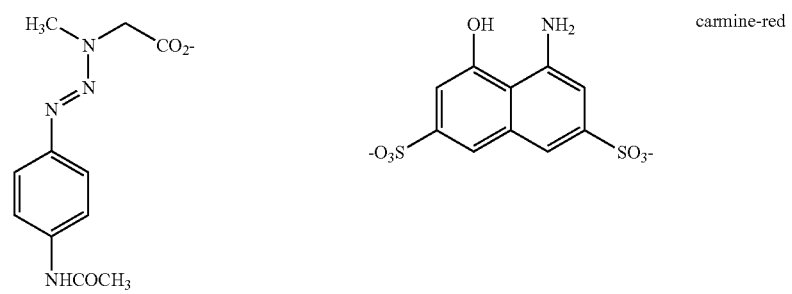 | | carmine-red |
| Example 41: 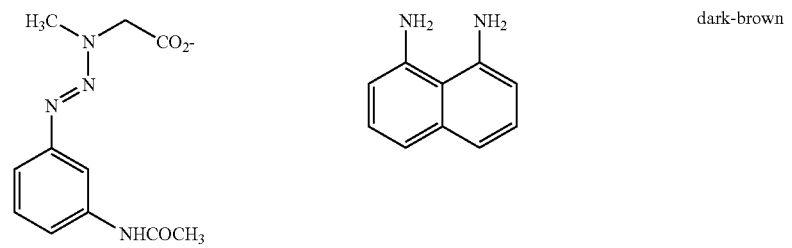 | | dark-brown |
| Example 42: 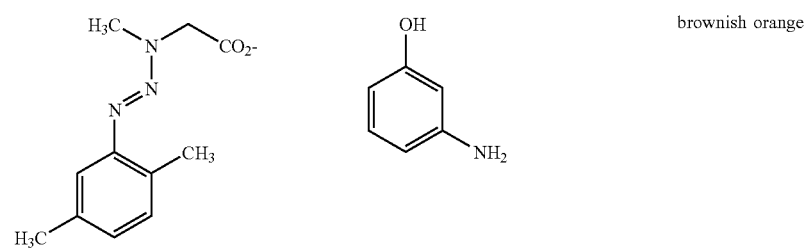 | | brownish orange |
| Example 43: 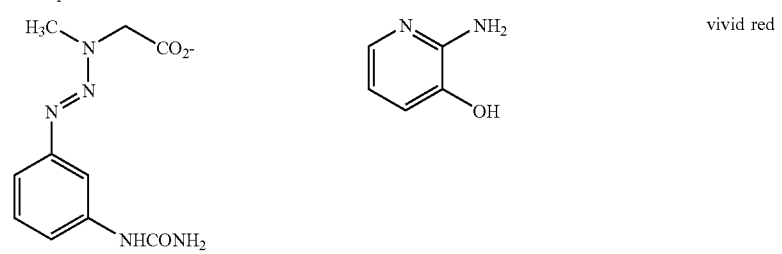 | | vivid red |

| Triazene | Coupler | Hair colour |
|---|---|---|
| Example 44: 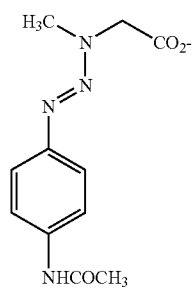 | 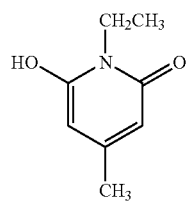 | vivid yellow |
| Example 45: 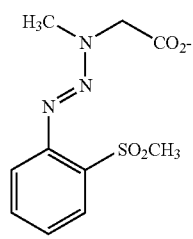 | 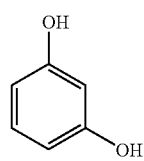 | orange |
| Example 46: 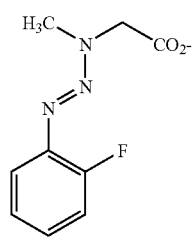 | 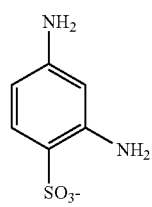 | reddish orange |
| Example 47: 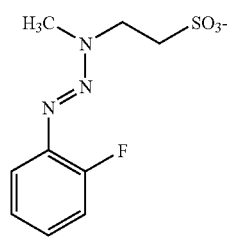 | 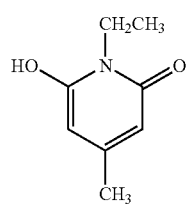 | lemon-yellow |
| Example 48: 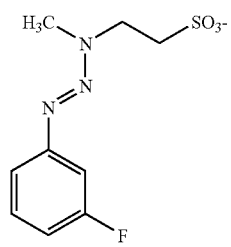 | 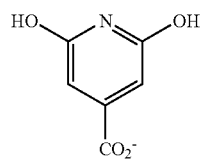 | straw-yellow |

-continued
| Triazene | Coupler | Hair colour |
|---|---|---|
Example 49:
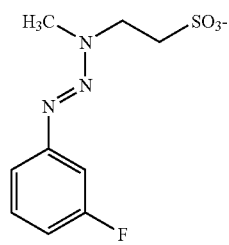 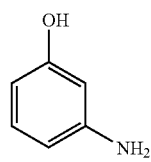 brownish orange
Example 50:
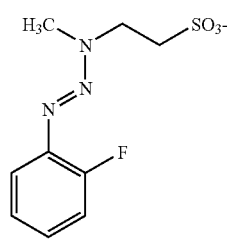 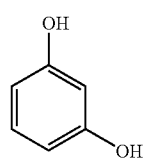 dull orange
Example 51:
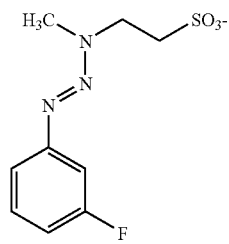 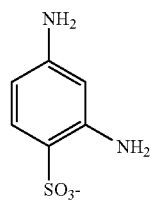 reddish orange
Example 52:
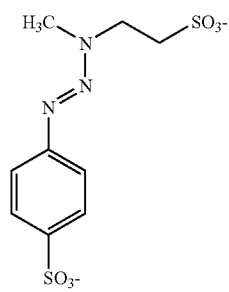 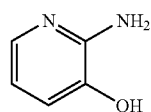 red
Example 53:
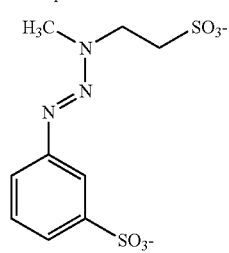 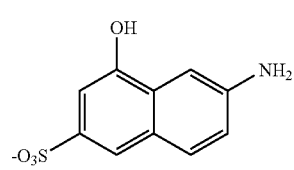 red -continued

| Triazene | Coupler | Hair colour |
|---|---|---|
| Example 54: [3-fluorophenyl-N=N-N(CH₃)-CH₂CH₂SO₃⁻] | 8-amino-1-hydroxy-naphthalene-3,6-disulfonate | cherry-red |
| Example 55: [2-fluorophenyl-N=N-N(CH₃)-CH₂CH₂SO₃⁻] | 4,5-diamino-naphthalene-1-sulfonate | purplish black |
| Example 56: [2-sulfonatophenyl-N=N-N(CH₃)-CH₂CO₂⁻] | 2,6-dihydroxy-pyridine-4-carboxylate | vivid yellow |
| Example 57: [2-sulfonatophenyl-N=N-N(CH₃)-CH₂CO₂⁻] | resorcinol | dull yellow |
| Example 58: [2-sulfonatophenyl-N=N-N(CH₃)-CH₂CO₂⁻] | 3-aminophenol | greenish brown |

| Triazene | Coupler | Hair colour |
|---|---|---|
| Example 59: 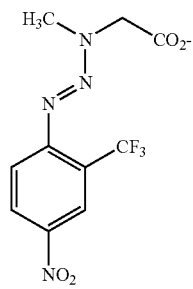 | 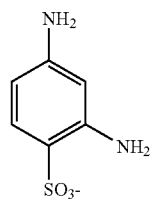 | orange |
| Example 60: 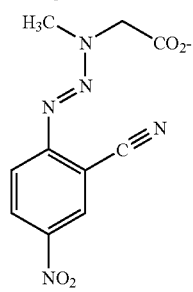 | 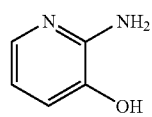 | ruby-red |
| Example 61: 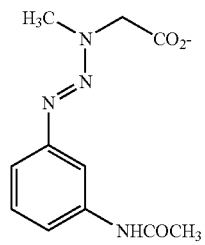 | 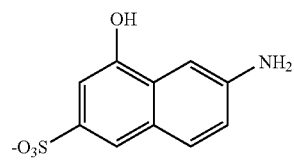 | pure red |
| Example 62: 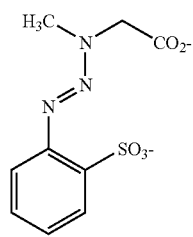 | 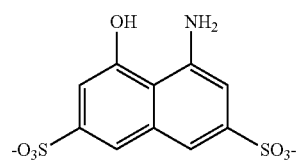 | reddish purple |
| Example 63: 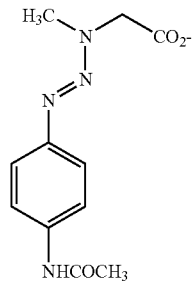 | 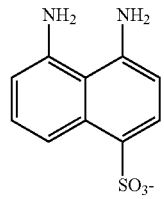 | violet |

-continued

| Triazene | Coupler | Hair colour |
|---|---|---|
| Example 64: [structure: H3C-N(CH2CO2-)-N=N-phenyl-3-F] | [structure: 1-amino-2-methoxy-6-sulfonatonaphthalene] | reddish brown |
| Example 65: [structure: 4-sulfonatophenyl-N=N-NH- ; 3-F on phenyl] | [structure: 8-amino-1-hydroxy-3,6-disulfonatonaphthalene] | red |
| Example 66: [structure: H3C-N(4-sulfonatophenyl)-N=N-phenyl with 2-OCH3, 4-NO2] | [structure: 8-amino-1-hydroxy-3,6-disulfonatonaphthalene] | red |
| Example 67: [structure: H3C-N(CH2CO2-)-N=N-phenyl with 2-CF3, 4-NO2] | [structure: 8-amino-1-hydroxy-3,6-disulfonatonaphthalene] | red |
| Example 68: [structure: H3C-N(CH2CO2-Na+)-N=N-phenyl-3-NO2] | [structure: 8-amino-1-hydroxy-3,6-disulfonatonaphthalene] | cherry-red |

| Triazene | Coupler | Hair colour |
|---|---|---|
| Example 69: 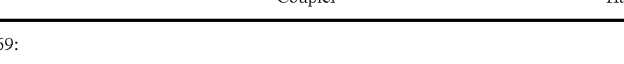 | | carmine-red |

EXAMPLE 70

A strand of bleached human hair is coloured with 10 g of composition A.

| Composition A (pH = 10) | |
|---|---|
| Ingredients | wt.-% |
| cetyl stearyl alcohol | 11.00 |
| oleth-5 | 5.0 |
| oleic acid | 2.5 |
| stearic acid monoethanolamide | 2.5 |
| coconut fatty acid monoethanolamide | 2.5 |
| sodium lauryl sulfate | 1.7 |
| 1,2-propanediol | 1.0 |
| ammonium chloride | 0.5 |
| EDTA, tetrasodium salt | 0.2 |
| perfume | 0.4 |
| wheat protein hydrolysate | 0.2 |
| silica | 0.1 |
| triazene of Example 52 (sodium salt) | 6.88 |
| coupler of Example 52 | 2.2 |
| water | ad 100 |

The mixture is allowed to act on the strand for 15 minutes at about 22° C. Then 10 g of a mixture of a 2% strength aqueous citric acid gel containing 4% sodium citrate, are applied to the strand and then combed through, whereupon a pH of about 3 is achieved. After contact for 30 minutes, the strand is thoroughly rinsed and then dried.

A strong, intense, striking cherry red coloration having good fastness to washing and fastness to rubbing properties is obtained.

EXAMPLE 71

A strand of medium blond human hair is treated with a mixture of equal parts by weight—5 g in each case—of 6% hydrogen peroxide solution and of composition B.

| Composition B (pH = 9.8) | |
|---|---|
| Ingredients | wt.-% |
| cetyl stearyl alcohol | 11.00 |
| oleth-5 | 5.0 |
| oleic acid | 2.5 |
| stearic acid monoethanolamide | 2.5 |
| coconut fatty acid monoethanolamide | 2.5 |
| sodium lauryl sulfate | 1.7 |
| 1,2-propanediol | 1.0 |
| ammonium chloride | 0.5 |
| EDTA, tetrasodium salt | 0.2 |
| perfume | 0.4 |
| wheat protein hydrolysate | 0.2 |
| silica | 0.1 |
| 2,5-diaminotoluene sulfate | 0.7 |
| 4-amino-2-hydroxytoluene | 0.5 |
| 2,5,6-triamino-4-hydroxypyrimidine sulfate | 0.2 |
| sodium sulfite | 1.0 |
| ascorbic acid | 0.5 |
| triazene of Example 52 (sodium salt) | 13.76 |
| coupler of Example 52 | 4.4 |
| Ammonia (25%) | 9.2 |
| water | ad 100 |

After contact for 15 minutes at room temperature, about 22° C., 10 g of a mixture of a 12.5% strength aqueous citric acid gel containing 0.1% by weight of a violet dye of the following formula

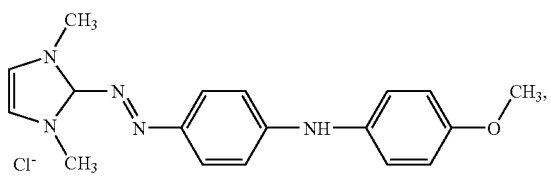

which is prepared analogously to WO 01/66646, Example 4, is applied to the strand. The strand is then combed through, whereupon a pH of about 7 is achieved. After contact for a further 15 minutes, the strand is again treated with 10 g of the above mixture of citric acid gel and violet dye, whereupon a pH of about 4 is achieved. The mixture is allowed to act for 5 minutes at pH 4 and the strand is then washed with water and shampoo and then again with water. The strand is then dried.

A strong, intense, striking red violet coloration having good fastness to washing and fastness to rubbing properties is obtained.

EXAMPLE 72

A strand of medium-blond human hair is coloured with a mixture of equal parts by weight—5 g in each case—of 6% hydrogen peroxide solution and of composition B according to Example 71.

The mixture is allowed to act on the strand for 20 minutes at room temperature, about 22° C. 10 g of a mixture of a 2% strength aqueous citric acid gel containing 0.1% by weight of a violet dye according to the above formula in Example 71, and 4% sodium citrate, are then applied to the strand. The strand is then combed through, whereupon a pH of about 3 is achieved. After contact for 30 minutes, the strand is thoroughly rinsed and then dried. A strong, intense, striking red violet coloration having good fastness to washing and fastness to rubbing properties is obtained.

EXAMPLE 73

A strand of brown human hair is coloured with a mixture of equal parts by weight—5 g in each case—of 6% hydrogen peroxide solution and of composition C.

Composition C (pH = 9.8)

| Ingredients | wt.-% |
| --- | --- |
| cetyl stearyl alcohol | 11.00 |
| oleth-5 | 5.0 |
| oleic acid | 2.5 |
| stearic acid monoethanolamide | 2.5 |
| coconut fatty acid monoethanolamide | 2.5 |
| sodium lauryl sulfate | 1.7 |
| 1,2-propanediol | 1.0 |
| ammonium chloride | 0.5 |
| EDTA, tetrasodium salt | 0.2 |
| perfume | 0.4 |
| wheat protein hydrolysate | 0.2 |
| silica | 0.1 |
| triazene of Example 52 (sodium salt) | 13.76 |
| coupler of Example 52 | 4.4 |
| water | ad 100 |

The mixture is allowed to act on the strand for 30 minutes at about 22° C. 10 g of a mixture of a 2% strength aqueous citric acid gel containing 0.1% by weight of a violet dye according to the above formula in Example 71, and 4% sodium citrate, are then applied to the strand. The strand is then combed through, whereupon a pH of about 3 is achieved. After contact for 5 minutes, the strand is thoroughly rinsed and then dried.

A strong, intense, striking red violet coloration having good fastness to washing and fastness to rubbing properties is obtained.

EXAMPLE 74

A strand of brown human hair is coloured with a mixture of equal parts by weight—5 g in each case—of 6% hydrogen peroxide solution and of composition D.

Composition D (pH = 9.8)

| Ingredients | wt.-% |
| --- | --- |
| cetyl stearyl alcohol | 11.00 |
| oleth-5 | 5.0 |
| oleic acid | 2.5 |
| stearic acid monoethanolamide | 2.5 |
| coconut fatty acid monoethanolamide | 2.5 |
| sodium lauryl sulfate | 1.7 |
| 1,2-propanediol | 1.0 |
| ammonium chloride | 0.5 |
| EDTA, tetrasodium salt | 0.2 |
| perfume | 0.4 |
| wheat protein hydrolysate | 0.2 |
| silica | 0.1 |
| triazene of Example 51 | 11.32 |
| coupler of Example 51 (sodium salt) | 4.2 |
| coupler of example 52 | 2.2 |
| water | ad 100 |

The mixture is allowed to act on the strand for 30 minutes at about 22° C. 10 g of a mixture of a 2% strength aqueous citric acid gel containing 0.1% by weight of a violet dye according to the above formula in Example 71, and 4% sodium citrate, are then applied to the strand. The strand is then combed through, whereupon a pH of about 3 is achieved. After contact for 5 minutes, the strand is thoroughly rinsed and then dried.

A strong, intense, striking copper coloration having good fastness to washing and fastness to rubbing properties is obtained.

EXAMPLE 75

A strand of brown human hair is coloured with a mixture of equal parts by weight—5 g in each case—of 6% hydrogen peroxide solution and of composition E.

Composition E (pH = 9.8)

| Ingredients | wt.-% |
| --- | --- |
| cetyl stearyl alcohol | 11.00 |
| oleth-5 | 5.0 |
| oleic acid | 2.5 |
| stearic acid monoethanolamide | 2.5 |
| coconut fatty acid monoethanolamide | 2.5 |
| sodium lauryl sulfate | 1.7 |
| 1,2-propanediol | 1.0 |
| ammonium chloride | 0.5 |
| EDTA, tetrasodium salt | 0.2 |
| perfume | 0.4 |
| wheat protein hydrolysate | 0.2 |
| silica | 0.1 |
| coupler of Example 52 | 4.4 |
| triazene of Example 52 (sodium salt) | 6.88 |
| triazene of Example 43 (sodium salt) | 5.46 |
| water | ad 100 |

The mixture is allowed to act on the strand for 30 minutes at about 22° C. 10 g of a mixture of a 2% strength aqueous citric acid gel containing 0.1% by weight of a violet dye according to the above formula in Example 71, and 4% sodium citrate, are then applied to the strand. The strand is then combed through, whereupon a pH of about 3 is achieved. After contact for 5 minutes, the strand is thoroughly rinsed and then dried.

A strong, intense, bluish red coloration having good fastness to washing and fastness to rubbing properties is obtained.

EXAMPLE 76

A strand of blond undamaged human hair is coloured with a mixture of equal parts by weight—5 g in each case—of 6% hydrogen peroxide solution and of composition F.

| Composition F (pH = 9.8) | |
|---|---|
| Ingredients | wt.-% |
| cetyl stearyl alcohol | 11.00 |
| oleth-5 | 5.0 |
| oleic acid | 2.5 |
| stearic acid monoethanolamide | 2.5 |
| coconut fatty acid monoethanolamide | 2.5 |
| sodium lauryl sulfate | 1.7 |
| 1,2-propanediol | 1.0 |
| ammonium chloride | 0.5 |
| EDTA, tetrasodium salt | 0.2 |
| perfume | 0.4 |
| wheat protein hydrolysate | 0.2 |
| silica | 0.1 |
| Basic Red 51 | 0.2 |
| triazene of Example 52 (sodium salt) | 13.76 |
| coupler of Example 52 | 4.4 |
| water | ad 100 |

A) The mixture is allowed to act on the strand for 30 minutes at about 22° C. 10 g of a mixture of a 2% strength aqueous citric acid gel containing 0.1% by weight of Basic Red 51 and 4% sodium citrate, are then applied to the strand; the latter is then combed through, whereupon a pH of about 3 is achieved. After contact for 5 minutes, the strand is thoroughly rinsed and then dried.

A strong, intense, striking red coloration having good fastness to washing and fastness to rubbing properties is obtained.

B) The mixture is allowed to act on the strand for 30 minutes at about 22° C. 10 g of a mixture of a 2% strength aqueous citric acid gel containing 4% sodium citrate, are then applied to the strand; the latter is then combed through, whereupon a pH of about 3 is achieved. After contact for 5 minutes, the strand is thoroughly rinsed and then dried.

A strong, intense, striking red coloration having good fastness to washing and fastness to rubbing properties is obtained.

C) The mixture is allowed to act on the strand for 30 minutes at about 22° C. 10 g of a mixture of a 2% strength aqueous citric acid gel containing 0.1% by weight of Basic Yellow 87 and 4% sodium citrate, are then applied to the strand; the latter is then combed through, whereupon a pH of about 3 is achieved. After contact for 5 minutes, the strand is thoroughly rinsed and then dried.

A strong, intense, striking copper red coloration having good fastness to washing and fastness to rubbing properties is obtained.

EXAMPLE 77

A strand of bleached human hair is coloured with 10 g of composition G.

| Composition G (pH = 10) | |
|---|---|
| Ingredients | wt.-% |
| cetyl stearyl alcohol | 11.00 |
| oleth-5 | 5.0 |

-continued

| Composition G (pH = 10) | |
|---|---|
| Ingredients | wt.-% |
| oleic acid | 2.5 |
| stearic acid monoethanolamide | 2.5 |
| coconut fatty acid monoethanolamide | 2.5 |
| sodium lauryl sulfate | 1.7 |
| 1,2-propanediol | 1.0 |
| ammonium chloride | 0.5 |
| EDTA, tetrasodium salt | 0.2 |
| perfume | 0.4 |
| wheat protein hydrolysate | 0.2 |
| silica | 0.1 |
| violet dye of Example 71 | 0.2 |
| triazene of Example 30 | 4.66 |
| coupler of Example 30 | 3.16 |
| water | ad 100 |

The mixture is allowed to act on the strand for 30 minutes at about 22° C. 10 g of a mixture of a 2% strength aqueous citric acid gel containing 4% sodium citrate are then applied to the strand; the latter is then combed through, whereupon a pH of about 3 is achieved. After contact for 5 minutes, the strand is thoroughly rinsed and then dried.

A strong, intense, striking violet coloration having good fastness to washing and fastness to rubbing properties is obtained.

EXAMPLE 78

A strand of bleached human hair is coloured with 10 g of composition H.

| Composition H (pH = 10) | |
|---|---|
| Ingredients | wt.-% |
| cetyl stearyl alcohol | 11.00 |
| oleth-5 | 5.0 |
| oleic acid | 2.5 |
| stearic acid monoethanolamide | 2.5 |
| coconut fatty acid monoethanolamide | 2.5 |
| sodium lauryl sulfate | 1.7 |
| 1,2-propanediol | 1.0 |
| ammonium chloride | 0.5 |
| EDTA, tetrasodium salt | 0.2 |
| perfume | 0.4 |
| wheat protein hydrolysate | 0.2 |
| silica | 0.1 |
| triazene of Example 36 | 4.88 |
| coupler of Example 36 | 4.79 |
| water | ad 100 |

The mixture is allowed to act on the strand for 15 minutes at about 22° C. Then 10 g of a mixture of a 2% strength aqueous citric acid gel containing 0.1% by weight of a red dye of the following formula

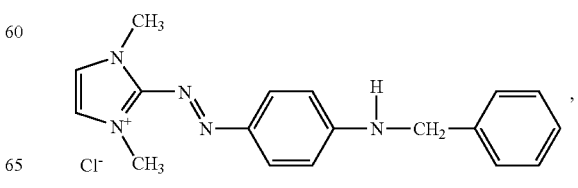

which can be prepared, for example, as described in WO 02/30374, according to Preparation Example 2, compound of formula 101, and 4% sodium citrate, are applied to the strand and then combed through, whereupon a pH of about 3 is achieved. After contact for 35 minutes, the strand is thoroughly rinsed and then dried.

A strong, intense, striking scarlet coloration having good fastness to washing and fastness to rubbing properties is obtained.

EXAMPLE 79

A strand of bleached human hair is coloured with 10 g of composition I.

| Composition I (pH = 10) | |
|---|---|
| Ingredients | wt.-% |
| cetyl stearyl alcohol | 11.00 |
| oleth-5 | 5.0 |
| oleic acid | 2.5 |
| stearic acid monoethanolamide | 2.5 |
| coconut fatty acid monoethanolamide | 2.5 |
| sodium lauryl sulfate | 1.7 |
| 1,2-propanediol | 1.0 |
| ammonium chloride | 0.5 |
| EDTA, tetrasodium salt | 0.2 |
| perfume | 0.4 |
| wheat protein hydrolysate | 0.2 |
| silica | 0.1 |
| triazene of Example 36 | 4.88 |
| coupler of Example 36 | 4.79 |
| Basic Orange 31 | 0.2 |
| water | ad 100 |

The mixture is allowed to act on the strand for 30 minutes at about 22° C. Then 10 g of a mixture of a 2% strength aqueous citric acid gel containing 4% sodium citrate, are applied to the strand and then combed through, whereupon a pH of about 3 is achieved. After contact for 5 minutes, the strand is thoroughly rinsed and then dried.

A strong, intense, striking scarlet coloration having good fastness to washing and fastness to rubbing properties is obtained.

EXAMPLE 80

A strand of blond undamaged human hair is coloured with 10 g of composition J.

| Composition J (pH = 10) | |
|---|---|
| Ingredients | wt.-% |
| cetyl stearyl alcohol | 11.00 |
| oleth-5 | 5.0 |
| oleic acid | 2.5 |
| stearic acid monoethanolamide | 2.5 |
| coconut fatty acid monoethanolamide | 2.5 |
| sodium lauryl sulfate | 1.7 |
| 1,2-propanediol | 1.0 |
| ammonium chloride | 0.5 |
| EDTA, tetrasodium salt | 0.2 |
| perfume | 0.4 |
| wheat protein hydrolysate | 0.2 |
| silica | 0.1 |
| triazene of Example 36 | 4.88 |
| coupler of Example 36 | 4.79 |
| water | ad 100 |

After contact for 30 minutes, without being washed out, a dye mixture known from U.S. Pat. No. 6,248,314 and having the following composition:

| | |
|---|---|
| Black Color No. 401 | 0.1 |
| Purple Color 401 | 0.05 |
| Orange Color No. 205 | 0.1 |
| benzyl alcohol | 2.0 |
| ethylene carbonate | 10 |
| propylene carbonate | 15 |
| ethanol | 10 |
| lactic acid | 3.5 |
| sodium carbonate solution | of pH 2.9 |
| hydroxyethyl cellulose | 1.5 |
| water | ad 100 | is applied to the hair. The hair is then combed through thoroughly, whereupon its pH becomes about 3. Then, after a contact period of 15 minutes, the hair is rinsed thoroughly with water and dried.

A strong, intense, striking red coloration having good fastness to washing and fastness to rubbing properties is obtained.

EXAMPLE 81

A strand of blond undamaged human hair is coloured with 10 g of a composition consisting of 5 g each of compositions A and B.

| | Compositions | | | |
|---|---|---|---|---|
| | A | B | C | D |
| cetyl stearyl alcohol | 11.00 | 11.00 | 11.00 | 11.00 |
| oleth-5 | 5.0 | 5.0 | 5.0 | 5.0 |
| oleic acid | 2.5 | 2.5 | 2.5 | 2.5 |
| stearic acid monoethanolamide | 2.5 | 2.5 | 2.5 | 2.5 |
| coconut fatty acid monoethanolamide | 2.5 | 2.5 | 2.5 | 2.5 |
| sodium lauryl sulfate | 1.7 | 1.7 | 1.7 | 1.7 |
| 1,2-propanediol | 1.0 | 1.0 | 1.0 | 1.0 |
| ammonium chloride | 0.5 | 0.5 | 0.5 | 0.5 |
| EDTA, tetrasodium salt | 0.2 | 0.2 | 0.2 | 0.2 |
| perfume | 0.4 | 0.4 | 0.4 | 0.4 |
| wheat protein hydrolysate | 0.2 | 0.2 | 0.2 | 0.2 |
| silica | 0.1 | 0.1 | 0.1 | 0.1 |
| 2,5-diaminotoluene sulfate | | | 0.7 | |
| 4-amino-2-hydroxytoluene | | | 0.5 | |
| 2,5,6-triamino-4-hydroxypyrimidine sulfate | | | 0.2 | |
| sodium sulfite | | | 1.0 | |
| ascorbic acid | | | 0.5 | |
| triazene of Example 52 | 13.76 | | | |
| coupler of Example 52 | | 4.4 | | |
| Basic Red 51 | | | | 0.4 |
| Ammonia (25%) | 9.2 | 9.2 | 9.2 | 9.2 |
| composition: pH | 9.8 | 9.8 | 9.8 | 9.8 |
| water | ad 100 | ad 100 | ad 100 | ad 100 |

The colouring mixture is allowed to act on the hair for 30 minutes at about 22° C. 10 g of a 2% strength aqueous citric acid gel are then applied to the strand. After contact for 15 minutes, the strand is rinsed thoroughly, shampooed and then dried.

A strong, intense, striking red coloration having good fastness to washing and fastness to rubbing properties is obtained.

EXAMPLE 82

A strand of blond undamaged human hair is coloured with a mixture of 15 g of 6% hydrogen peroxide solution and a composition consisting of 5 g each of compositions A, B and C according to Example 81.

The colouring mixture is allowed to act on the hair for 30 minutes at about 22° C. 10 g of a 2% strength aqueous citric acid gel are then applied to the strand. After contact for 5 minutes, the strand is rinsed thoroughly, shampooed and then dried.

A strong, intense, striking red violet coloration having good fastness to washing and fastness to rubbing properties is obtained.

EXAMPLE 83

A strand of blond undamaged human hair is coloured with a mixture of 20 g of 6% hydrogen peroxide solution and a composition consisting of 5 g each of compositions A, B, C and D according to Example 81.

The colouring mixture is allowed to act on the hair for 30 minutes at about 22° C. 10 g of a 2% strength aqueous citric acid gel are then applied to the strand. After contact for 5 minutes, the strand is rinsed thoroughly, shampooed and then dried.

A strong, intense, striking red violet coloration having good fastness to washing and fastness to rubbing properties is obtained.

EXAMPLE 84

A strand of blond undamaged human hair is coloured with a mixture of 15 g of 6% hydrogen peroxide solution and a composition consisting of 5 g each of compositions A, B and D according to Example 81.

The colouring mixture is allowed to act on the hair for 30 minutes at about 22° C. 10 g of a 2% strength aqueous citric acid gel are then applied to the strand. After contact for 5 minutes, the strand is rinsed thoroughly, shampooed and then dried.

A strong, intense, striking red coloration having good fastness to washing and fastness to rubbing properties is obtained.

EXAMPLE 85

A strand of blond undamaged human hair is coloured with 15 g of a composition consisting of 5 g each of compositions A, B and D according to Example 81.

The colouring mixture is allowed to act on the hair for 30 minutes at about 22° C. 10 g of a 2% strength aqueous citric acid gel are then applied to the strand. After contact for 5 minutes, the strand is rinsed thoroughly, shampooed and then dried.

A strong, intense, striking red coloration having good fastness to washing and fastness to rubbing properties is obtained.

EXAMPLE 86

A strand of blond undamaged human hair is coloured with 15 g of a composition consisting of 5 g each of compositions A, B and D according to Example 81.

The colouring mixture is allowed to act on the hair for 30 minutes at about 22° C. 10 g of a shampoo with a pH value of 3 are then applied to the strand and are massaged in. After contact for 5 minutes, the strand is rinsed thoroughly and then dried.

A strong, intense, striking red coloration having good fastness to washing and fastness to rubbing properties is obtained.

What is claimed is:

1. A method of colouring porous material, which method comprises applying to the material being coloured, in any desired order successively, or simultaneously, a) at least one capped diazonium compound of formula (1)

wherein

Q is an unsubstituted phenyl; naphthyl; thiophenyl; 1,3-thiazolyl; 1,2-thiazolyl; 1,3-benzothiazolyl; 2,3-benzothiazolyl; imidazolyl; 1,3,4-thiadiazolyl; 1,3,5-thiadiazolyl; 1,3,4-triazolyl; pyrazolyl; benzimidazolyl; benzopyrazolyl; pyridinyl; quinolinyl; pyrimidinyl; isoxazolyl; aminodiphenyl; aminodiphenylether and azobenzenyl or Q is a phenyl, naphthyl, thiophenyl, 1,3-thiazolyl, 1,2-thiazolyl, 1,3-benzothiazolyl, 2,3-benzothiazolyl, imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl, aminodiphenyl, aminodiphenylether and azobenzenyl which is mono- or poly-substituted by $C_1$–$C_4$alkyl, $C_1$–$C_4$alkoxy, $C_1$–$C_4$alkylthio, halogen, nitro, trifluoromethyl, CN, SCN, $C_1$–$C_4$alkylsulfonyl, phenylsulfonyl, benzylsulfonyl, di-$C_1$–$C_4$alkylaminosulfonyl, $C_1$–$C_4$alkyl-carbonylamino, $C_1$–$C_4$alkoxysulfonyl or by di-(hydroxy-$C_1$–$C_4$alkyl)-aminosulfonyl, R is a radical of formula —$NR_{16}R_{17}$, wherein $R_{16}$ is H; unsubstituted linear or branched $C_1$–$C_6$alkyl or linear or branched $C_1$–$C_6$alkyl, which is substituted by one or more identical or different substituent selected from the group consisting of $OC_1$–$C_4$alkyl, COOH, $COOC_1$–$C_2$alkyl, $SO_3H$, $NH_2$, CN, halogen and OH, and $R_{17}$ is unsubstituted linear or branched $C_1$–$C_6$alkyl or linear or branched $C_1$–$C_6$alkyl, which is substituted by one or more identical or different substituent selected from the group consisting of $OC_1$–$C_4$alkyl, COOH, $COOC_1$–$C_2$alkyl, $SO_3H$, $NH_2$, CN, halogen and OH, and b) at least one water-soluble coupling component under conditions such that, initially, coupling does not take place, and then causing the capped diazonium compound present on the material to react with the coupling component, with the provisos that
(i) if the water-soluble coupling component is
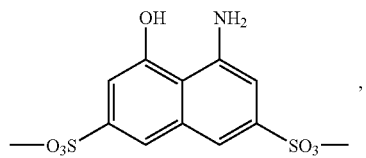
then the capped diazonium compounds is not
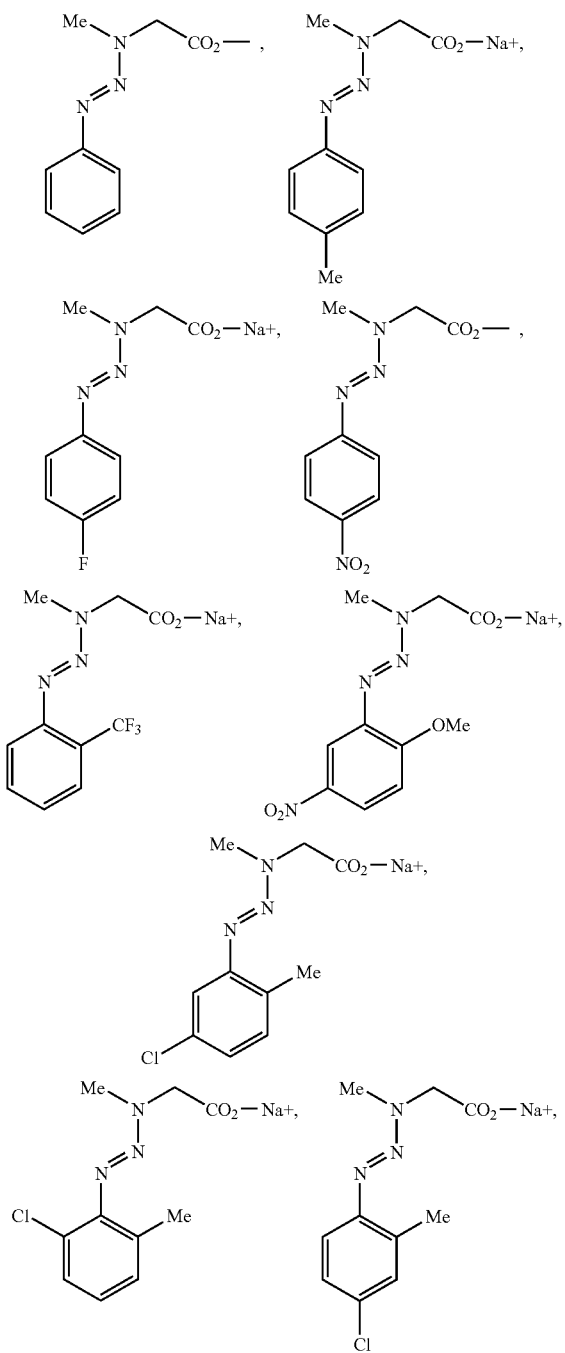
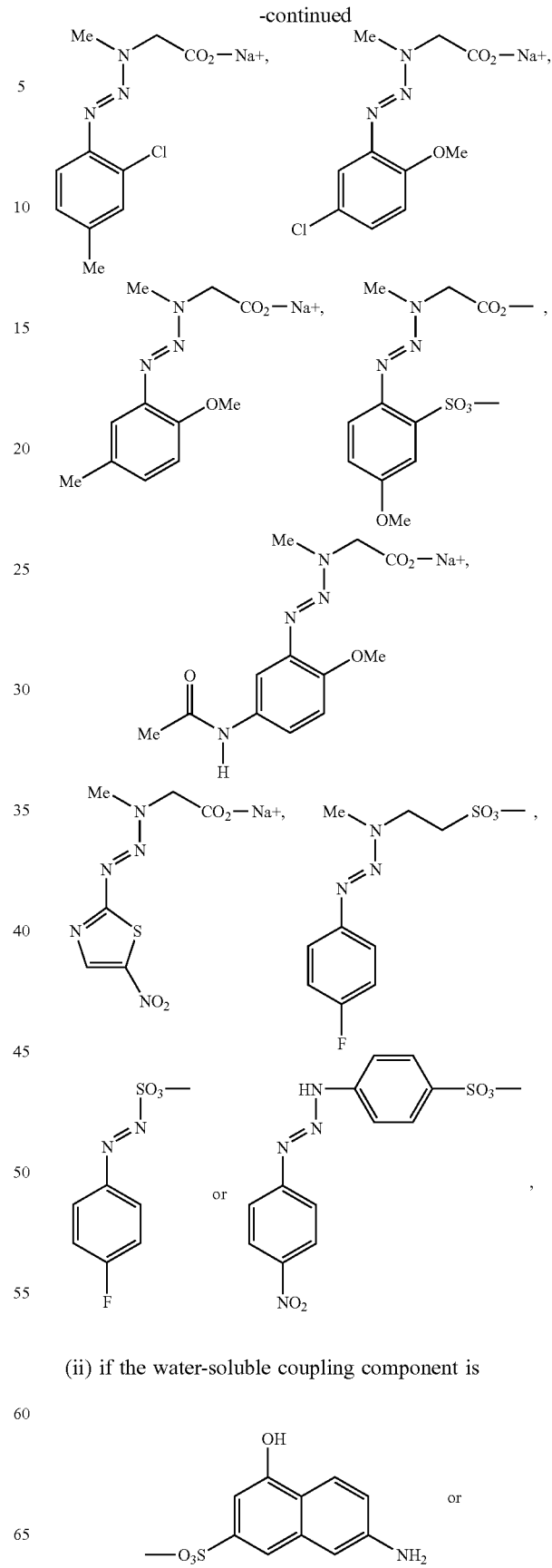
(ii) if the water-soluble coupling component is
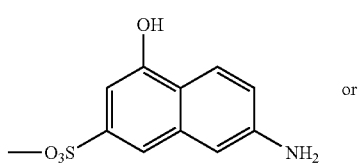

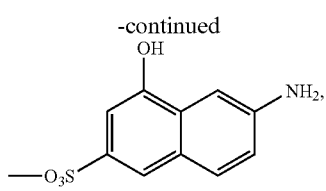
then the capped diazonium compound is not
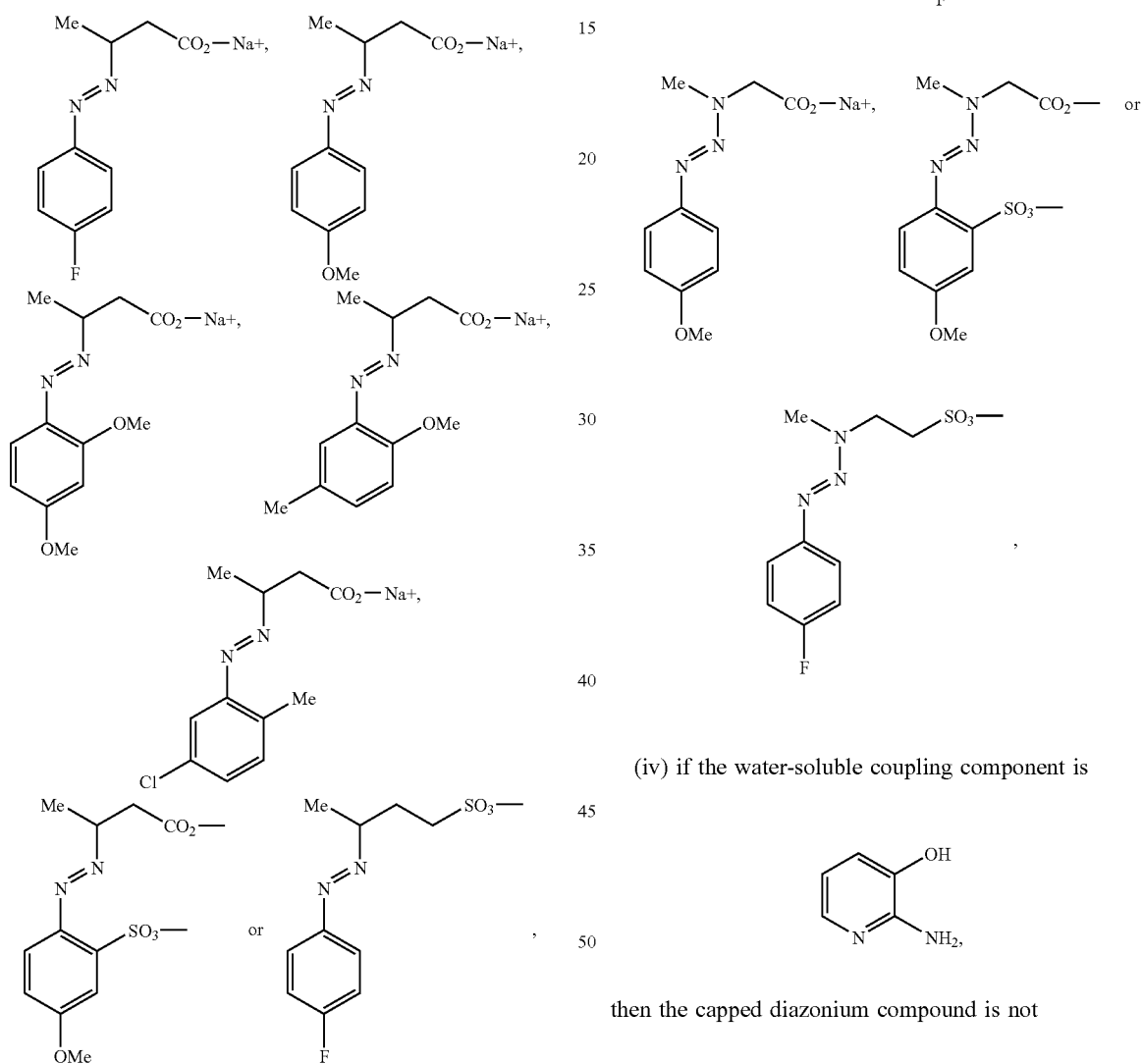
(iii) if the water-soluble coupling component is
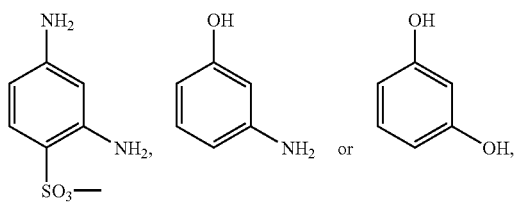
then the capped diazonium compound is not
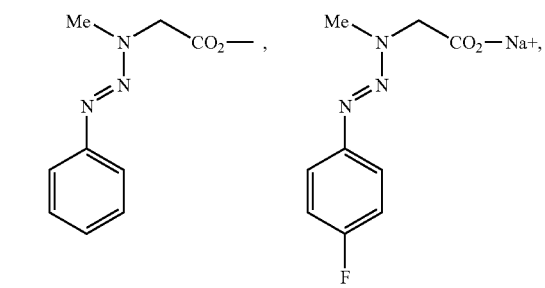
(iv) if the water-soluble coupling component is
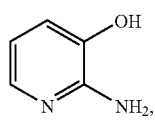
then the capped diazonium compound is not
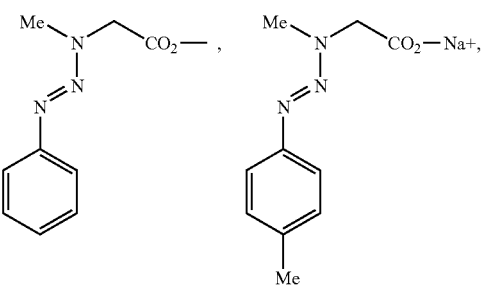

-continued
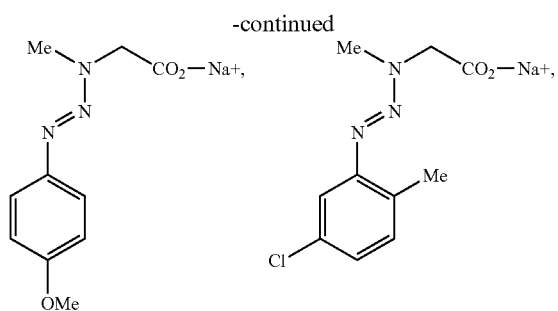
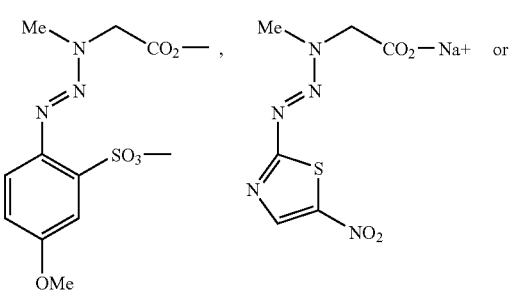
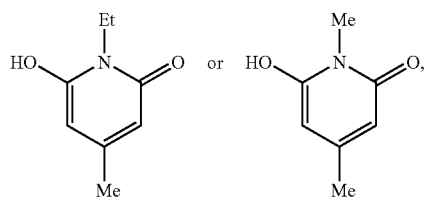
(v) if the water-soluble coupling component is
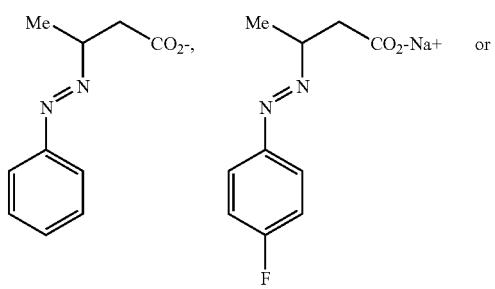
then the capped diazonium compound is not
-continued
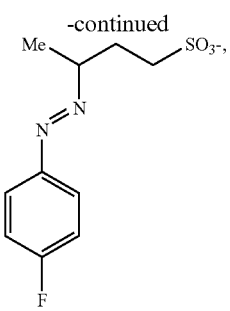
(vi) if the water-soluble coupling component is
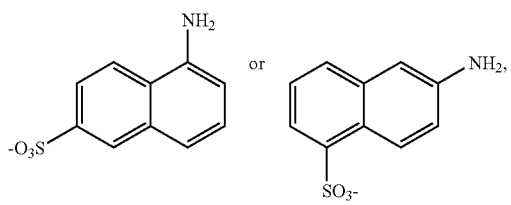
then the capped diazonium compound is not
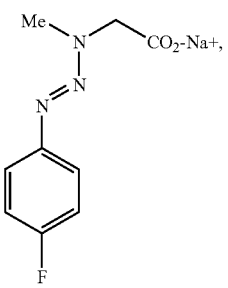
(vii) if the water-soluble coupling component is
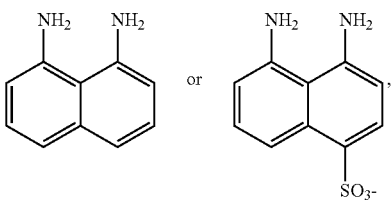
then the capped diazonium compound is not
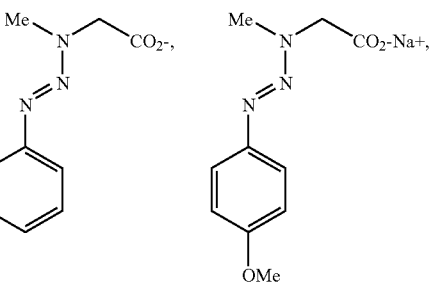

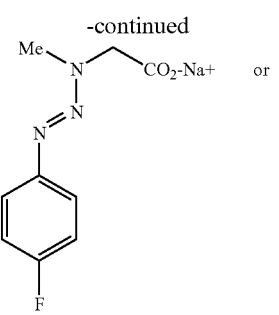

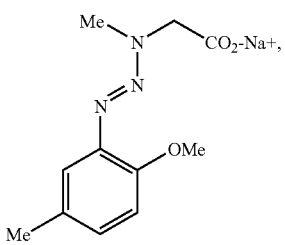

(viii) if the water-soluble coupling component is

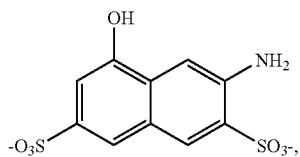

then the capped diazonium compound is not

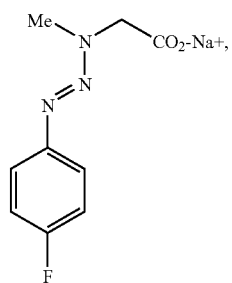

(ix) if the water-soluble coupling component is

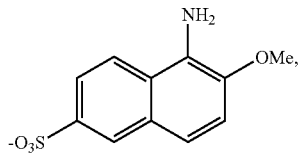

then the capped diazonium compound is not

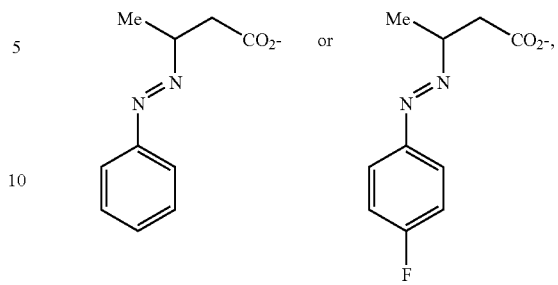

and (x) if the water-soluble coupling component is

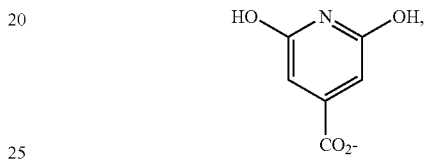

then the diazonium capped compound is not

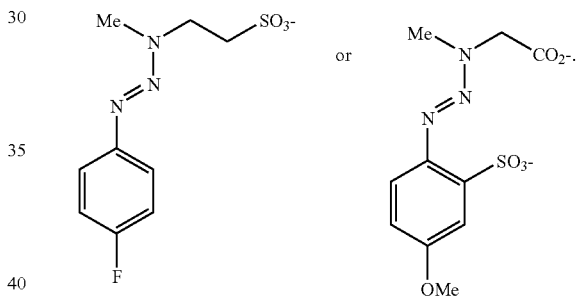

2. A method according to claim 1 wherein the coupling component is an unsubstituted or substituted acylacetarylamide, phenol, naphthol, pyridine, quinolone, pyrazole, indole, diphenylamine, aniline, aminopyridine, pyrimidone, naphthylamine, aminothiazole, thiophene or hydroxypyridine.

3. A method according to claim 2, wherein the coupling component is mono- or poly-substituted by amino, alkylamino, dialkylamino, halogen, alkyl, alkoxy, phenyl, naphthyl or by aryloxy.

4. A method according to claim 1, which method comprises applying to the material being coloured, in any desired order successively, or simultaneously, a) at least one capped diazonium compound of formula (1)

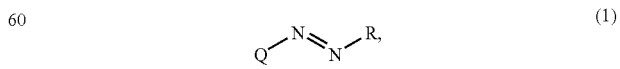

wherein

Q is an unsubstituted phenyl; naphthyl; thiophenyl; 1,3-thiazolyl; 1,2-thiazolyl; 1,3-benzothiazolyl; 2,3-benzothiazolyl; imidazolyl; 1,3,4-thiadiazolyl; 1,3,5-thiadiazolyl; 1,3,4-triazolyl; pyrazolyl; benzimidazolyl; benzopyrazolyl; pyridinyl; quinolinyl; pyrimidinyl; isoxazolyl; aminodiphenyl; aminodiphenylether and azobenzenyl or Q is a phenyl, naphthyl, thiophenyl, 1,3-thiazolyl, 1,2-thiazolyl, 1,3-benzothiazolyl, 2,3-benzothiazolyl, imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl, aminodiphenyl, aminodiphenylether and azobenzenyl which is mono- or poly-substituted by $C_1$–$C_4$alkyl, $C_1$–$C_4$alkoxy, $C_1$–$C_4$alkylthio, halogen, nitro, trifluoromethyl, CN, SCN, $C_1$–$C_4$alkylsulfonyl, phenylsulfonyl, benzylsulfonyl, di-$C_1$–$C_4$alkylaminosulfonyl, $C_1$–$C_4$alkyl-carbonylamino, $C_1$–$C_4$alkoxysulfonyl or by di-(hydroxy-$C_1$–$C_4$alkyl)-aminosulfonyl, R is a radical of formula —$NR_{16}R_{17}$, wherein $R_{16}$ is H; unsubstituted linear or branched $C_1$–$C_6$alkyl or linear or branched $C_1$–$C_6$alkyl, which is substituted by one or more identical or different substituent selected from the group consisting of $OC_1$–$C_4$alkyl, COOH, $COOC_1$–$C_2$alkyl, $SO_3H$, $NH_2$, CN, halogen and OH, and $R_{17}$ is unsubstituted linear or branched $C_1$–$C_6$alkyl or linear or branched $C_1$–$C_6$alkyl, which is substituted by one or more identical or different substituent selected from the group consisting of $OC_1$–$C_4$alkyl, COOH, $COOC_1$–$C_2$alkyl, $SO_3H$, $NH_2$, CN, halogen and OH, and b) at least one water-soluble coupling component selected from the group consisting of acylacetarylamides, phenols, naphthols, pyridones, quinolones, pyrazoles, indoles, diphenylamines, anilines, aminopyridines, pyrimidones, naphthylamines, aminothiazoles, thiophenes and hydroxypyridines, which all may carry further substituents selected from the group consisting of amino, alkylamino, dialkylamino, halogen, alkyl, alkoxy, aryl, aryloxy, hydroxy, carboxy and sulfo, under conditions such that, initially, coupling does not take place, and then causing the capped diazonium compound present on the material to react with the coupling component, wherein the same provisos as in claim 1 apply.

5. A method of colouring porous material according to claim 1, which method comprises applying to the material being coloured, in any desired order successively, or simultaneously, a) at least two capped diazonium compounds as defined in claim 1 and b) at least one water-soluble coupling component under conditions such that, initially, coupling does not take place, and then causing the capped diazonium compound present on the material to react with the coupling component.

6. A method of colouring porous material according to claim 1, which method comprises applying to the material being coloured, in any desired order successively, or simultaneously, a) at least one capped diazonium compound as defined in claim 1 and b) at least two water-soluble coupling components under conditions such that, initially, coupling does not take place, and then causing the capped diazonium compound present on the material to react with the coupling component.

7. A method of colouring porous material according to claim 1, which method comprises applying to the material being coloured, in any desired order successively, or simultaneously, a) at least two capped diazonium compounds as defined in claim 1 and b) at least two water-soluble coupling components under conditions such that, initially, coupling does not take place, and then causing the capped diazonium compound present on the material to react with the coupling component.

8. A method according to claim 1, which method comprises bringing the material being coloured into contact with a) at least one capped diazonium compound as defined in claim 1 and b) at least one water-soluble coupling component, in any desired order successively, or simultaneously, a) under alkaline conditions in the presence of an oxidising agent and optionally in the presence of a further dye, and then subjecting the material being coloured to treatment with acid, or b) under alkaline conditions, and then subjecting the material being coloured to treatment with acid, optionally in the presence of a further dye, wherein the same provisos as in claim 1 apply.

9. A method according to claim 5, wherein the coupling component is unsubstituted or substituted acylacetarylamide, phenol, naphthol, pyridine, quinolone, pyrazole, indole, diphenylamine, aniline, aminopyridine, pyrimidone, naphthylamine, aminothiazole, thiophene or hydroxypyridine.

10. A method according to claim 9, wherein the coupling component is mono- or poly-substituted by amino, alkylamino, dialkylamino, halogen, alkyl, alkoxy, phenyl, naphthyl or by aryloxy.

11. A colouring composition for carrying out the method according to claim 1, comprising a) at least one compound of formula (1) described in claim 1, b) a medium for adjusting the pH, c) water, and, optionally, d) further additives.

12. A colouring composition according to claim 11, comprising a) at least one compound of formula (1), b) a medium for adjusting the pH, c) water, d) at least one coupling component, and, optionally, e) further additives with the provisos that (i) if the water-soluble coupling component is

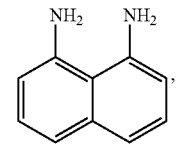

then the capped diazonium compound must not be

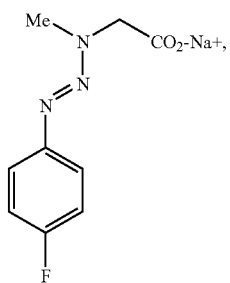

and (ii) if the water-soluble coupling component is

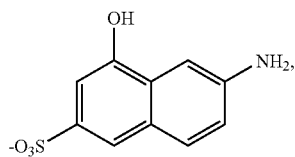

then the capped diazonium compound must not be

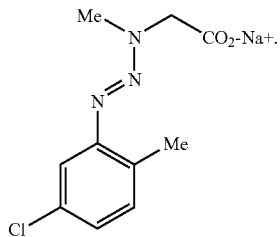

13. A colouring composition for carrying out the method according to claim 12, comprising
   a) at least one compound of formula (1),
   b) a medium for adjusting the pH,
   c) water,
   d) at least one water-soluble coupling component selected from the group consisting of acylacetarylamides, phenols, naphthols, pyridones, quinolones, pyrazoles, indoles, diphenylamines, anilines, aminopyridines, pyrimidones, naphthylamines, aminothiazoles, thiophenes and hydroxypyridines, which all may carry further substituents selected from the group consisting of amino, alkylamino, dialkylamino, halogen, alkyl, alkoxy, aryl, aryloxy, hydroxy, carboxy and sulfo and, optionally,
   e) further additives,
wherein the same provisos as in claim 12 apply.

14. A colouring composition for carrying out the method according to claim 12, comprising
   a) at least one compound of formula (1),
   b) a medium for adjusting the pH,
   c) water,
   d) at least one water-soluble coupling component selected from the group consisting of acylacetarylamides, phenols, naphthols, pyridones, quinolones, pyrazoles, indoles, diphenylamines, anilines, aminopyridines, pyrimidones, naphthylamines, aminothiazoles, thiophenes and hydroxypyridines, which all may carry further substituents selected from the group consisting of amino, alkylamino, dialkylamino, halogen, alkyl, alkoxy, aryl, aryloxy, hydroxy, carboxy and sulfo,
   e) a further dye which is an oxidation dye, or a cationic, anionic or uncharged direct dye,
   and, optionally,
   f) further additives,
wherein the same provisos as in claim 12 apply.

* * * * *